(12) United States Patent
Vidlund et al.

(10) Patent No.: US 11,589,985 B2
(45) Date of Patent: *Feb. 28, 2023

(54) APPARATUS AND METHODS FOR TRANSFEMORAL DELIVERY OF PROSTHETIC MITRAL VALVE

(71) Applicant: Tendyne Holdings, Inc., St. Paul, MN (US)

(72) Inventors: Robert M. Vidlund, Forest Lake, MN (US); Mark Christianson, Plymouth, MN (US); Igor Kovalsky, Minnetonka, MN (US)

(73) Assignee: Tendyne Holdings, Inc., St. Paul, MN (US)

( * ) Notice: Subject to any disclaimer, the term of this patent is extended or adjusted under 35 U.S.C. 154(b) by 371 days.

This patent is subject to a terminal disclaimer.

(21) Appl. No.: 16/233,363

(22) Filed: Dec. 27, 2018

(65) Prior Publication Data

US 2019/0125533 A1 May 2, 2019

Related U.S. Application Data

(63) Continuation of application No. 15/217,376, filed on Jul. 22, 2016, now Pat. No. 10,201,419.

(Continued)

(51) Int. Cl.
*A61F 2/24* (2006.01)
*A61B 17/00* (2006.01)
*A61B 17/34* (2006.01)

(52) U.S. Cl.
CPC ........ *A61F 2/2433* (2013.01); *A61B 17/0057* (2013.01); *A61F 2/2418* (2013.01);
(Continued)

(58) Field of Classification Search
CPC ...... A61F 2/24–2496; A61F 2002/9505; A61F 2002/9511; A61F 2220/0008; A61F 2220/0016; A61F 2/848–2002/8486
See application file for complete search history.

(56) References Cited

U.S. PATENT DOCUMENTS

| | | | |
|---|---|---|---|
| 2,697,008 | A | 12/1954 | Ross |
| 3,409,013 | A | 11/1968 | Berry |

(Continued)

FOREIGN PATENT DOCUMENTS

| | | | |
|---|---|---|---|
| CN | 1486161 A | 3/2004 | |
| CN | 1961845 A | 5/2007 | |

(Continued)

OTHER PUBLICATIONS

US 9,155,620 B2, 10/2015, Gross et al. (withdrawn)

(Continued)

*Primary Examiner* — Tan-Uyen T Ho
*Assistant Examiner* — Charles M Wei
(74) *Attorney, Agent, or Firm* — Wei & Sleman LLP

(57) ABSTRACT

Apparatus and methods are described herein for use in the transfemoral delivery and deployment of a prosthetic mitral valve. In some embodiments, a method includes inverting an outer frame of a prosthetic mitral valve when in a biased expanded configuration. After inverting the outer frame, the prosthetic mitral valve is inserted into a lumen of a delivery sheath such that the mitral valve is moved to a collapsed configuration. The delivery sheath is inserted into a femoral vein and moved through the femoral vein and a septum of a heart until a distal end of the delivery sheath is disposed in the left atrium of the heart. The prosthetic mitral valve is moved distally out of the delivery sheath such that the inverted outer frame reverts and the prosthetic mitral valve assumes its biased expanded configuration. The prosthetic (Continued)

mitral valve is then positioned within a mitral annulus of the heart.

20 Claims, 39 Drawing Sheets

Related U.S. Application Data

(60) Provisional application No. 62/100,548, filed on Jan. 7, 2015, provisional application No. 61/935,899, filed on Feb. 5, 2014.

(52) U.S. Cl.
CPC .. *A61F 2/2436* (2013.01); *A61B 2017/00606* (2013.01); *A61B 2017/3425* (2013.01); *A61F 2/2457* (2013.01)

(56) References Cited

U.S. PATENT DOCUMENTS

| | | |
|---|---|---|
| 3,472,230 A | 10/1969 | Fogarty et al. |
| 3,476,101 A | 11/1969 | Ross |
| 3,548,417 A | 12/1970 | Kischer |
| 3,587,115 A | 6/1971 | Shiley |
| 3,657,744 A | 4/1972 | Ersek |
| 3,671,979 A | 6/1972 | Moulopoulos |
| 3,714,671 A | 2/1973 | Edwards et al. |
| 3,755,823 A | 9/1973 | Hancock |
| 3,976,079 A | 8/1976 | Samuels et al. |
| 4,003,382 A | 1/1977 | Dyke |
| 4,035,849 A | 7/1977 | Angell et al. |
| 4,056,854 A | 11/1977 | Boretos et al. |
| 4,073,438 A | 2/1978 | Meyer |
| 4,106,129 A | 8/1978 | Carpentier et al. |
| 4,222,126 A | 9/1980 | Boretos et al. |
| 4,265,694 A | 5/1981 | Boretos et al. |
| 4,297,749 A | 11/1981 | Davis et al. |
| 4,339,831 A | 7/1982 | Johnson |
| 4,343,048 A | 8/1982 | Ross et al. |
| 4,345,340 A | 8/1982 | Rosen |
| 4,373,216 A | 2/1983 | Klawitter |
| 4,406,022 A | 9/1983 | Roy |
| 4,470,157 A | 9/1984 | Love |
| 4,490,859 A | 1/1985 | Black et al. |
| 4,535,483 A | 8/1985 | Klawitter et al. |
| 4,574,803 A | 3/1986 | Storz |
| 4,585,705 A | 4/1986 | Broderick et al. |
| 4,592,340 A | 6/1986 | Boyles |
| 4,605,407 A | 8/1986 | Black et al. |
| 4,612,011 A | 9/1986 | Kautzky |
| 4,626,255 A | 12/1986 | Reichart et al. |
| 4,638,886 A | 1/1987 | Marietta |
| 4,643,732 A | 2/1987 | Pietsch et al. |
| 4,655,771 A | 4/1987 | Wallsten |
| 4,692,164 A | 9/1987 | Dzemeshkevich et al. |
| 4,733,665 A | 3/1988 | Palmaz |
| 4,759,758 A | 7/1988 | Gabbay |
| 4,762,128 A | 8/1988 | Rosenbluth |
| 4,777,951 A | 10/1988 | Cribier et al. |
| 4,787,899 A | 11/1988 | Lazarus |
| 4,787,901 A | 11/1988 | Baykut |
| 4,796,629 A | 1/1989 | Grayzel |
| 4,824,180 A | 4/1989 | Levrai |
| 4,829,990 A | 5/1989 | Thuroff et al. |
| 4,830,117 A | 5/1989 | Capasso |
| 4,851,001 A | 7/1989 | Faheri |
| 4,856,516 A | 8/1989 | Hillstead |
| 4,878,495 A | 11/1989 | Grayzel |
| 4,878,906 A | 11/1989 | Lindemann et al. |
| 4,883,458 A | 11/1989 | Shiber |
| 4,922,905 A | 5/1990 | Strecker |
| 4,923,013 A | 5/1990 | De Gennaro |
| 4,960,424 A | 10/1990 | Grooters |
| 4,966,604 A | 10/1990 | Reiss |
| 4,979,939 A | 12/1990 | Shiber |
| 4,986,830 A | 1/1991 | Owens et al. |
| 4,994,077 A | 2/1991 | Dobben |
| 4,996,873 A | 3/1991 | Takeuchi |
| 5,007,896 A | 4/1991 | Shiber |
| 5,026,366 A | 6/1991 | Leckrone |
| 5,032,128 A | 7/1991 | Alonso |
| 5,035,706 A | 7/1991 | Giantureo et al. |
| 5,037,434 A | 8/1991 | Lane |
| 5,047,041 A | 9/1991 | Samuels |
| 5,059,177 A | 10/1991 | Towne et al. |
| 5,064,435 A | 11/1991 | Porter |
| 5,080,668 A | 1/1992 | Bolz et al. |
| 5,085,635 A | 2/1992 | Cragg |
| 5,089,015 A | 2/1992 | Ross |
| 5,152,771 A | 10/1992 | Sabbaghian et al. |
| 5,163,953 A | 11/1992 | Vince |
| 5,167,628 A | 12/1992 | Boyles |
| 5,192,297 A | 3/1993 | Hull |
| 5,201,880 A | 4/1993 | Wright et al. |
| 5,266,073 A | 11/1993 | Wall |
| 5,282,847 A | 2/1994 | Trescony et al. |
| 5,295,958 A | 3/1994 | Shturman |
| 5,306,296 A | 4/1994 | Wright et al. |
| 5,332,402 A * | 7/1994 | Teitelbaum ........... A61F 2/2409 623/2.35 |
| 5,336,616 A | 8/1994 | Livesey et al. |
| 5,344,442 A | 9/1994 | Deac |
| 5,360,444 A | 11/1994 | Kusuhara |
| 5,364,407 A | 11/1994 | Poll |
| 5,370,685 A | 12/1994 | Stevens |
| 5,397,351 A | 3/1995 | Pavcnik et al. |
| 5,411,055 A | 5/1995 | Kane |
| 5,411,552 A | 5/1995 | Andersen et al. |
| 5,415,667 A | 5/1995 | Frater |
| 5,443,446 A | 8/1995 | Shturman |
| 5,480,424 A | 1/1996 | Cox |
| 5,500,014 A | 3/1996 | Quijano et al. |
| 5,545,209 A | 8/1996 | Roberts et al. |
| 5,545,214 A | 8/1996 | Stevens |
| 5,549,665 A | 8/1996 | Vesely et al. |
| 5,554,184 A | 9/1996 | Machiraju |
| 5,554,185 A | 9/1996 | Block et al. |
| 5,571,175 A | 11/1996 | Vanney et al. |
| 5,591,185 A | 1/1997 | Kilmer et al. |
| 5,607,462 A | 3/1997 | Imran |
| 5,607,464 A | 3/1997 | Trescony et al. |
| 5,609,626 A | 3/1997 | Quijano et al. |
| 5,639,274 A | 6/1997 | Fischell et al. |
| 5,662,704 A | 9/1997 | Gross |
| 5,665,115 A | 9/1997 | Cragg |
| 5,674,279 A | 10/1997 | Wright et al. |
| 5,697,905 A | 12/1997 | d'Ambrosio |
| 5,702,368 A | 12/1997 | Stevens et al. |
| 5,716,417 A | 2/1998 | Girard et al. |
| 5,728,068 A | 3/1998 | Leone et al. |
| 5,728,151 A | 3/1998 | Garrison et al. |
| 5,735,842 A | 4/1998 | Krueger et al. |
| 5,741,333 A | 4/1998 | Frid |
| 5,749,890 A | 5/1998 | Shaknovich |
| 5,756,476 A | 5/1998 | Epstein et al. |
| 5,769,812 A | 6/1998 | Stevens et al. |
| 5,792,179 A | 8/1998 | Sideris |
| 5,800,508 A | 9/1998 | Goicoechea et al. |
| 5,833,673 A | 11/1998 | Ockuly et al. |
| 5,840,081 A | 11/1998 | Andersen et al. |
| 5,855,597 A | 1/1999 | Jayaraman |
| 5,855,601 A | 1/1999 | Bessler et al. |
| 5,855,602 A | 1/1999 | Angell |
| 5,904,697 A | 5/1999 | Gifford, III et al. |
| 5,925,063 A | 7/1999 | Khosravi |
| 5,957,949 A | 9/1999 | Leonhardt et al. |
| 5,968,052 A | 10/1999 | Sullivan, III et al. |
| 5,968,068 A | 10/1999 | Dehdashtian et al. |
| 5,972,030 A | 10/1999 | Garrison et al. |
| 5,993,481 A | 11/1999 | Marcade et al. |
| 6,027,525 A | 2/2000 | Suh et al. |
| 6,042,607 A | 3/2000 | Williamson, IV et al. |
| 6,045,497 A | 4/2000 | Schweich, Jr. et al. |

(56) References Cited

U.S. PATENT DOCUMENTS

| | | | |
|---|---|---|---|
| 6,063,112 A | 5/2000 | Sgro |
| 6,077,214 A | 6/2000 | Mortier et al. |
| 6,099,508 A | 8/2000 | Bousquet |
| 6,132,473 A | 10/2000 | Williams et al. |
| 6,168,614 B1 | 1/2001 | Andersen et al. |
| 6,171,335 B1 | 1/2001 | Wheatley et al. |
| 6,174,327 B1 | 1/2001 | Mertens et al. |
| 6,183,411 B1 | 2/2001 | Mortier et al. |
| 6,210,408 B1 | 4/2001 | Chandrasekaran et al. |
| 6,217,585 B1 | 4/2001 | Houser et al. |
| 6,221,091 B1 | 4/2001 | Khosravi |
| 6,231,602 B1 | 5/2001 | Carpentier et al. |
| 6,245,102 B1 | 6/2001 | Jayaraman |
| 6,260,552 B1 | 7/2001 | Mortier et al. |
| 6,261,222 B1 | 7/2001 | Schweich, Jr. et al. |
| 6,264,602 B1 | 7/2001 | Mortier et al. |
| 6,287,339 B1 | 9/2001 | Vazquez et al. |
| 6,299,637 B1 | 10/2001 | Shaolian et al. |
| 6,302,906 B1 | 10/2001 | Goicoechea et al. |
| 6,312,465 B1 | 11/2001 | Griffin et al. |
| 6,332,893 B1 | 12/2001 | Mortier et al. |
| 6,350,277 B1 | 2/2002 | Kocur |
| 6,358,277 B1 | 3/2002 | Duran |
| 6,379,372 B1 | 4/2002 | Dehdashtian et al. |
| 6,402,679 B1 | 6/2002 | Mortier et al. |
| 6,402,680 B2 | 6/2002 | Mortier et al. |
| 6,402,781 B1 | 6/2002 | Langberg et al. |
| 6,406,420 B1 | 6/2002 | McCarthy et al. |
| 6,425,916 B1 | 7/2002 | Garrison et al. |
| 6,440,164 B1 | 8/2002 | DiMatteo et al. |
| 6,454,799 B1 | 9/2002 | Schreck |
| 6,458,153 B1 | 10/2002 | Bailey et al. |
| 6,461,382 B1 | 10/2002 | Cao |
| 6,468,660 B2 | 10/2002 | Ogle et al. |
| 6,482,228 B1 | 11/2002 | Norred |
| 6,488,704 B1 | 12/2002 | Connelly et al. |
| 6,537,198 B1 | 3/2003 | Vidlund et al. |
| 6,540,782 B1 | 4/2003 | Snyders |
| 6,569,196 B1 | 5/2003 | Vesely |
| 6,575,252 B2 | 6/2003 | Reed |
| 6,582,462 B1 | 6/2003 | Andersen et al. |
| 6,605,112 B1 | 8/2003 | Moll et al. |
| 6,616,684 B1 | 9/2003 | Vidlund et al. |
| 6,622,730 B2 | 9/2003 | Ekvall et al. |
| 6,629,534 B1 | 10/2003 | St. Goar et al. |
| 6,629,921 B1 | 10/2003 | Schweich, Jr. et al. |
| 6,648,077 B2 | 11/2003 | Hoffman |
| 6,648,921 B2 | 11/2003 | Anderson et al. |
| 6,652,578 B2 | 11/2003 | Bailey et al. |
| 6,669,724 B2 | 12/2003 | Park et al. |
| 6,706,065 B2 | 3/2004 | Langberg et al. |
| 6,709,456 B2 | 3/2004 | Langberg et al. |
| 6,723,038 B1 | 4/2004 | Schroeder et al. |
| 6,726,715 B2 | 4/2004 | Sutherland |
| 6,730,118 B2 | 5/2004 | Spenser et al. |
| 6,733,525 B2 | 5/2004 | Yang et al. |
| 6,740,105 B2 | 5/2004 | Yodfat et al. |
| 6,746,401 B2 | 6/2004 | Panescu |
| 6,746,471 B2 | 6/2004 | Mortier et al. |
| 6,752,813 B2 | 6/2004 | Goldfarb et al. |
| 6,764,510 B2 | 7/2004 | Vidlund et al. |
| 6,797,002 B2 | 9/2004 | Spence et al. |
| 6,810,882 B2 | 11/2004 | Langberg et al. |
| 6,830,584 B1 | 12/2004 | Seguin |
| 6,854,668 B2 | 2/2005 | Wancho et al. |
| 6,855,144 B2 | 2/2005 | Lesh |
| 6,858,001 B1 | 2/2005 | Aboul-Hosn |
| 6,890,353 B2 | 5/2005 | Cohn et al. |
| 6,893,460 B2 | 5/2005 | Spenser et al. |
| 6,896,690 B1 | 5/2005 | Lambrecht et al. |
| 6,908,424 B2 | 6/2005 | Mortier et al. |
| 6,908,481 B2 | 6/2005 | Cribier |
| 6,936,067 B2 | 8/2005 | Buchanan |
| 6,945,996 B2 | 9/2005 | Sedransk |
| 6,955,175 B2 | 10/2005 | Stevens et al. |
| 6,974,476 B2 | 12/2005 | McGuckin, Jr. et al. |
| 6,976,543 B1 | 12/2005 | Fischer |
| 6,997,950 B2 | 2/2006 | Chawla |
| 7,018,406 B2 | 3/2006 | Seguin et al. |
| 7,018,408 B2 | 3/2006 | Bailey et al. |
| 7,044,905 B2 | 5/2006 | Vidlund et al. |
| 7,060,021 B1 | 6/2006 | Wilk |
| 7,077,862 B2 | 7/2006 | Vidlund et al. |
| 7,087,064 B1 | 8/2006 | Hyde |
| 7,100,614 B2 | 9/2006 | Stevens et al. |
| 7,101,395 B2 * | 9/2006 | Tremulis ............ A61B 17/0401 623/2.11 |
| 7,108,717 B2 | 9/2006 | Freidberg |
| 7,112,219 B2 | 9/2006 | Vidlund et al. |
| 7,115,141 B2 | 10/2006 | Menz et al. |
| 7,141,064 B2 | 11/2006 | Scott et al. |
| 7,175,656 B2 | 2/2007 | Khairkhahan |
| 7,198,646 B2 | 4/2007 | Figulla et al. |
| 7,201,772 B2 | 4/2007 | Schwammenthal et al. |
| 7,247,134 B2 | 7/2007 | Vidlund et al. |
| 7,252,682 B2 | 8/2007 | Seguin |
| 7,267,686 B2 | 9/2007 | DiMatteo et al. |
| 7,275,604 B1 | 10/2007 | Wall |
| 7,276,078 B2 | 10/2007 | Spenser et al. |
| 7,276,084 B2 | 10/2007 | Yang et al. |
| 7,316,706 B2 | 1/2008 | Bloom et al. |
| 7,318,278 B2 | 1/2008 | Zhang et al. |
| 7,326,236 B2 | 2/2008 | Andreas et al. |
| 7,329,278 B2 | 2/2008 | Seguin et al. |
| 7,331,991 B2 | 2/2008 | Kheradvar et al. |
| 7,335,213 B1 | 2/2008 | Hyde et al. |
| 7,361,137 B2 | 4/2008 | Taylor et al. |
| 7,374,571 B2 | 5/2008 | Pease et al. |
| 7,377,941 B2 | 5/2008 | Rhee et al. |
| 7,381,210 B2 | 6/2008 | Zarbatany et al. |
| 7,381,218 B2 | 6/2008 | Schreck |
| 7,393,360 B2 | 7/2008 | Spenser et al. |
| 7,404,824 B1 | 7/2008 | Webler et al. |
| 7,416,554 B2 | 8/2008 | Lam et al. |
| 7,422,072 B2 | 9/2008 | Dade |
| 7,429,269 B2 | 9/2008 | Schwammenthal et al. |
| 7,442,204 B2 | 10/2008 | Schwammenthal et al. |
| 7,445,631 B2 | 11/2008 | Salahieh et al. |
| 7,462,191 B2 | 12/2008 | Spenser et al. |
| 7,470,285 B2 | 12/2008 | Nugent et al. |
| 7,500,989 B2 | 3/2009 | Solem et al. |
| 7,503,931 B2 | 3/2009 | Kowalsky et al. |
| 7,510,572 B2 | 3/2009 | Gabbay |
| 7,510,575 B2 | 3/2009 | Spenser et al. |
| 7,513,908 B2 | 4/2009 | Lattouf |
| 7,524,330 B2 | 4/2009 | Berreklouw |
| 7,527,647 B2 | 5/2009 | Spence |
| 7,534,260 B2 | 5/2009 | Lattouf |
| 7,556,646 B2 | 7/2009 | Yang et al. |
| 7,579,381 B2 | 8/2009 | Dove |
| 7,585,321 B2 | 9/2009 | Cribier |
| 7,591,847 B2 | 9/2009 | Navia et al. |
| 7,618,446 B2 | 11/2009 | Andersen et al. |
| 7,618,447 B2 | 11/2009 | Case et al. |
| 7,618,449 B2 * | 11/2009 | Tremulis ............ A61B 17/0401 623/2.11 |
| 7,621,948 B2 | 11/2009 | Herrmann et al. |
| 7,632,304 B2 | 12/2009 | Park |
| 7,632,308 B2 | 12/2009 | Loulmet |
| 7,635,386 B1 | 12/2009 | Gammie |
| 7,674,222 B2 | 3/2010 | Nikolic et al. |
| 7,674,286 B2 | 3/2010 | Alfieri et al. |
| 7,695,510 B2 | 4/2010 | Bloom et al. |
| 7,708,775 B2 | 5/2010 | Rowe et al. |
| 7,748,389 B2 | 7/2010 | Salahieh et al. |
| 7,766,961 B2 | 8/2010 | Patel et al. |
| 7,789,909 B2 | 9/2010 | Andersen et al. |
| 7,803,168 B2 | 9/2010 | Gifford et al. |
| 7,803,184 B2 | 9/2010 | McGuckin, Jr. et al. |
| 7,803,185 B2 | 9/2010 | Gabbay |
| 7,806,928 B2 | 10/2010 | Rowe et al. |
| 7,837,727 B2 | 11/2010 | Goetz et al. |
| 7,854,762 B2 | 12/2010 | Speziali et al. |
| 7,892,281 B2 | 2/2011 | Seguin et al. |

(56) References Cited

U.S. PATENT DOCUMENTS

| | | | |
|---|---|---|---|
| 7,896,915 B2 | 3/2011 | Guyenot et al. | |
| 7,901,454 B2 | 3/2011 | Kapadia et al. | |
| 7,927,370 B2 | 4/2011 | Webler et al. | |
| 7,931,630 B2 | 4/2011 | Nishtala et al. | |
| 7,942,928 B2 | 5/2011 | Webler et al. | |
| 7,955,247 B2 | 6/2011 | Levine et al. | |
| 7,955,385 B2 | 6/2011 | Crittenden | |
| 7,972,378 B2 | 7/2011 | Tabor et al. | |
| 3,007,992 A1 | 8/2011 | Tian et al. | |
| 7,988,727 B2 | 8/2011 | Santamore et al. | |
| 7,993,394 B2 | 8/2011 | Hariton et al. | |
| 8,029,556 B2 | 10/2011 | Rowe | |
| 8,043,368 B2 | 10/2011 | Crabtree | |
| 3,052,750 A1 | 11/2011 | Tuval et al. | |
| 8,052,749 B2 | 11/2011 | Salahieh et al. | |
| 8,052,751 B2 | 11/2011 | Aklog et al. | |
| 8,062,355 B2 | 11/2011 | Figulla et al. | |
| 8,062,359 B2 | 11/2011 | Marquez et al. | |
| 8,070,802 B2 | 12/2011 | Lamphere et al. | |
| 8,109,996 B2 | 2/2012 | Stacchino et al. | |
| 8,142,495 B2 | 3/2012 | Hasenkam et al. | |
| 8,152,821 B2 | 4/2012 | Gambale et al. | |
| 8,157,810 B2 | 4/2012 | Case et al. | |
| 8,167,932 B2 | 5/2012 | Bourang et al. | |
| 8,167,934 B2 | 5/2012 | Styrc et al. | |
| 8,187,299 B2 | 5/2012 | Goldfarb et al. | |
| 8,206,439 B2 | 6/2012 | Gomez Duran | |
| 8,216,301 B2 | 7/2012 | Bonhoeffer et al. | |
| 8,226,711 B2 | 7/2012 | Mortier et al. | |
| 8,236,045 B2 | 8/2012 | Benichou et al. | |
| 8,241,274 B2 | 8/2012 | Keogh et al. | |
| 8,252,051 B2 | 8/2012 | Chau et al. | |
| 8,303,653 B2 | 11/2012 | Bonhoeffer et al. | |
| 8,308,796 B2 | 11/2012 | Lashinski et al. | |
| 8,323,334 B2 | 12/2012 | Deem et al. | |
| 8,353,955 B2 | 1/2013 | Styrc et al. | |
| RE44,075 E | 3/2013 | Williamson et al. | |
| 8,449,599 B2 | 5/2013 | Chau et al. | |
| 8,454,656 B2 | 6/2013 | Tuval | |
| 8,470,028 B2 | 6/2013 | Thornton et al. | |
| 8,480,730 B2 | 7/2013 | Maurer et al. | |
| 8,486,138 B2 | 7/2013 | Vesely | |
| 8,506,623 B2 | 8/2013 | Wilson et al. | |
| 8,506,624 B2 | 8/2013 | Vidlund et al. | |
| 8,556,963 B2 * | 10/2013 | Tremulis | A61F 2/2445 623/2.11 |
| 8,578,705 B2 | 11/2013 | Sindano et al. | |
| 8,579,913 B2 | 11/2013 | Nielsen | |
| 8,591,573 B2 | 11/2013 | Barone | |
| 8,591,576 B2 | 11/2013 | Hasenkam et al. | |
| 8,597,347 B2 | 12/2013 | Maurer et al. | |
| 8,685,086 B2 | 4/2014 | Navia et al. | |
| 8,790,394 B2 | 7/2014 | Miller et al. | |
| 8,845,717 B2 | 9/2014 | Khairkhahan et al. | |
| 8,888,843 B2 | 11/2014 | Khairkhahan et al. | |
| 8,900,214 B2 | 12/2014 | Nance et al. | |
| 8,900,295 B2 | 12/2014 | Migliazza et al. | |
| 8,926,696 B2 | 1/2015 | Cabiri et al. | |
| 8,932,342 B2 | 1/2015 | McHugo et al. | |
| 8,932,348 B2 | 1/2015 | Solem et al. | |
| 8,945,208 B2 | 2/2015 | Jimenez et al. | |
| 8,956,407 B2 | 2/2015 | Macoviak et al. | |
| 8,961,597 B2 * | 2/2015 | Subramanian | A61F 2/2427 623/2.36 |
| 8,979,922 B2 | 3/2015 | Jayasinghe et al. | |
| 8,986,376 B2 | 3/2015 | Solem | |
| 9,011,522 B2 | 4/2015 | Annest | |
| 9,023,099 B2 | 5/2015 | Duffy et al. | |
| 9,034,032 B2 | 5/2015 | McLean et al. | |
| 9,034,033 B2 | 5/2015 | McLean et al. | |
| 9,039,757 B2 | 5/2015 | McLean et al. | |
| 9,039,759 B2 | 5/2015 | Alkhatib et al. | |
| 9,078,645 B2 | 7/2015 | Conklin et al. | |
| 9,078,749 B2 | 7/2015 | Lutter et al. | |
| 9,084,676 B2 | 7/2015 | Chau et al. | |
| 9,095,433 B2 | 8/2015 | Lutter et al. | |
| 9,125,742 B2 | 9/2015 | Yoganathan et al. | |
| 9,149,357 B2 | 10/2015 | Seguin | |
| 9,161,837 B2 | 10/2015 | Kapadia | |
| 9,168,137 B2 | 10/2015 | Subramanian et al. | |
| 9,232,995 B2 | 1/2016 | Kovalsky et al. | |
| 9,232,998 B2 | 1/2016 | Wilson et al. | |
| 9,232,999 B2 | 1/2016 | Maurer et al. | |
| 9,241,702 B2 | 1/2016 | Maisano et al. | |
| 9,254,192 B2 | 2/2016 | Lutter et al. | |
| 9,265,608 B2 | 2/2016 | Miller et al. | |
| 9,289,295 B2 | 3/2016 | Aklog et al. | |
| 9,289,297 B2 | 3/2016 | Wilson et al. | |
| 9,345,573 B2 | 5/2016 | Nyuli et al. | |
| 9,468,526 B2 * | 10/2016 | Subramanian | A61F 2/2436 |
| 9,480,557 B2 | 11/2016 | Pellegrini et al. | |
| 9,480,559 B2 | 11/2016 | Vidlund et al. | |
| 9,526,611 B2 | 12/2016 | Tegels et al. | |
| 9,597,181 B2 | 3/2017 | Christianson et al. | |
| 9,610,159 B2 | 4/2017 | Christianson et al. | |
| 9,675,454 B2 | 6/2017 | Vidlund et al. | |
| 9,730,792 B2 | 8/2017 | Lutter et al. | |
| 9,827,092 B2 * | 11/2017 | Vidlund | A61F 2/2439 |
| 9,833,315 B2 | 12/2017 | Vidlund et al. | |
| 9,848,880 B2 | 12/2017 | Coleman et al. | |
| 9,867,700 B2 | 1/2018 | Bakis et al. | |
| 9,883,941 B2 | 2/2018 | Hastings et al. | |
| 9,895,221 B2 | 2/2018 | Vidlund | |
| 9,986,993 B2 | 6/2018 | Vidlund et al. | |
| 10,016,271 B2 | 7/2018 | Morriss et al. | |
| 10,226,334 B2 | 3/2019 | Rowe et al. | |
| 10,327,894 B2 * | 6/2019 | Vidlund | A61F 2/2418 |
| 10,952,844 B2 * | 3/2021 | Vidlund | A61F 2/2418 |
| 2001/0018611 A1 | 8/2001 | Solem et al. | |
| 2001/0021872 A1 | 9/2001 | Bailey et al. | |
| 2001/0025171 A1 | 9/2001 | Mortier et al. | |
| 2002/0010427 A1 | 1/2002 | Scarfone et al. | |
| 2002/0116054 A1 | 8/2002 | Lundell et al. | |
| 2002/0139056 A1 | 10/2002 | Finnell | |
| 2002/0151961 A1 | 10/2002 | Lashinski et al. | |
| 2002/0161377 A1 | 10/2002 | Rabkin | |
| 2002/0173842 A1 | 11/2002 | Buchanan | |
| 2002/0183827 A1 | 12/2002 | Derus et al. | |
| 2003/0010509 A1 | 1/2003 | Hoffman | |
| 2003/0036698 A1 | 2/2003 | Kohler et al. | |
| 2003/0050694 A1 | 3/2003 | Yang et al. | |
| 2003/0069593 A1 * | 4/2003 | Tremulis | A61F 2/2445 606/142 |
| 2003/0078652 A1 | 4/2003 | Sutherland | |
| 2003/0100939 A1 | 5/2003 | Yodfat et al. | |
| 2003/0105519 A1 | 6/2003 | Fasol et al. | |
| 2003/0105520 A1 | 6/2003 | Alferness et al. | |
| 2003/0120340 A1 | 6/2003 | Liska et al. | |
| 2003/0130731 A1 | 7/2003 | Vidlund et al. | |
| 2003/0149476 A1 | 8/2003 | Damm et al. | |
| 2003/0212454 A1 | 11/2003 | Scott et al. | |
| 2004/0039436 A1 | 2/2004 | Spenser et al. | |
| 2004/0049211 A1 * | 3/2004 | Tremulis | A61F 2/2487 606/153 |
| 2004/0049266 A1 | 3/2004 | Anduiza et al. | |
| 2004/0064014 A1 | 4/2004 | Melvin et al. | |
| 2004/0092858 A1 | 5/2004 | Wilson et al. | |
| 2004/0093075 A1 | 5/2004 | Kuehne | |
| 2004/0097865 A1 | 5/2004 | Anderson et al. | |
| 2004/0127983 A1 | 7/2004 | Mortier et al. | |
| 2004/0133263 A1 | 7/2004 | Dusbabek et al. | |
| 2004/0147958 A1 | 7/2004 | Lam et al. | |
| 2004/0152947 A1 | 8/2004 | Schroeder et al. | |
| 2004/0162610 A1 | 8/2004 | Liska et al. | |
| 2004/0163828 A1 | 8/2004 | Silverstein et al. | |
| 2004/0181239 A1 | 9/2004 | Dorn et al. | |
| 2004/0186565 A1 | 9/2004 | Schreck | |
| 2004/0186566 A1 | 9/2004 | Hindrichs et al. | |
| 2004/0210304 A1 * | 10/2004 | Seguin | A61F 2/2427 623/2.11 |
| 2004/0260317 A1 | 12/2004 | Bloom et al. | |
| 2004/0260389 A1 | 12/2004 | Case et al. | |
| 2005/0004652 A1 | 1/2005 | van der Burg et al. | |
| 2005/0004666 A1 | 1/2005 | Altieri et al. | |

(56) References Cited

U.S. PATENT DOCUMENTS

| | | |
|---|---|---|
| 2005/0075727 A1 | 4/2005 | Wheatley |
| 2005/0080402 A1 | 4/2005 | Santamore et al. |
| 2005/0085900 A1 | 4/2005 | Case et al. |
| 2005/0096498 A1 | 5/2005 | Houser et al. |
| 2005/0107661 A1 | 5/2005 | Lau et al. |
| 2005/0113798 A1 | 5/2005 | Slater et al. |
| 2005/0113810 A1 | 5/2005 | Houser et al. |
| 2005/0113811 A1 | 5/2005 | Houser et al. |
| 2005/0119519 A9 | 6/2005 | Girard et al. |
| 2005/0121206 A1 | 6/2005 | Dolan |
| 2005/0125012 A1 | 6/2005 | Houser et al. |
| 2005/0137686 A1 | 6/2005 | Salahieh et al. |
| 2005/0137688 A1 | 6/2005 | Salahieh et al. |
| 2005/0137695 A1 | 6/2005 | Salahieh et al. |
| 2005/0137698 A1 | 6/2005 | Salahieh et al. |
| 2005/0148815 A1 | 7/2005 | Mortier et al. |
| 2005/0177180 A1 | 8/2005 | Kaganov et al. |
| 2005/0197695 A1 | 9/2005 | Stacchino et al. |
| 2005/0203614 A1 | 9/2005 | Forster et al. |
| 2005/0203615 A1 | 9/2005 | Forster et al. |
| 2005/0203617 A1 | 9/2005 | Forster et al. |
| 2005/0234546 A1 | 10/2005 | Nugent et al. |
| 2005/0240200 A1 | 10/2005 | Bergheim |
| 2005/0251209 A1 | 11/2005 | Saadat et al. |
| 2005/0256567 A1 | 11/2005 | Lim et al. |
| 2005/0283231 A1 | 12/2005 | Haug et al. |
| 2005/0288766 A1 | 12/2005 | Plain et al. |
| 2006/0004442 A1 | 1/2006 | Spenser et al. |
| 2006/0025784 A1 | 2/2006 | Starksen et al. |
| 2006/0025857 A1 | 2/2006 | Bergheim et al. |
| 2006/0030885 A1 | 2/2006 | Hyde |
| 2006/0042803 A1 | 3/2006 | Gallaher |
| 2006/0047338 A1 | 3/2006 | Jenson et al. |
| 2006/0052868 A1 | 3/2006 | Mortier et al. |
| 2006/0058872 A1 | 3/2006 | Salahieh et al. |
| 2006/0074484 A1* | 4/2006 | Huber .............. A61F 2/013 623/2.11 |
| 2006/0094983 A1 | 5/2006 | Burbank et al. |
| 2006/0129025 A1 | 6/2006 | Levine et al. |
| 2006/0142784 A1 | 6/2006 | Kontos |
| 2006/0161040 A1 | 7/2006 | McCarthy et al. |
| 2006/0161249 A1 | 7/2006 | Realyvasquez et al. |
| 2006/0167541 A1 | 7/2006 | Lattouf |
| 2006/0195134 A1 | 8/2006 | Crittenden |
| 2006/0195183 A1 | 8/2006 | Navia et al. |
| 2006/0229708 A1 | 10/2006 | Powell et al. |
| 2006/0229719 A1 | 10/2006 | Marquez et al. |
| 2006/0241745 A1 | 10/2006 | Solem |
| 2006/0247491 A1 | 11/2006 | Vidlund et al. |
| 2006/0252984 A1 | 11/2006 | Rahdert et al. |
| 2006/0259135 A1 | 11/2006 | Navia et al. |
| 2006/0259136 A1 | 11/2006 | Nguyen et al. |
| 2006/0259137 A1 | 11/2006 | Artof et al. |
| 2006/0276874 A1 | 12/2006 | Wilson et al. |
| 2006/0282161 A1 | 12/2006 | Huynh et al. |
| 2006/0287716 A1 | 12/2006 | Banbury et al. |
| 2006/0287717 A1 | 12/2006 | Rowe et al. |
| 2007/0005131 A1 | 1/2007 | Taylor |
| 2007/0005231 A1 | 1/2007 | Seguchi |
| 2007/0010877 A1 | 1/2007 | Salahieh et al. |
| 2007/0016286 A1 | 1/2007 | Herrmann et al. |
| 2007/0016288 A1 | 1/2007 | Gurskis et al. |
| 2007/0027535 A1 | 2/2007 | Purdy et al. |
| 2007/0038291 A1 | 2/2007 | Case et al. |
| 2007/0050020 A1 | 3/2007 | Spence |
| 2007/0061010 A1 | 3/2007 | Hauser et al. |
| 2007/0066863 A1 | 3/2007 | Rafiee et al. |
| 2007/0073387 A1 | 3/2007 | Forster et al. |
| 2007/0078297 A1 | 4/2007 | Rafiee et al. |
| 2007/0083076 A1 | 4/2007 | Lichtenstein |
| 2007/0083259 A1 | 4/2007 | Bloom et al. |
| 2007/0093890 A1 | 4/2007 | Eliasen et al. |
| 2007/0100439 A1 | 5/2007 | Cangialosi et al. |
| 2007/0112422 A1 | 5/2007 | Dehdashtian |
| 2007/0112425 A1 | 5/2007 | Schaller et al. |
| 2007/0118151 A1 | 5/2007 | Davidson |
| 2007/0118154 A1 | 5/2007 | Crabtree |
| 2007/0118210 A1 | 5/2007 | Pinchuk |
| 2007/0118213 A1 | 5/2007 | Loulmet |
| 2007/0142906 A1 | 6/2007 | Figulla et al. |
| 2007/0161846 A1 | 7/2007 | Nikolic et al. |
| 2007/0162048 A1 | 7/2007 | Quinn et al. |
| 2007/0162103 A1 | 7/2007 | Case et al. |
| 2007/0168024 A1 | 7/2007 | Khairkhahan |
| 2007/0173931 A1* | 7/2007 | Tremulis .............. A61F 2/2487 606/139 |
| 2007/0185565 A1 | 8/2007 | Schwammenthal et al. |
| 2007/0185571 A1 | 8/2007 | Kapadia et al. |
| 2007/0203575 A1 | 8/2007 | Forster et al. |
| 2007/0213813 A1 | 9/2007 | Von Segesser et al. |
| 2007/0215362 A1 | 9/2007 | Rodgers |
| 2007/0221388 A1 | 9/2007 | Johnson |
| 2007/0233239 A1 | 10/2007 | Navia et al. |
| 2007/0239265 A1 | 10/2007 | Birdsall |
| 2007/0256843 A1 | 11/2007 | Pahila |
| 2007/0265658 A1 | 11/2007 | Nelson et al. |
| 2007/0267202 A1 | 11/2007 | Mariller |
| 2007/0270932 A1 | 11/2007 | Headley et al. |
| 2007/0270943 A1 | 11/2007 | Solem et al. |
| 2007/0293944 A1 | 12/2007 | Spenser et al. |
| 2008/0009940 A1 | 1/2008 | Cribier |
| 2008/0033543 A1 | 2/2008 | Gurskis et al. |
| 2008/0065011 A1 | 3/2008 | Marchand et al. |
| 2008/0071361 A1 | 3/2008 | Tuval et al. |
| 2008/0071362 A1 | 3/2008 | Tuval et al. |
| 2008/0071363 A1 | 3/2008 | Tuval et al. |
| 2008/0071366 A1 | 3/2008 | Tuval et al. |
| 2008/0071368 A1 | 3/2008 | Tuval et al. |
| 2008/0071369 A1 | 3/2008 | Tuval et al. |
| 2008/0082163 A1 | 4/2008 | Woo |
| 2008/0082166 A1 | 4/2008 | Styrc et al. |
| 2008/0091264 A1 | 4/2008 | Machold et al. |
| 2008/0109069 A1* | 5/2008 | Coleman .............. A61M 27/002 623/1.25 |
| 2008/0114442 A1 | 5/2008 | Mitchell et al. |
| 2008/0125861 A1 | 5/2008 | Webler et al. |
| 2008/0140189 A1* | 6/2008 | Nguyen .............. A61F 2/2412 623/2.11 |
| 2008/0147179 A1 | 6/2008 | Cai et al. |
| 2008/0154355 A1 | 6/2008 | Benichou et al. |
| 2008/0154356 A1 | 6/2008 | Obermiller et al. |
| 2008/0161911 A1 | 7/2008 | Revuelta et al. |
| 2008/0172035 A1 | 7/2008 | Starksen et al. |
| 2008/0177381 A1 | 7/2008 | Navia et al. |
| 2008/0183203 A1 | 7/2008 | Fitzgerald et al. |
| 2008/0183273 A1 | 7/2008 | Mesana et al. |
| 2008/0188928 A1 | 8/2008 | Salahieh et al. |
| 2008/0208328 A1 | 8/2008 | Antocci et al. |
| 2008/0208332 A1 | 8/2008 | Lamphere et al. |
| 2008/0221672 A1 | 9/2008 | Lamphere et al. |
| 2008/0228263 A1* | 9/2008 | Ryan .............. A61F 2/2418 623/2.11 |
| 2008/0243150 A1 | 10/2008 | Starksen et al. |
| 2008/0243245 A1* | 10/2008 | Thambar .............. A61F 2/2409 623/2.11 |
| 2008/0255660 A1 | 10/2008 | Guyenot et al. |
| 2008/0255661 A1 | 10/2008 | Straubinger et al. |
| 2008/0281411 A1 | 11/2008 | Berreklouw |
| 2008/0288060 A1 | 11/2008 | Kaye et al. |
| 2008/0293996 A1 | 11/2008 | Evans et al. |
| 2008/0300678 A1* | 12/2008 | Eidenschink ........ A61F 2/2418 623/2.18 |
| 2009/0005863 A1 | 1/2009 | Goetz et al. |
| 2009/0048668 A1 | 2/2009 | Wilson et al. |
| 2009/0054968 A1 | 2/2009 | Bonhoeffer et al. |
| 2009/0054974 A1 | 2/2009 | McGuckin, Jr. et al. |
| 2009/0062908 A1 | 3/2009 | Bonhoeffer et al. |
| 2009/0076598 A1 | 3/2009 | Salahieh et al. |
| 2009/0082619 A1 | 3/2009 | De Marchena |
| 2009/0088836 A1 | 4/2009 | Bishop et al. |
| 2009/0099410 A1 | 4/2009 | De Marchena |
| 2009/0112309 A1 | 4/2009 | Jaramillo et al. |
| 2009/0131849 A1 | 5/2009 | Maurer et al. |
| 2009/0132035 A1 | 5/2009 | Roth et al. |

(56) References Cited

U.S. PATENT DOCUMENTS

| | | |
|---|---|---|
| 2009/0137861 A1 | 5/2009 | Goldberg et al. |
| 2009/0138079 A1 | 5/2009 | Tuval et al. |
| 2009/0157175 A1 | 6/2009 | Benichou |
| 2009/0164005 A1 | 6/2009 | Dove et al. |
| 2009/0171432 A1 | 7/2009 | Von Segesser et al. |
| 2009/0171447 A1 | 7/2009 | Von Segesser et al. |
| 2009/0171456 A1 | 7/2009 | Kveen et al. |
| 2009/0177266 A1 | 7/2009 | Powell et al. |
| 2009/0182417 A1* | 7/2009 | Tremulis ............ A61B 17/0401 623/2.11 |
| 2009/0192601 A1 | 7/2009 | Rafiee et al. |
| 2009/0210047 A1* | 8/2009 | Amplatz ................ A61F 2/07 623/1.12 |
| 2009/0210052 A1 | 8/2009 | Forster et al. |
| 2009/0216322 A1 | 8/2009 | Le et al. |
| 2009/0222076 A1 | 9/2009 | Figulla et al. |
| 2009/0224529 A1 | 9/2009 | Gill |
| 2009/0234318 A1 | 9/2009 | Loulmet et al. |
| 2009/0234435 A1 | 9/2009 | Johnson et al. |
| 2009/0234443 A1 | 9/2009 | Ottma et al. |
| 2009/0240320 A1 | 9/2009 | Tuval et al. |
| 2009/0248149 A1 | 10/2009 | Gabbay |
| 2009/0276038 A1* | 11/2009 | Tremulis ............ A61B 17/0401 623/2.11 |
| 2009/0276040 A1* | 11/2009 | Rowe .................. A61F 2/2454 623/2.18 |
| 2009/0281619 A1 | 11/2009 | Le et al. |
| 2009/0287299 A1 | 11/2009 | Fabor et al. |
| 2009/0292262 A1 | 11/2009 | Adams et al. |
| 2009/0319037 A1 | 12/2009 | Rowe et al. |
| 2009/0326575 A1 | 12/2009 | Galdonik et al. |
| 2010/0004740 A1* | 1/2010 | Seguin ................ A61F 2/2433 623/2.18 |
| 2010/0016958 A1 | 1/2010 | St. Goar et al. |
| 2010/0021382 A1 | 1/2010 | Dorshow et al. |
| 2010/0023117 A1 | 1/2010 | Yoganathan et al. |
| 2010/0036479 A1 | 2/2010 | Hill et al. |
| 2010/0049313 A1 | 2/2010 | Alon et al. |
| 2010/0082094 A1 | 4/2010 | Quadri et al. |
| 2010/0121435 A1* | 5/2010 | Subramanian ........ A61F 2/2427 623/2.11 |
| 2010/0121437 A1* | 5/2010 | Subramanian ........ A61F 2/2466 623/2.36 |
| 2010/0161041 A1 | 6/2010 | Maisano et al. |
| 2010/0168839 A1 | 7/2010 | Braido et al. |
| 2010/0179641 A1 | 7/2010 | Ryan et al. |
| 2010/0185277 A1 | 7/2010 | Braido et al. |
| 2010/0185278 A1 | 7/2010 | Schankereli |
| 2010/0191326 A1 | 7/2010 | Alkhatib |
| 2010/0192402 A1 | 8/2010 | Yamaguchi et al. |
| 2010/0204781 A1 | 8/2010 | Alkhatib |
| 2010/0210899 A1 | 8/2010 | Schankereli |
| 2010/0217382 A1 | 8/2010 | Chau et al. |
| 2010/0249489 A1 | 9/2010 | Jarvik |
| 2010/0249923 A1 | 9/2010 | Alkhatib et al. |
| 2010/0280589 A1 | 11/2010 | Styrc |
| 2010/0280604 A1 | 11/2010 | Zipory et al. |
| 2010/0286768 A1 | 11/2010 | Alkhatib |
| 2010/0298755 A1 | 11/2010 | McNamara et al. |
| 2010/0298931 A1 | 11/2010 | Quadri et al. |
| 2011/0004296 A1 | 1/2011 | Lutter et al. |
| 2011/0015616 A1* | 1/2011 | Straubinger ....... A61M 25/0147 604/528 |
| 2011/0015728 A1 | 1/2011 | Jimenez et al. |
| 2011/0015729 A1 | 1/2011 | Jimenez et al. |
| 2011/0022157 A1* | 1/2011 | Essinger .................. A61F 2/24 623/1.26 |
| 2011/0029072 A1 | 2/2011 | Gabbay |
| 2011/0066231 A1 | 3/2011 | Cartledge et al. |
| 2011/0066233 A1 | 3/2011 | Thornton et al. |
| 2011/0112632 A1 | 5/2011 | Chau et al. |
| 2011/0137397 A1 | 6/2011 | Chau et al. |
| 2011/0137408 A1 | 6/2011 | Bergheim |
| 2011/0213459 A1* | 9/2011 | Garrison .................. A61F 2/24 623/2.11 |
| 2011/0218619 A1 | 9/2011 | Benichou et al. |
| 2011/0224655 A1 | 9/2011 | Asirvatham et al. |
| 2011/0224678 A1 | 9/2011 | Gabbay |
| 2011/0224728 A1 | 9/2011 | Martin et al. |
| 2011/0224784 A1 | 9/2011 | Quinn |
| 2011/0245911 A1 | 10/2011 | Quill et al. |
| 2011/0251682 A1 | 10/2011 | Murray, III et al. |
| 2011/0264191 A1 | 10/2011 | Rothstein |
| 2011/0264206 A1 | 10/2011 | Tabor |
| 2011/0288637 A1 | 11/2011 | De Marchena |
| 2011/0319988 A1 | 12/2011 | Schankereli et al. |
| 2011/0319989 A1* | 12/2011 | Lane .................. A61F 2/2418 623/2.11 |
| 2012/0010694 A1 | 1/2012 | Lutter et al. |
| 2012/0010700 A1* | 1/2012 | Spenser ................ A61F 2/2463 623/2.36 |
| 2012/0016468 A1 | 1/2012 | Robin et al. |
| 2012/0022640 A1 | 1/2012 | Gross et al. |
| 2012/0035703 A1 | 2/2012 | Lutter et al. |
| 2012/0035713 A1 | 2/2012 | Lutter et al. |
| 2012/0035722 A1 | 2/2012 | Tuval |
| 2012/0053686 A1 | 3/2012 | McNamara et al. |
| 2012/0059487 A1 | 3/2012 | Cunanan et al. |
| 2012/0089171 A1 | 4/2012 | Hastings et al. |
| 2012/0101571 A1* | 4/2012 | Thambar ............ A61F 2/2436 623/2.17 |
| 2012/0101572 A1 | 4/2012 | Kovalsky et al. |
| 2012/0109079 A1* | 5/2012 | Asleson ................ A61F 2/2427 604/272 |
| 2012/0116351 A1 | 5/2012 | Chomas et al. |
| 2012/0123529 A1 | 5/2012 | Levi et al. |
| 2012/0158129 A1 | 6/2012 | Duffy et al. |
| 2012/0165930 A1 | 6/2012 | Gifford, III et al. |
| 2012/0179244 A1 | 7/2012 | Schankereli et al. |
| 2012/0203336 A1 | 8/2012 | Annest |
| 2012/0215303 A1 | 8/2012 | Quadri et al. |
| 2012/0226348 A1 | 9/2012 | Lane et al. |
| 2012/0245678 A1* | 9/2012 | Solem .................. A61F 2/2409 623/2.36 |
| 2012/0283824 A1 | 11/2012 | Lutter et al. |
| 2012/0289945 A1 | 11/2012 | Segermark |
| 2013/0030522 A1 | 1/2013 | Rowe et al. |
| 2013/0053950 A1 | 2/2013 | Rowe et al. |
| 2013/0066341 A1 | 3/2013 | Ketai et al. |
| 2013/0079873 A1 | 3/2013 | Migliazza et al. |
| 2013/0103140 A1* | 4/2013 | Subramanian ........ A61F 2/2445 623/2.1 |
| 2013/0131788 A1 | 5/2013 | Quadri et al. |
| 2013/0172978 A1* | 7/2013 | Vidlund ................ A61F 2/2418 623/1.12 |
| 2013/0184811 A1 | 7/2013 | Rowe et al. |
| 2013/0190860 A1 | 7/2013 | Sundt, III |
| 2013/0190861 A1 | 7/2013 | Chau et al. |
| 2013/0197622 A1 | 8/2013 | Mitra et al. |
| 2013/0226288 A1 | 8/2013 | Goldwasser et al. |
| 2013/0226290 A1* | 8/2013 | Yellin .................. A61F 2/2427 623/2.11 |
| 2013/0231735 A1 | 9/2013 | Deem et al. |
| 2013/0274874 A1 | 10/2013 | Hammer |
| 2013/0282101 A1 | 10/2013 | Eidenschink et al. |
| 2013/0304200 A1* | 11/2013 | McLean ................ A61F 2/2436 623/2.18 |
| 2013/0310928 A1 | 11/2013 | Morriss et al. |
| 2013/0317603 A1 | 11/2013 | McLean et al. |
| 2013/0325041 A1 | 12/2013 | Annest et al. |
| 2013/0325110 A1 | 12/2013 | Khalil et al. |
| 2013/0338752 A1 | 12/2013 | Geusen et al. |
| 2013/0338764 A1* | 12/2013 | Thornton ............ A61B 17/0401 623/2.11 |
| 2014/0005778 A1* | 1/2014 | Buchbinder .......... A61F 2/2412 623/2.18 |
| 2014/0031924 A1 | 1/2014 | Bruchman et al. |
| 2014/0046433 A1 | 2/2014 | Kovalsky |
| 2014/0081323 A1 | 3/2014 | Hawkins |
| 2014/0094918 A1 | 4/2014 | Vishnubholta et al. |
| 2014/0142691 A1 | 5/2014 | Pouletty |

(56) References Cited

U.S. PATENT DOCUMENTS

| | | |
|---|---|---|
| 2014/0163668 A1 | 6/2014 | Rafiee |
| 2014/0194981 A1 | 7/2014 | Menk et al. |
| 2014/0194983 A1 | 7/2014 | Kovalsky et al. |
| 2014/0214159 A1* | 7/2014 | Vidlund .............. A61L 27/3625 623/2.14 |
| 2014/0222142 A1 | 8/2014 | Kovalsky et al. |
| 2014/0243965 A1* | 8/2014 | Benson ................. A61F 2/2436 623/2.18 |
| 2014/0243966 A1 | 8/2014 | Garde et al. |
| 2014/0257466 A1* | 9/2014 | Board ................... A61F 2/2418 623/2.11 |
| 2014/0277419 A1 | 9/2014 | Garde et al. |
| 2014/0296969 A1 | 10/2014 | Tegels et al. |
| 2014/0296970 A1 | 10/2014 | Ekvall et al. |
| 2014/0296971 A1 | 10/2014 | Tegels et al. |
| 2014/0296972 A1 | 10/2014 | Tegels et al. |
| 2014/0296975 A1 | 10/2014 | Tegels et al. |
| 2014/0303718 A1 | 10/2014 | Tegels et al. |
| 2014/0309732 A1 | 10/2014 | Solem |
| 2014/0316516 A1 | 10/2014 | Vidlund et al. |
| 2014/0324160 A1 | 10/2014 | Benichou et al. |
| 2014/0324161 A1 | 10/2014 | Tegels et al. |
| 2014/0324164 A1 | 10/2014 | Gross et al. |
| 2014/0331475 A1 | 11/2014 | Duffy et al. |
| 2014/0358222 A1* | 12/2014 | Gorman, III .......... A61F 2/2418 623/2.11 |
| 2014/0358224 A1 | 12/2014 | Tegels et al. |
| 2014/0364942 A1 | 12/2014 | Straubinger et al. |
| 2014/0364944 A1 | 12/2014 | Lutter et al. |
| 2014/0379076 A1 | 12/2014 | Vidlund et al. |
| 2015/0005874 A1* | 1/2015 | Vidlund ................ A61F 2/2412 623/2.14 |
| 2015/0011821 A1 | 1/2015 | Gorman et al. |
| 2015/0025553 A1 | 1/2015 | Del Nido et al. |
| 2015/0057705 A1 | 2/2015 | Vidlund |
| 2015/0073542 A1 | 3/2015 | Heldman |
| 2015/0073545 A1 | 3/2015 | Braido |
| 2015/0094802 A1 | 4/2015 | Buchbinder et al. |
| 2015/0105856 A1 | 4/2015 | Rowe et al. |
| 2015/0119936 A1 | 4/2015 | Gilmore et al. |
| 2015/0119978 A1 | 4/2015 | Tegels et al. |
| 2015/0127093 A1 | 5/2015 | Hosmer et al. |
| 2015/0127096 A1 | 5/2015 | Rowe et al. |
| 2015/0134050 A1 | 5/2015 | Solem et al. |
| 2015/0142100 A1 | 5/2015 | Morriss et al. |
| 2015/0142101 A1 | 5/2015 | Coleman et al. |
| 2015/0142103 A1 | 5/2015 | Vidlund |
| 2015/0142104 A1 | 5/2015 | Braido |
| 2015/0173897 A1 | 6/2015 | Raanani et al. |
| 2015/0196393 A1 | 7/2015 | Vidlund et al. |
| 2015/0196688 A1 | 7/2015 | James |
| 2015/0202044 A1 | 7/2015 | Chau et al. |
| 2015/0216653 A1 | 8/2015 | Freudenthal |
| 2015/0216660 A1 | 8/2015 | Pintor |
| 2015/0223820 A1 | 8/2015 | Olson |
| 2015/0223934 A1 | 8/2015 | Vidlund et al. |
| 2015/0223935 A1* | 8/2015 | Subramanian ........ A61F 2/2436 623/2.11 |
| 2015/0238312 A1 | 8/2015 | Lashinski |
| 2015/0238729 A1 | 8/2015 | Jenson et al. |
| 2015/0272731 A1 | 10/2015 | Racchini et al. |
| 2015/0305860 A1 | 10/2015 | Wang et al. |
| 2015/0305864 A1 | 10/2015 | Quadri et al. |
| 2015/0305868 A1 | 10/2015 | Lutter et al. |
| 2015/0327995 A1 | 11/2015 | Morin et al. |
| 2015/0328001 A1 | 11/2015 | McLean |
| 2015/0335424 A1 | 11/2015 | McLean |
| 2015/0335429 A1 | 11/2015 | Morriss et al. |
| 2015/0342717 A1 | 12/2015 | O'Donnell et al. |
| 2015/0351903 A1 | 12/2015 | Morriss et al. |
| 2015/0351906 A1 | 12/2015 | Hammer et al. |
| 2016/0000562 A1 | 1/2016 | Siegel |
| 2016/0008131 A1 | 1/2016 | Christianson et al. |
| 2016/0067042 A1 | 3/2016 | Murad et al. |
| 2016/0074160 A1 | 3/2016 | Christianson et al. |
| 2016/0106537 A1 | 4/2016 | Christianson et al. |
| 2016/0113764 A1 | 4/2016 | Sheahan |
| 2016/0120673 A1* | 5/2016 | Siegel ..................... A61F 2/962 623/1.23 |
| 2016/0143736 A1 | 5/2016 | Vidlund |
| 2016/0151155 A1 | 6/2016 | Lutter et al. |
| 2016/0206280 A1 | 7/2016 | Vidlund et al. |
| 2016/0242902 A1 | 8/2016 | Morriss |
| 2016/0262879 A1 | 9/2016 | Meiri et al. |
| 2016/0262881 A1 | 9/2016 | Schankereli et al. |
| 2016/0278955 A1 | 9/2016 | Liu et al. |
| 2016/0317290 A1 | 11/2016 | Chau |
| 2016/0324635 A1* | 11/2016 | Vidlund ............. A61B 17/0057 |
| 2016/0331527 A1 | 11/2016 | Vidlund et al. |
| 2016/0346086 A1 | 12/2016 | Solem |
| 2016/0367365 A1 | 12/2016 | Conklin |
| 2016/0367367 A1 | 12/2016 | Maisano et al. |
| 2016/0367368 A1 | 12/2016 | Vidlund et al. |
| 2017/0071733 A1* | 3/2017 | Ghione ................. A61F 2/2418 |
| 2017/0079790 A1* | 3/2017 | Vidlund ............. A61B 17/0401 |
| 2017/0100245 A1* | 4/2017 | Subramanian ........ A61F 2/2445 |
| 2017/0100248 A1 | 4/2017 | Tegels et al. |
| 2017/0128208 A1 | 5/2017 | Christianson et al. |
| 2017/0181854 A1 | 6/2017 | Christianson et al. |
| 2017/0196688 A1 | 7/2017 | Christianson et al. |
| 2017/0252153 A1 | 9/2017 | Chau et al. |
| 2017/0266001 A1 | 9/2017 | Vidlund et al. |
| 2017/0281343 A1 | 10/2017 | Christianson et al. |
| 2017/0312076 A1 | 11/2017 | Lutter et al. |
| 2017/0312077 A1 | 11/2017 | Vidlund et al. |
| 2017/0319333 A1 | 11/2017 | Tegels et al. |
| 2017/0325842 A1* | 11/2017 | Siegel ................... A61F 2/2427 |
| 2018/0028314 A1 | 2/2018 | Ekvall et al. |
| 2018/0078368 A1 | 3/2018 | Vidlund et al. |
| 2018/0078370 A1 | 3/2018 | Kovalsky et al. |
| 2018/0147055 A1 | 5/2018 | Vidlund et al. |
| 2018/0193138 A1 | 7/2018 | Vidlund |

FOREIGN PATENT DOCUMENTS

| | | |
|---|---|---|
| CN | 2902226 Y | 5/2007 |
| CN | 101146484 A | 3/2008 |
| CN | 101180010 A | 5/2008 |
| CN | 101180010 | 12/2010 |
| CN | 101984938 A | 3/2011 |
| CN | 102639179 A | 8/2012 |
| CN | 102791223 A | 11/2012 |
| CN | 102869317 A | 1/2013 |
| CN | 102869318 A | 1/2013 |
| CN | 102869321 A | 1/2013 |
| CN | 103220993 A | 7/2013 |
| CN | 103974674 A | 8/2014 |
| CN | 102639179 B | 10/2014 |
| DE | 2246526 A1 | 3/1973 |
| DE | 19532846 A1 | 3/1997 |
| DE | 19546692 A1 | 6/1997 |
| DE | 19857887 A1 | 7/2000 |
| DE | 19907646 A1 | 8/2000 |
| DE | 10049812 A1 | 4/2002 |
| DE | 10049813 C1 | 4/2002 |
| DE | 10049815 A1 | 4/2002 |
| DE | 102006052564 B3 | 12/2007 |
| DE | 102006052710 A1 | 5/2008 |
| DE | 102007043830 A1 | 4/2009 |
| DE | 102007043831 A1 | 4/2009 |
| EP | 0103546 A1 | 3/1984 |
| EP | 1057460 A1 | 12/2000 |
| EP | 1088529 A2 | 4/2001 |
| EP | 1469797 | 10/2004 |
| EP | 1469797 B1 | 11/2005 |
| EP | 2111800 A1 | 10/2009 |
| EP | 2193762 A1 | 6/2010 |
| EP | 2278944 A2 | 2/2011 |
| EP | 2747707 A1 | 7/2014 |
| EP | 2918248 A1 | 9/2015 |
| FR | 2788217 A1 | 7/2000 |
| FR | 2815844 A1 | 5/2002 |
| JP | 2003505146 A | 2/2003 |

(56) References Cited

FOREIGN PATENT DOCUMENTS

| | | |
|---|---|---|
| JP | 2005515836 A | 6/2005 |
| JP | 2009514628 A | 4/2009 |
| JP | 2009519783 A | 5/2009 |
| JP | 2010517623 A | 5/2010 |
| JP | 2013512765 A | 4/2013 |
| JP | 2014532457 A | 12/2014 |
| NL | 1017275 C2 | 8/2002 |
| SU | 1271508 A1 | 11/1986 |
| WO | 9217118 A1 | 10/1992 |
| WO | 9301768 A1 | 2/1993 |
| WO | 9829057 | 7/1998 |
| WO | 9940964 A1 | 8/1999 |
| WO | 9947075 A1 | 9/1999 |
| WO | 2000018333 A1 | 4/2000 |
| WO | 2000030550 A1 | 6/2000 |
| WO | 2000041652 | 7/2000 |
| WO | 2000047139 A1 | 8/2000 |
| WO | 2001035878 A2 | 5/2001 |
| WO | 2001049213 A2 | 7/2001 |
| WO | 2001054624 A1 | 8/2001 |
| WO | 2001054625 A1 | 8/2001 |
| WO | 2001056512 A1 | 8/2001 |
| WO | 2001061289 A1 | 8/2001 |
| WO | 0176510 A2 | 10/2001 |
| WO | 2001076510 A2 | 10/2001 |
| WO | 0182840 | 11/2001 |
| WO | 2001082840 A1 | 11/2001 |
| WO | 2002004757 A1 | 1/2002 |
| WO | 0222054 A1 | 3/2002 |
| WO | 2002022054 A1 | 3/2002 |
| WO | 2002028321 A2 | 4/2002 |
| WO | 0236048 A1 | 5/2002 |
| WO | 2002036048 A1 | 5/2002 |
| WO | 2002041789 A2 | 5/2002 |
| WO | 0243620 A1 | 6/2002 |
| WO | 0249540 A2 | 6/2002 |
| WO | 2002043620 A1 | 6/2002 |
| WO | 2002049540 A2 | 6/2002 |
| WO | 2002076348 A1 | 10/2002 |
| WO | 2003003943 A2 | 1/2003 |
| WO | 2003030776 A2 | 4/2003 |
| WO | 2003047468 A1 | 6/2003 |
| WO | 2003049619 A2 | 6/2003 |
| WO | 2004019825 A1 | 3/2004 |
| WO | 2005102181 A1 | 11/2005 |
| WO | 2006014233 A2 | 2/2006 |
| WO | 2006034008 A2 | 3/2006 |
| WO | 2006064490 A1 | 6/2006 |
| WO | 2006070372 A2 | 7/2006 |
| WO | 2006105009 A1 | 10/2006 |
| WO | 2006113906 A1 | 10/2006 |
| WO | 2006127756 A2 | 11/2006 |
| WO | 2007081412 A1 | 7/2007 |
| WO | 2007100408 A2 | 9/2007 |
| WO | 2008005405 A2 | 1/2008 |
| WO | 2008035337 A2 | 3/2008 |
| WO | 2008091515 A2 | 7/2008 |
| WO | 2008125906 A2 | 10/2008 |
| WO | 2008147964 A1 | 12/2008 |
| WO | 2009024859 A2 | 2/2009 |
| WO | 2009026563 A2 | 2/2009 |
| WO | 2009045338 A1 | 4/2009 |
| WO | 2009132187 A1 | 10/2009 |
| WO | 2010090878 A2 | 8/2010 |
| WO | 2010098857 A1 | 9/2010 |
| WO | 2010121076 A2 | 10/2010 |
| WO | 2011017440 A2 | 2/2011 |
| WO | 2011022658 A1 | 2/2011 |
| WO | 2011069048 A2 | 6/2011 |
| WO | 2011072084 A2 | 6/2011 |
| WO | 2011106735 A1 | 9/2011 |
| WO | 2011109813 A2 | 9/2011 |
| WO | 2011159342 A1 | 12/2011 |
| WO | 2011163275 A2 | 12/2011 |
| WO | 2012027487 A2 | 3/2012 |
| WO | 2012036742 A2 | 3/2012 |
| WO | 2012095116 A1 | 7/2012 |
| WO | 2012177942 A2 | 12/2012 |
| WO | 2013/028387 A2 | 2/2013 |
| WO | 2013045262 A1 | 4/2013 |
| WO | 2013059747 A1 | 4/2013 |
| WO | 2013096411 A1 | 6/2013 |
| WO | 2013096757 A1 | 6/2013 |
| WO | 2013116785 A1 | 8/2013 |
| WO | 2013175468 A2 | 11/2013 |
| WO | 2014121280 A2 | 8/2014 |
| WO | 2014138284 A1 | 9/2014 |
| WO | 2014144020 A1 | 9/2014 |
| WO | 2014144937 A2 | 9/2014 |
| WO | 2014162306 A2 | 10/2014 |
| WO | 2014189974 A1 | 11/2014 |
| WO | 2014194178 A1 | 12/2014 |
| WO | 2014210124 A1 | 12/2014 |
| WO | 2015051430 A1 | 4/2015 |
| WO | 2015058039 A1 | 4/2015 |
| WO | 2015063580 A2 | 5/2015 |
| WO | 2015065646 A1 | 5/2015 |
| WO | 2015120122 A2 | 8/2015 |
| WO | 2015138306 A2 | 9/2015 |
| WO | 2015173609 A1 | 11/2015 |
| WO | 2016112085 A2 | 7/2016 |
| WO | 2016126942 A2 | 8/2016 |
| WO | 2016168609 A1 | 10/2016 |
| WO | 2016196933 A1 | 12/2016 |
| WO | 2017096157 A1 | 6/2017 |
| WO | 2017132008 A1 | 8/2017 |
| WO | 2017218375 A1 | 12/2017 |
| WO | 2018005779 A1 | 1/2018 |
| WO | 2018013515 A1 | 1/2018 |

OTHER PUBLICATIONS

Chinese Search Report for CN Application No. 201680013223.9, dated Oct. 29, 2018.

International Search Report and Written Opinion for International Application No. PCT/US2016/016567, dated Aug. 3, 2016, 17 pages.

Yoganathan, A. P. et al., "The Current Status of Prosthetic Heart Valves," In Polymetric Materials and Artificial Organs, Mar. 20, 1983, pp. 111-150, American Chemical Society.

"Shape Memory Alloys," Retrieved from the Internet: <http://webdocs.cs.ualberta.ca/~database/MEMS/sma.html>, Feb. 5, 2016, 3 pages.

Al Zaibag, Muayed, et al., "Percutaneous Balloon Valvotomy in Tricuspid Stenos's," British Heart Journal, Jan. 1987, vol. 57, No. 1, pp. 51-53.

Al-Khaja, N. et al., "Eleven Years' Experience with Carpentier-Edwards Biological Valves in Relation to Survival and Complications," European Journal of Cardiothoracic Surgery, Jun. 30, 1989, 3:305-311.

Almagor, Y. et al., "Balloon Expandable Stent Implantation in Stenotic Right Heart Valved Conduits," Journal of the American College of Cardiology, Nov. 1, 1990, 16(6):1310-1314.

Andersen, H. R., "History of Percutaneous Aortic Valve Prosthesis," Herz, Aug. 2009, 34(5):343-346.

Andersen, H. R., "Transluminal catheter implanted prosthetic heart valves," International Journal of Angiology, 1998, 7(2): 102-106.

Benchimol, A. et al., "Simultaneous Left Ventricular Echocardiography and Aortic Blood Velocity During Rapid Right Ventricular Pacing in Man," The American Journal of the Medical Sciences, Jan.-Feb. 1977, 273(1):55-62.

Boudjemline, Y. et al., "Steps Toward the Percutaneous Replacement of Atrioventricular Valves: An Experimental Study," Journal of the American College of Cardiology, Jul. 2005,46(2):360-365.

Buckberg, G. et al., "Restoring Papillary Muscle Dimensions During Restoration In Dilated Hearts," Interactive Cardiovascular and Thoracic Surgery, 2005, 4:475-477.

Chamberlain, G., "Ceramics Replace Body Parts," Design News, Jun. 9, 1997, Issue 11, vol. 52, 5 pages.

(56) References Cited

OTHER PUBLICATIONS

Choo, S. J. et al., "Aortic Root Geometry: Pattern of Differences Between Leaflets and Sinuses of Valsava," The Journal of Heart Valve Disease, Jul. 1999, 8:407-415.
Cullen, et al., "Transvenous, Antegrade Melody Valve-in-Valve Implantation for Bioprosthetic Mitral and Tricuspid Valve Dysfunction", JACC: Cardiovascular Interventions, vol. 6, No. 6, Jun. 2013, pp. 598-605.
Declaration of Malcolm J. R. Dalrymple-Hay, Nov. 9, 2012, pp. 1-11; with Curriculum Vitae, Oct. 4, 2012.
Dotter, C. T. et al., "Transluminal Treatment of Arteriosclerotic Obstruction. Description of a New Technic and a Preliminary Report of its Application," Circulation, Nov. 1964, 30:654-670.
G. M. Bernacca, et al., "Polyurethane Heart Valves: Fatigue Failure, Calcification, and Polyurethane Structure," Journal of Biomedical Materials Research, Mar. 5, 1997, Issue 3, vol. 34, pp. 371-379.
Gray, H., The Aorta, Anatomy of the Human Body, 1918, Retrieved from the Internet <http://www.bartleby.com/107/142 html>, Dec. 10, 2012, 5 pages.
Gray, H., The Heart, Anatomy of the Human Body, 1918, Retrieved from the Internet <http://education.yahoo.com/reference/gray/subjects/subject/138>, Aug. 10, 2012, 9 pages.
Greenhalgh, E. S., "Design and characterization of a biomimetic prosthetic aortic heart valve," 1994, ProQuest Dissertations and Theses, Department of Fiber and Polymer Science, North Carolina State University at Raleigh, 159 pages.
H. R. Andersen et al., "Transluminal Implantation of Artificial Heart Valves: Description of a New Expandable Aortic Valve and Initial Results with Implantation by Catheter Technique in Closed Chest Pigs," European Heart Journal, 1992, Issue 5, vol. 13, pp. 704-708.
Inoue, K. et al., "Clinical Application of Transvenous Mitral Commissurotomy by a New Balloon Catheter," The Journal of Thoracic and Cardiovascular Surgery, 1984, 87:394-402.
International Search Report and Written Opinion for International Application No. PCT/US2016/012305, dated Aug. 3, 2016, 18 pages.
Jin, X. Y. et al., "Aortic Root Geometry and Stentless Porcine Valve Competence," Seminars in Thoracic and Cardiovascular Surgery, Oct. 1999, 11(4):145-150.
Knudsen, L. L. et al., "Catheter-implanted prosthetic heart valves. Transluminal catheter implantation of a new expandable artificial heart valve in the descending thoracic aorta in isolated vessels and closed chest pigs," The International Journal of Artificial Organs, 1993,16(5):253-262.
Kolata, G., "Device That Opens Clogged Arteries Gets a Failing Grade in a New Study," New York Times [online], <http://www.nytimes.com/1991/01/03/health/device-that-opens-clogged-ar-teries-gets-a-faili . . . ,>, published Jan. 3, 1991,retrieved from the Internet on Feb. 5, 2016, 3 pages.
Lawrence, D. D., "Percutaneous Endovascular Graft: Experimental Evaluation," Radiology, 1987, 163:357-360.
Lozonschi, L., et al. "Transapical mitral valved stent implantation: A survival series in swine," The Journal of Thoracic and Cardiovascular Surgery, 140(2):422-426 (Aug. 2010) published online Mar. 12, 2010, 1 page.
Lutterr, G. et al., "Mitral Valved Stent Implantation," European Journal of Cardia-Thoracic Surgery, 2010, 38:350-355, 2 pages.
Ma, L. et al., "Double-crowned valved stents for off-pump mitral valve replacement," European Journal of Cardio-Thoracic Surgery, Aug. 2005, 28(2): 194-198.
Orton, C., "Mitralseal: Hybrid Transcatheter Mitral Valve Replacement," Symposium: Small Animal Proceedings, 2011, pp. 311-312.
Pavcnik, D. et al. "Development and Initial Experimental Evaluation of a Prosthetic Aortic Valve for Transcatheter Placement," Radiology, 1992; 183:151-154.
Porstmann, W. et al., "Der Verschlul?. des Ductus Arteriosus Persistens ohne Thorakotomie," Thoraxchirurgie Vaskulare Chirurgie, Band 15, Heft 2, Stuttgart, Apr. 1967, pp. 199-203.
Rashkind, W. J., "Creation of an Atrial Septal Defect Without Thoracotomy," The Journal of the American Medical Association, Jun. 13, 1966, 196( 11 ): 173-174.
Reul, H. et al., "The Geomety of the Aortic Root in Health, at Valve Disease and After Valve Replacement," J. Biomechanics, 1990, 23(2):181-191.
Robert C. Ashton Jr., "Development of an Intraluminal Device for the Treatment of Aortic Regurgitation: Prototype and in Vitro Testing System," Journal of Thoracic and Cardiovascular Surgery, 1996, Issue/vol. 112, pp. 979-983.
Rosch, J. et al., "The Birth, Early Years and Future of Interventional Radiology," J Vase Interv Radiol., Jul. 2003, 4:841-853.
Ross, D. N., "Aortic Valve Surgery," Guy's Hospital, London, 1968, pp. 192-197.
Rousseau, E. P. M et al., "A Mechanical Analysis of the Closed Hancock Heart Valve Prosthesis," Journal of Biomechanics, 1998, 21(7):545-562.
Sabbah, A. N. et al., "Mechanical Factors in the Degeneration of Porcine Bioprosthetic Valves: An Overview," Dec. 1989, Journal of Cardiac Surgery, 4(4):302-309.
Selby, M.D., J. Bayne, "Experience with New Retrieval Forceps for Foreign Body Removal in the Vascular, Urinary, and Biliary Systems," Radiology 1990; 176:535-538.
Serruys, P.W., et al., "Stenting of Coronary Arteries. Are we the Sorcerer's Apprentice?," European Heart Journal (1989) 10, 774-782, pp. 37-45, Jun. 13, 1989.
Sigwart, U., "An Overview of Intravascular Stents: Old and New," Chapter 48, Interventional Cardiology, 2nd Edition, W.B. Saunders Company, Philadelphia, PA, © 1994,1990, pp. 803-815.
Tofeig, M. et al., "Transcatheter Closure of a Mid-Muscular Ventricular Septal Defect with an Amplatzer VSD Occluder Device," Heart, 1999, 81:438-440.
Uchida, Barry T., et al., "Modifications of Gianturco Expandable Wire Stents," AJR:150, May 1988, Dec. 3, 1987, pp. 1185-1187.
US 9,155,620, 10/2015, Gross et al. (withdrawn)
Watt, A.H., et al. "Intravenous Adenosine in the Treatment of Supraventricular Tachycardia; a Dose-Ranging Study and Interaction with Dipyridamole," British Journal of Clinical Pharmacology (1986), 21, pp. 227-230.
Webb, J. G. et al., "Percutaneous Aortic Valve Implantation Retrograde from the Femoral Artery," Circulation, 2006, 113:842-850.
Wheatley, M.D., David J., "Valve Prostheses," Rob & Smith's Operative Surgery, Fourth Edition, pp. 415-424, ButtenNorths 1986.
A. P. Yoganathan et al., "The Current Status of Prosthetic Heart Valves, Polymetric Materials and Artificial Organs," American Chemical Society , Mar. 20, 1983 pp. 111-150.
Al Zaibag, M. et al., "Percutaneous Balloon Valvotomy in Tricuspid Stenosis," British Heart Journal, Jan. 1987, 57 (1):51-53.
Bernacca, G. M. et al., "Polyurethane heart valves: Fatigue failure, calcification, and polyurethane structure," Journal of Biomedical Materials Research, Mar. 5, 1997, 34(3):371-379.
Drawbaugh, K., "Feature—Heart Surgeons Explore Minimally Invasive Methods," Reuters Limited, Jul. 16, 1996, 3 pages.
Henning Rud Andersen, "Transluminal Catheter Implanted Prosthetic Heart Valves," International Journal of Angiology, 1998, Issue 2, vol. 7 pp. 102-106.
Lutter, Georg, et al., "Mitral Valved Stent Implantation," European Journal of Cardio-Thoracic Surgery, 2010, vol. 38pp. 350-355.
Moazami, N. et al., "Transluminal aortic valve placement: A feasibility study with a newly designed collapsible aortic Valve," ASAIO Journal, Sep./ Oct. 1996 42(5):M381-M385.
Rashkind, W. J., "Historical Aspects of Interventional Cardiology: Past, Present, Future," Texas Heart Institute Journal, Dec. 1986, 13(4):363-367.
Rousseau, E. P. M. et al., "A mechanical analysis of the closed Hancock heart valve prosthesis," Journal of Biomechanics, 1988, 21(7):545-562.

\* cited by examiner

APPARATUS AND METHODS FOR TRANSFEMORAL DELIVERY OF PROSTHETIC MITRAL VALVE

CROSS-REFERENCE TO RELATED APPLICATIONS

This application is a continuation of U.S. patent application Ser. No. 15/217,376, filed Jul. 22, 2016, which is continuation of International Application No. PCT/US2015/014572, filed Feb. 5, 2015, which claims priority to and the benefit of U.S. Provisional Patent Application Ser. No. 61/935,899, entitled "Transfemoral Delivery of Prosthetic Mitral Valve," filed Feb. 5, 2014, and U.S. Provisional Patent Application No. 62/100,548, entitled "Apparatus and Methods for Transfemoral Delivery of Prosthetic Mitral Valve," filed Jan. 7, 2015, each of the disclosures of which is incorporated herein by reference.

BACKGROUND

Embodiments are described herein that relate to devices and methods for use in the transfemoral delivery and deployment of prosthetic valves, and particularly to devices and methods for delivering expandable prosthetic mitral valves.

Prosthetic heart valves can pose particular challenges for delivery and deployment within a heart. Valvular heart disease, and specifically, aortic and mitral valve disease is a significant health issue in the United States (US); annually approximately 90,000 valve replacements are conducted in the US. Traditional valve replacement surgery involving the orthotopic replacement of a heart valve is considered an "open heart" surgical procedure. Briefly, the procedure necessitates surgical opening of the thorax, the initiation of extra-corporeal circulation with a heart-lung machine, stopping and opening the heart, excision and replacement of the diseased valve, and re-starting of the heart. While valve replacement surgery typically carries a 1-4% mortality risk in otherwise healthy persons, a significantly higher morbidity is associated to the procedure largely due to the necessity for extra-corporeal circulation. Further, open heart surgery is often poorly tolerated in elderly patients. Thus elimination of the extra-corporeal component of the procedure could result in reduction in morbidities and cost of valve replacement therapies could be significantly reduced.

While replacement of the aortic valve in a transcatheter manner is the subject of intense investigation, lesser attention has been focused on the mitral valve. This is in part reflective of the greater level of complexity associated to the native mitral valve apparatus, and thus, a greater level of difficulty with regards to inserting and anchoring the replacement prosthesis. A need exists for delivery devices and methods for transcatheter mitral valve replacements.

BRIEF SUMMARY

Apparatus and methods are described herein for use in the transfemoral delivery and deployment of a prosthetic mitral valve. In some embodiments, a method includes inverting an outer frame of a prosthetic mitral valve when in a biased expanded configuration. The prosthetic mitral valve is formed with a shape-memory material. After inverting the outer frame, the prosthetic mitral valve is inserted into a lumen of a delivery sheath such that the mitral valve is moved to a collapsed configuration. The delivery sheath is inserted into a femoral vein of a patient and moved through the femoral vein and a septum of a heart of the patient until a distal end portion of the delivery sheath is disposed in the left atrium of the heart. The prosthetic mitral valve is moved distally out of the delivery sheath such that the inverted outer frame reverts and the prosthetic mitral valve assumes its biased expanded configuration. The prosthetic mitral valve is then positioned within a mitral annulus of the heart.

DETAILED DESCRIPTION

Apparatus and methods are described herein for use in the transfemoral delivery and deployment of a prosthetic mitral valve into a heart. As described herein, in some embodiments, a method includes inverting an outer frame of a prosthetic mitral valve when in a biased expanded configuration. The prosthetic mitral valve is formed with a shape-memory material. After inverting the outer frame, the prosthetic mitral valve is inserted into a lumen of a delivery sheath such that the mitral valve is moved to a collapsed configuration. The delivery sheath is inserted into a femoral vein of a patient and moved through the femoral vein and a septum of a heart of the patient until a distal end portion of the delivery sheath is disposed in the left atrium of the heart. The prosthetic mitral valve is moved distally out of the delivery sheath such that the inverted outer frame reverts and the prosthetic mitral valve assumes its biased expanded configuration. The prosthetic mitral valve is then positioned within a mitral annulus of the heart.

Figure 1:
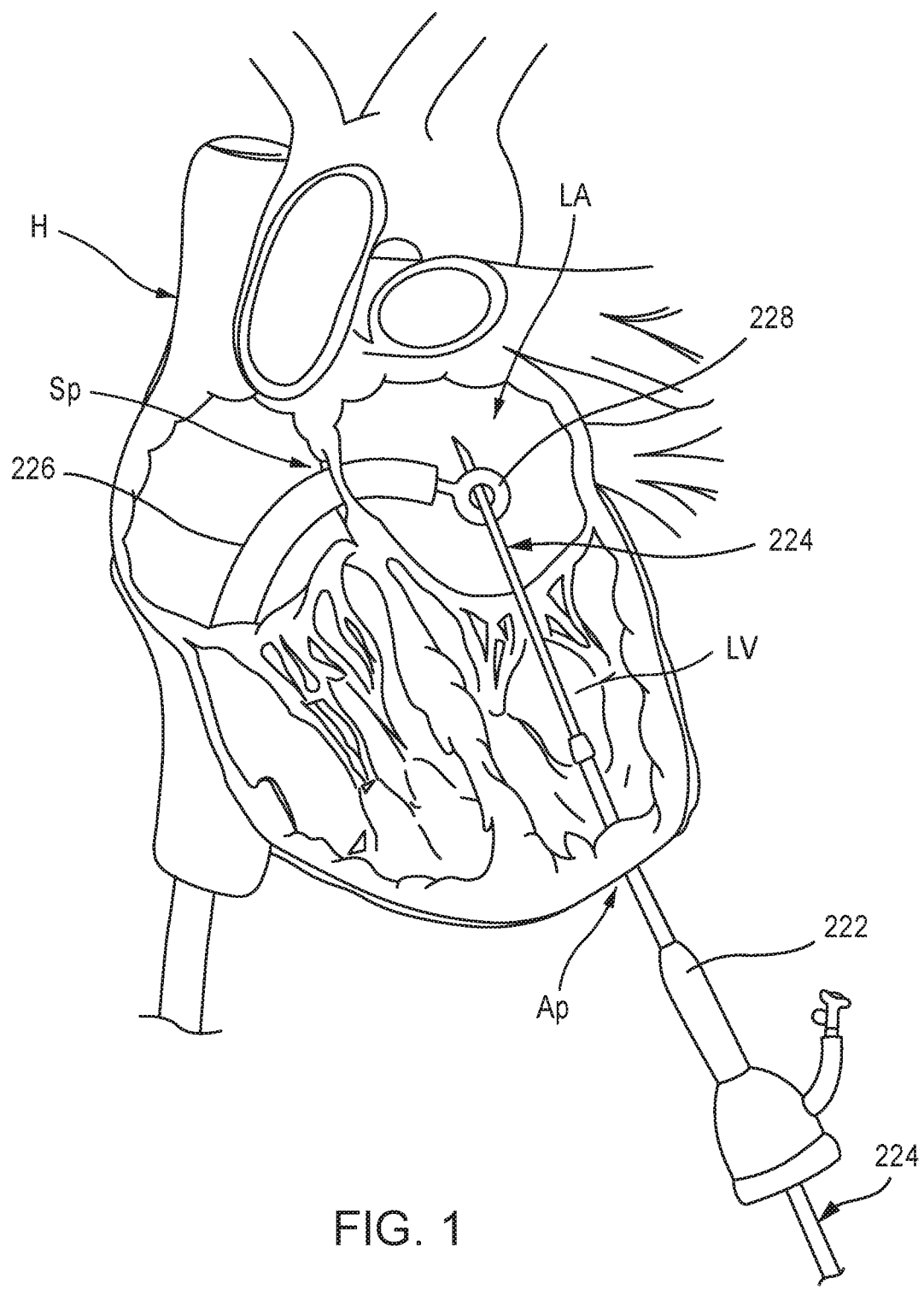
FIGS. 1-6 are each a cross-sectional illustration of a heart with devices used during various stages in a procedure to transfemorally deliver and deploy a prosthetic mitral valve.
Figure 2:
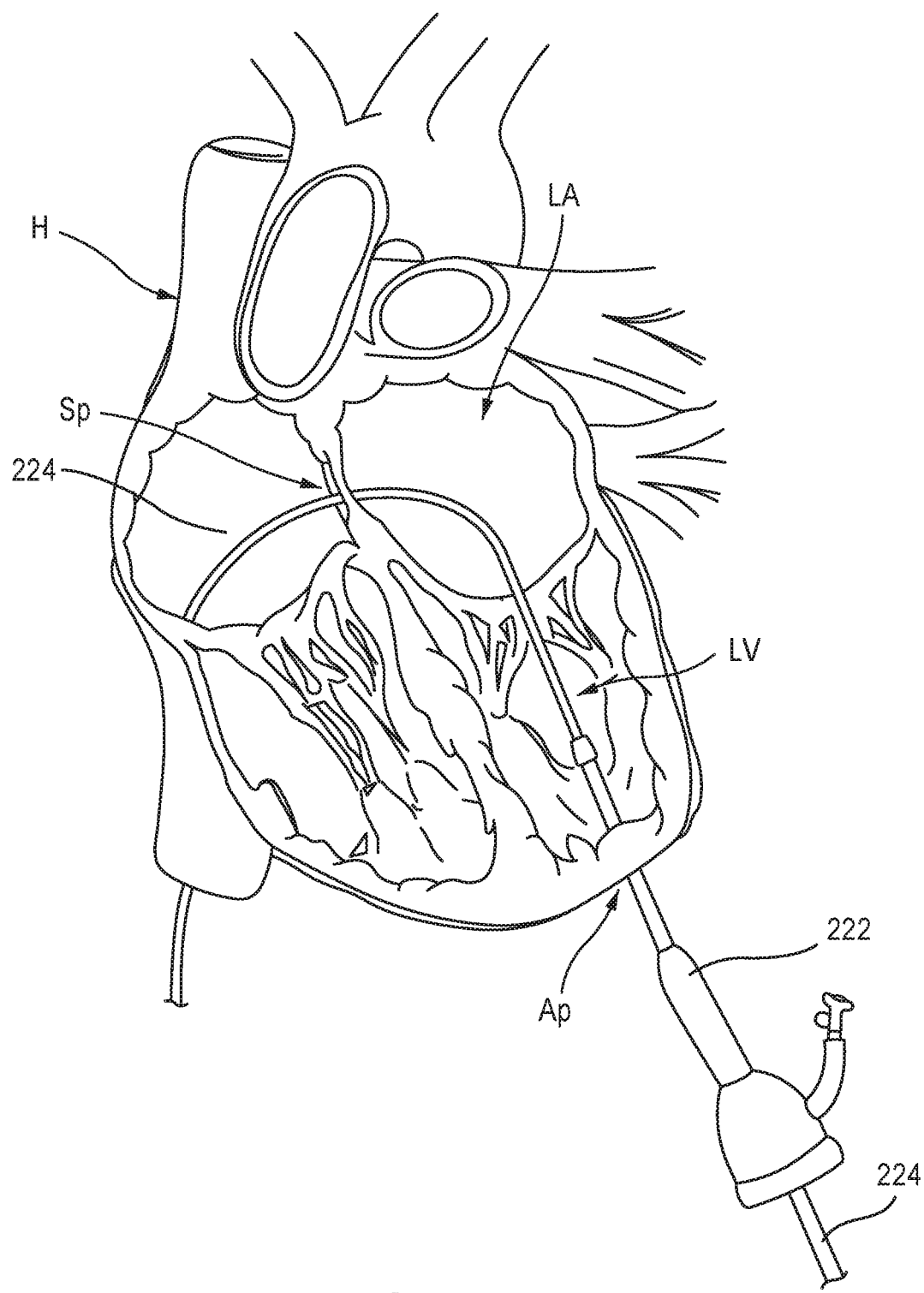

FIGS. 1-6 illustrate a method of delivering a prosthetic mitral valve 200 (shown in FIGS. 3-6) to a left atrium LA of a heart H via introduction through a femoral vein. As shown in FIG. 1, a procedural catheter 222 is inserted through an apical puncture (e.g., a 5F apical puncture) in a ventricular wall at the apex Ap of the heart H. A leader tube 224 is inserted through a lumen (not shown) of the procedural catheter 222 and extended through the left ventricle LV, through a mitral valve gap and into the left atrium LA. A delivery sheath 226 is introduced through a femoral vein puncture and extended through the inferior vena cava, into the right atrium, and then through a transseptal puncture of the septum Sp of the heart H, and into the left atrium LA of the heart H. A snare device 228 is movably disposed within the delivery sheath 226 and used to grab or snare a distal end portion of the leader tube 224, as shown in FIG. 1. The snare device 228 can be used to pull the leader tube 224 through the delivery sheath 226 such that the distal end portion of the leader tube 224 extends outside the femoral vein and a proximal end of the leader tube 224 is disposed through the ventricular wall at the apex Ap of the heart H, as shown in FIG. 2. The leader tube 224 allows for back-loading of the prosthetic mitral valve 200 starting in the femoral vein and exiting the heart H at the apex Ap. Although not shown in FIGS. 1 and 2, the procedural catheter 224 is disposed outside the patient's body, the distal end of the leader tube 224 extends outside the femoral vein and outside the patient's body, and the proximal end of the leader tube 224 extends outside the apex Ap and outside the patient's body. Although the above described snare process describes delivering the leader tube 224 to the left atrium of the heart and then snaring the leader tube 224 using the snare device 228, in alternative embodiments, the leader tube 224 can be delivered to the left ventricle LV and the snare device 228 and delivery sheath 226 can be inserted through the mitral annulus and into the left ventricle LV to grab or snare the leader tube 224 as described above.

After the leader tube 224 has been extended between the apex Ap and the access site to the femoral vein, a valve leader member 234 attached to the prosthetic mitral valve 200 (also referred to as "valve") can be inserted into the leader tube 224 at the femoral end of the leader tube 224 and extended through the leader tube 224 until the valve leader member 234 exits the leader tube at the apex end of the leader tube 224. After the valve leader member 234 is inserted and extended outside the apex Ap, the leader tube 224 can be removed from the patient. For example, the leader tube 224 can be pulled out through the apex puncture site, or through the femoral vein puncture site. Thus, only the valve leader member 234 remains disposed within the body, as shown in FIG. 3.

Figure 26:
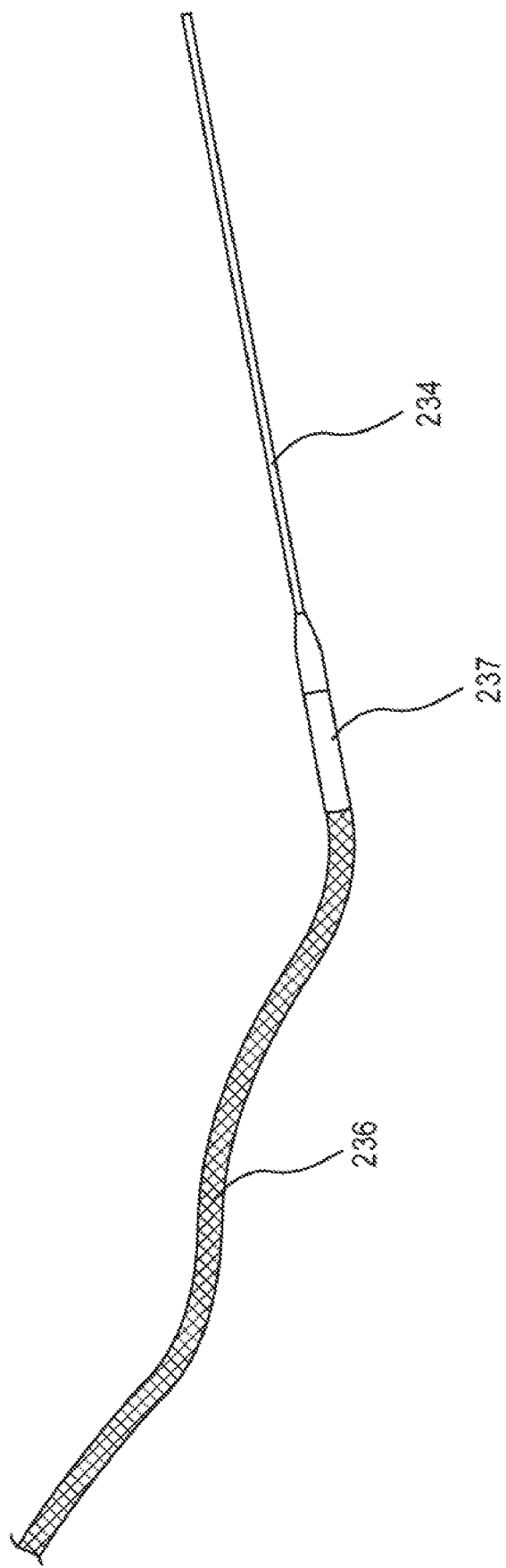
FIG. 26 is a side view illustrating a portion of a tether coupled to a portion of a valve leader member, according to an embodiment.

The valve leader member 234 can have a tapered distal end 235 to aid in the insertion and maneuvering of the valve leader member 234 through the leader tube 224. The valve leader member 234 is attached at a proximal end portion 237 to a tether line 236 (also referred to herein as "tether"), which is attached to the valve 200. FIG. 26 illustrates an enlarged view of the attachment of the proximal end portion 237 to tether 236. The tether 236 can be formed, for example, as a braided rope or cord as shown, for example, in FIG. 26.

Figure 3:
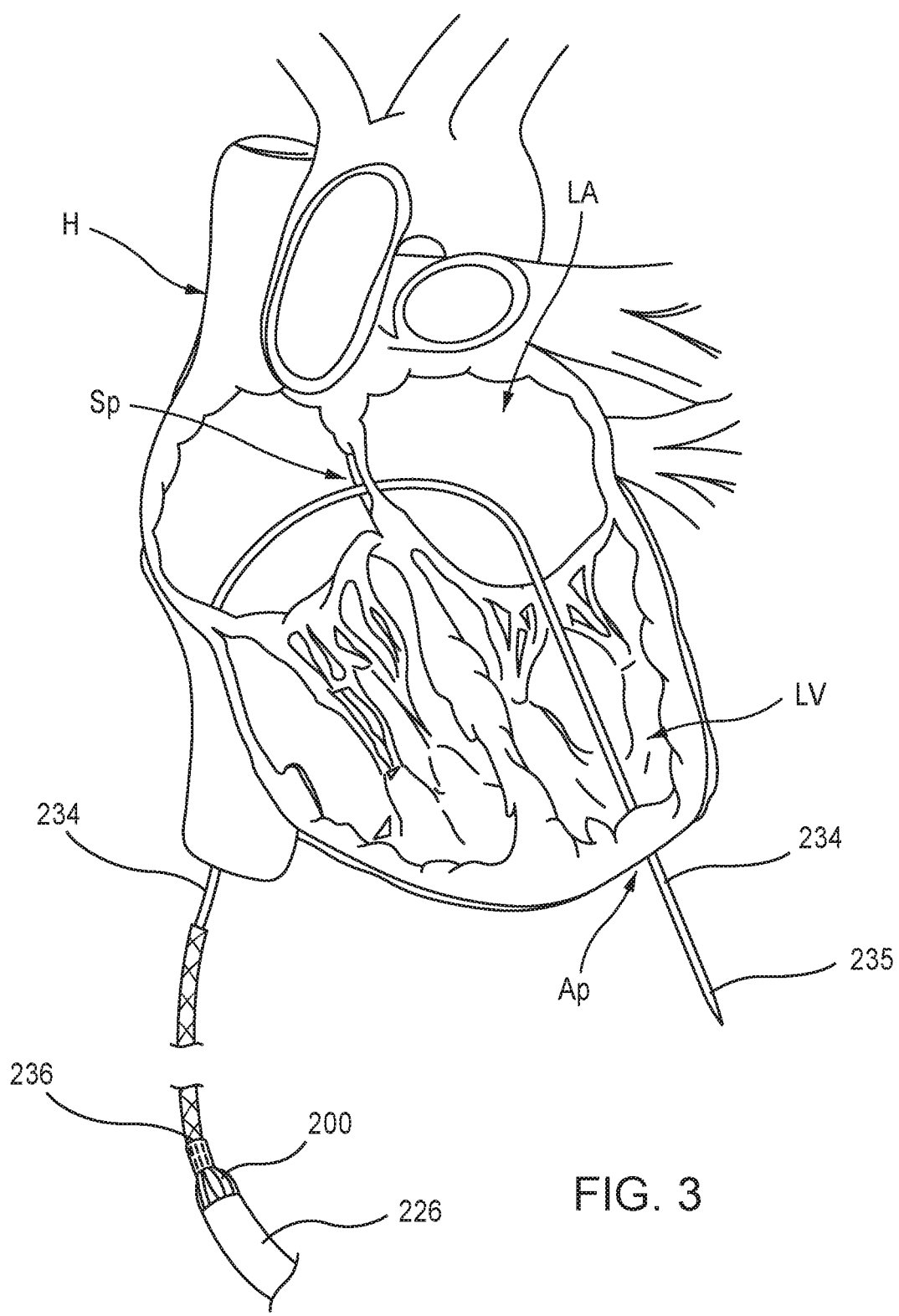

As shown in FIG. 3, the valve 200 is partially disposed within a lumen of the delivery sheath 226. Although the delivery sheath 226 is used to deliver both the snare device 228 and the valve 200, in other embodiments, a different delivery sheath can be used to deliver the snare device 228 than is used to deliver the valve 200. As shown in FIG. 3, prior to inserting the valve leader member 234 into the leader tube 224, the procedural catheter 222 can be removed. Alternatively, the procedural catheter 222 can be removed after inserting the valve leader member 234.

Also as shown in FIG. 3, in this embodiment, a portion of the valve 200 is allowed to partially deploy outside a distal end of the delivery sheath 226. The partially deployed portion of the valve 200 can be used as a lead-in to the delivery sheath 226 as the valve 200 is inserted through femoral vein. For example, the valve 200 can be formed with a shape-memory material (as described in more detail below) and can have a biased undeformed shape and can be manipulated and/or deformed (e.g., compressed and/or expanded) and, when released, return to its original undeformed shape. In some embodiments, the valve 200 can have a biased expanded or undeformed configuration when deployed within a heart, and can be moved to a collapsed or deformed configuration when placed within the lumen of the delivery sheath 226 for delivery through the femoral vein. The valve can be, for example, a valve constructed the same as or similar to, and function in the same or similar manner as, the prosthetic heart valve 500, described in detail below.

Figure 4:
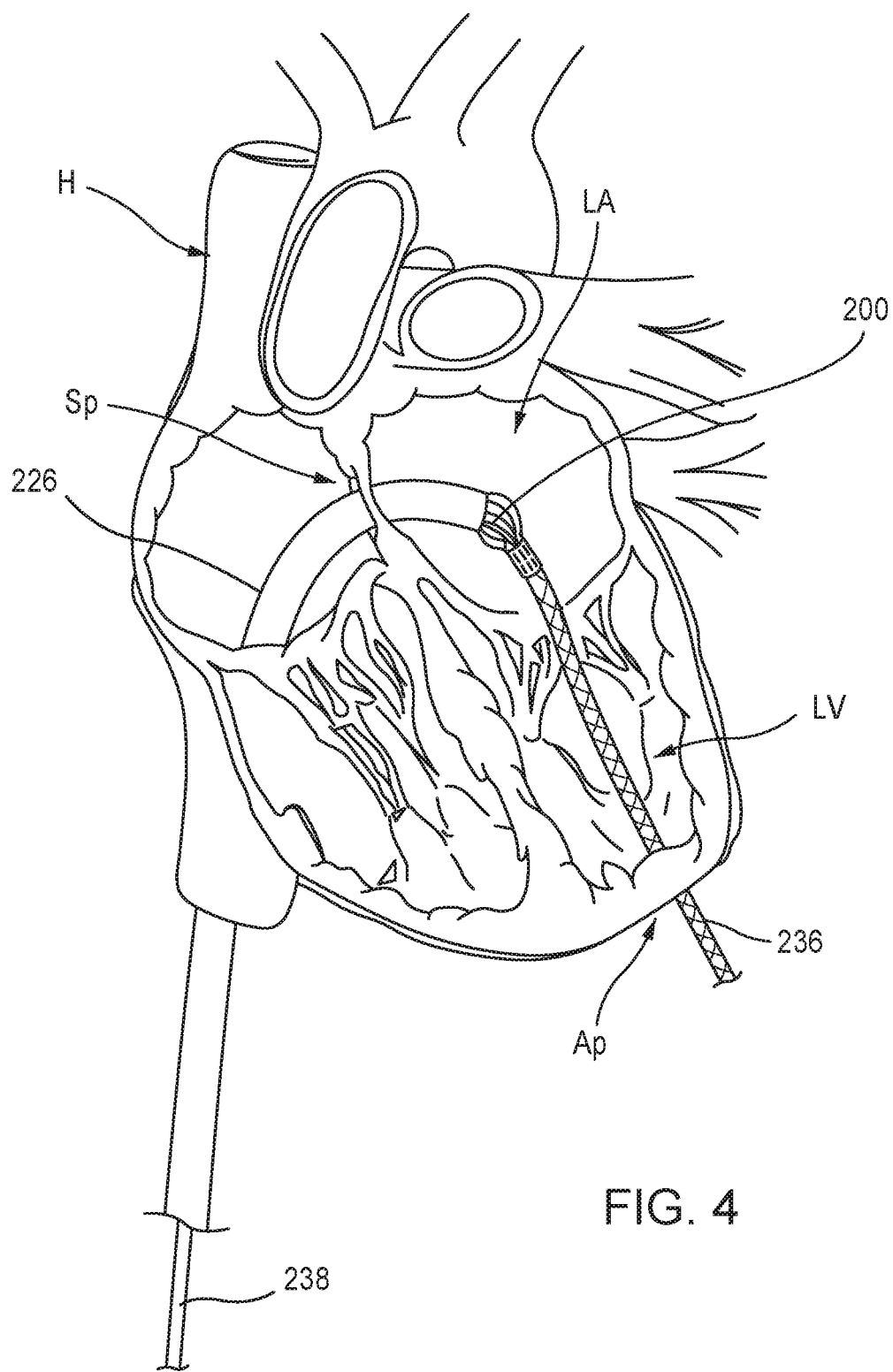

After the valve leader member 234 has been placed in position between the femoral puncture site and the apical puncture site, as described above, the delivery sheath 226 with the valve 200 can be inserted through the femoral puncture site and moved through the femoral vein, through the inferior vena cava, into the right atrium, and then through the septum Sp until a distal end portion of the delivery sheath 226 (with the valve 200) is disposed within the left atrium LA, as shown in FIG. 4. As shown in FIG. 4, the tether 236 extends from the valve 200 through the apical puncture and outside the patient's body. As the delivery sheath 226 is advanced, the tether 236 can optionally be pulled at the apex end to help move the delivery sheath 226, with the valve 200 disposed therein, through the femoral vein, through the septal puncture and into the left atrium LA. The valve 200 can then be fully deployed within the left atrium LA (see, e.g., FIG. 5) by pulling the apex end portion of the tether 236 until the valve 200 is pulled out of the lumen of the delivery sheath 226 and disposed within the left atrium LA. Alternatively, pusher device 238 (see, e.g., FIG. 4) can be inserted within the delivery sheath 226 and used to push the valve 200 outside a distal end of the delivery sheath 226. In yet other embodiments, the pusher device 238 can be used push the valve 200 while the tether 236 is pulled. In other words, the valve 200 can be deployed by pushing the valve 200 with the pusher device 238, by pulling the valve 200 with the tether 236, or both. The pusher 238 can also be used to aid in positioning the valve 200 in a desired radial orientation within the left atrium LA. For example, the pusher device 238 can define an internal lumen (not shown) that can be placed over an inner frame portion of the valve 200 to hold the inner frame portion in a small diameter, which can help enable the valve 200 to be positioned in a desired radial orientation and be seated within the annulus of the mitral valve. Further examples of such a valve assist device are described below with reference to FIGS. 29-31.

Figure 5:
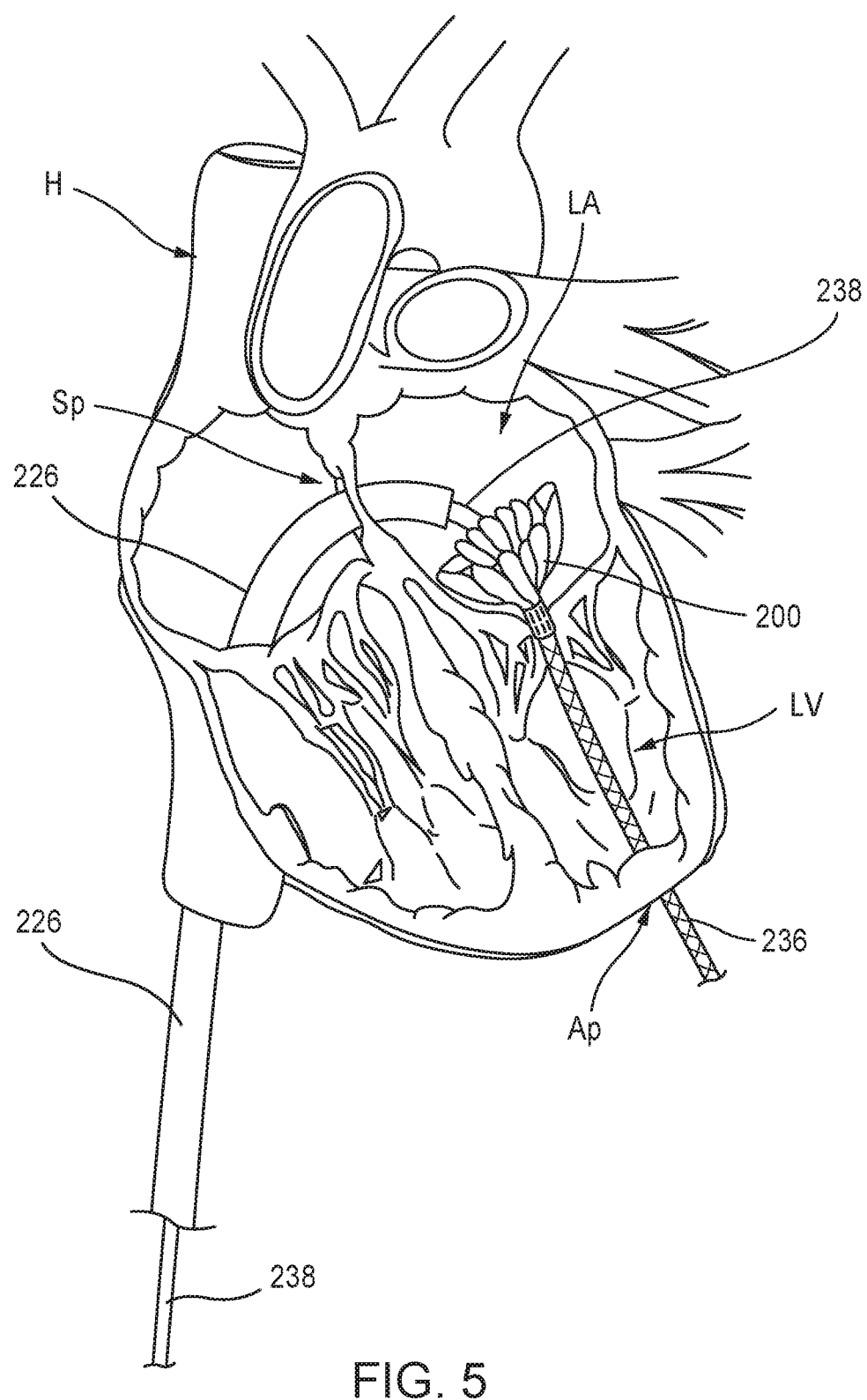
Figure 6:
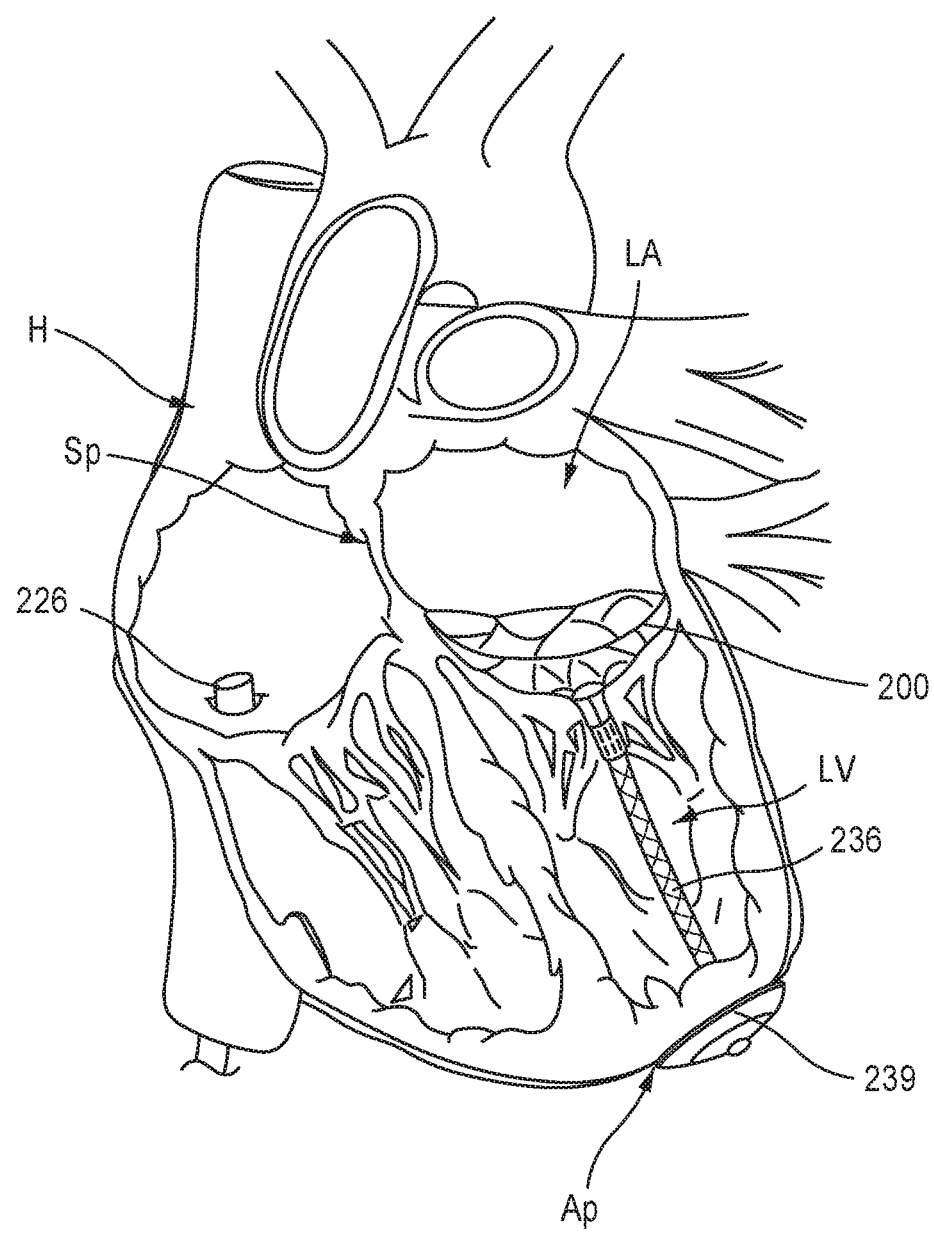

As shown in FIGS. 5 and 6, as the valve 200 is deployed within the left atrium LA, the valve 200 is allowed to assume its biased expanded or deployed configuration. The delivery sheath 226 can then be removed from the patient and the valve 200 can be positioned and tensioned using the tether 236 to obtain the desired or optimal location in the native mitral annulus and minimize perivalvular leaks. An epicardial pad device 239 can be used to secure the tether 236 and valve 200 in position within the mitral annulus as shown in FIG. 6. For example, an epicardial pad device as described in International Patent Application No. PCT/US14/49218 ("the '218 PCT application"), the disclosure of which is incorporated herein by reference in its entirety, can be used. In some embodiments, an expandable epicardial pad can be used to secure the tether and valve in posiiton. Examples embodiments of expandable pads that can be used are described herein with reference to FIGS. 33-47. Such a pad can be smaller in size such that the pad can be delivered to the heart via a small incision and small catheter or delivery sheath. In some embodiments, a positioning device (not shown) can be used to help position the valve 200 and deploy the epicardial pad device. For example, a positioning device as described in the '218 PCT application incorporated by reference above, or devices described in International Patent Application No. PCT/US14/61046, the disclosure of which is incorporated herein by refence in its entirety, can be used. In some embodiments, rather than securing the prosthetic mitral valve with a tether and epicardial pad, the prosthetic mitral valve can be secured with clips or other coupling methods to a portion(s) of the mitral valve apparatus and/or the ventricular wall of the heart. For example, such coupling methods are described in International Patent Application No. PCT/US14/58826 ("the '826 PCT application"), the disclosure of which is incorporated herein by reference in its entirety.

Figure 7:
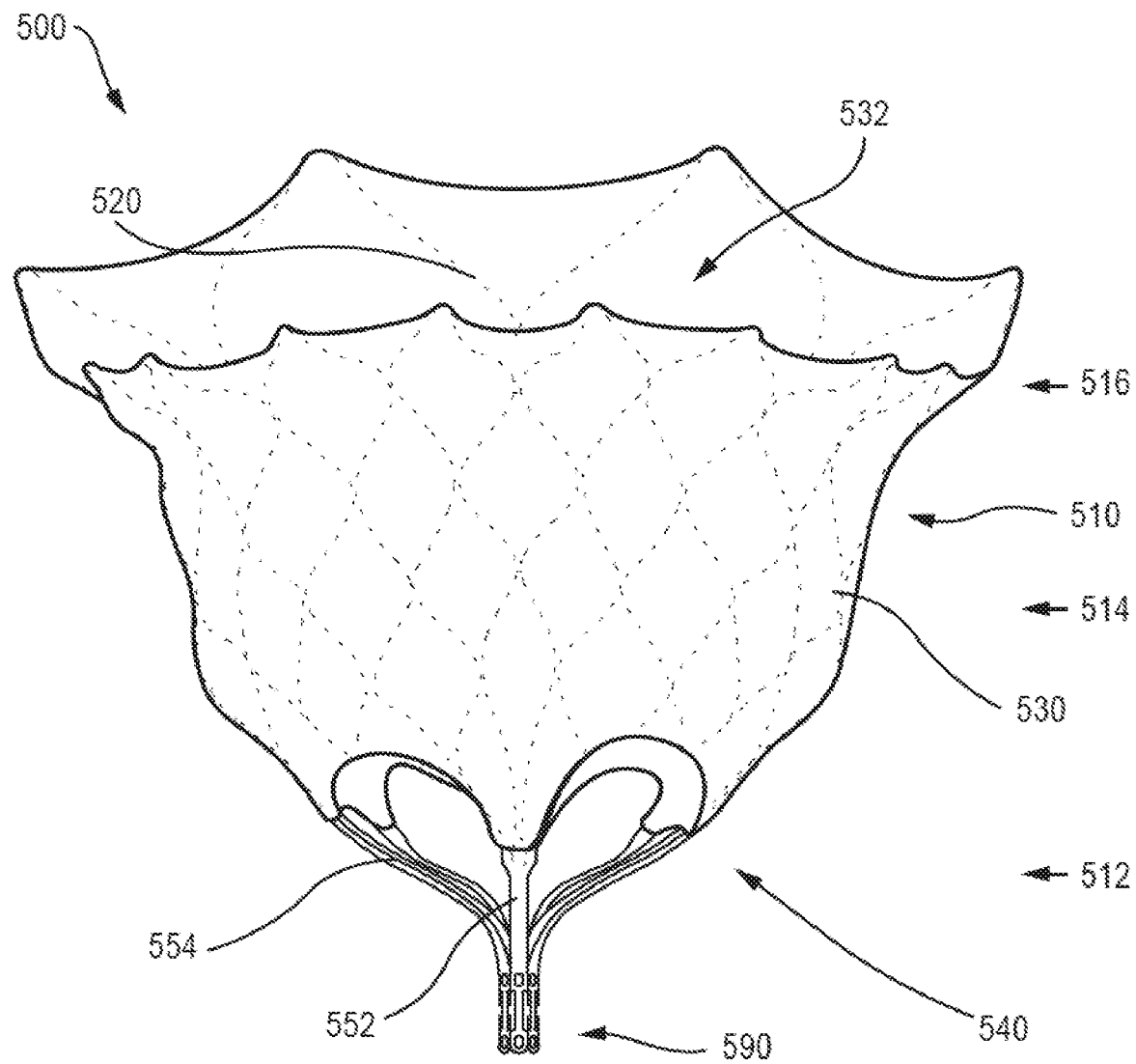
FIGS. 7-9 are front, bottom, and top views of a prosthetic heart valve according to an embodiment.
Figure 8:
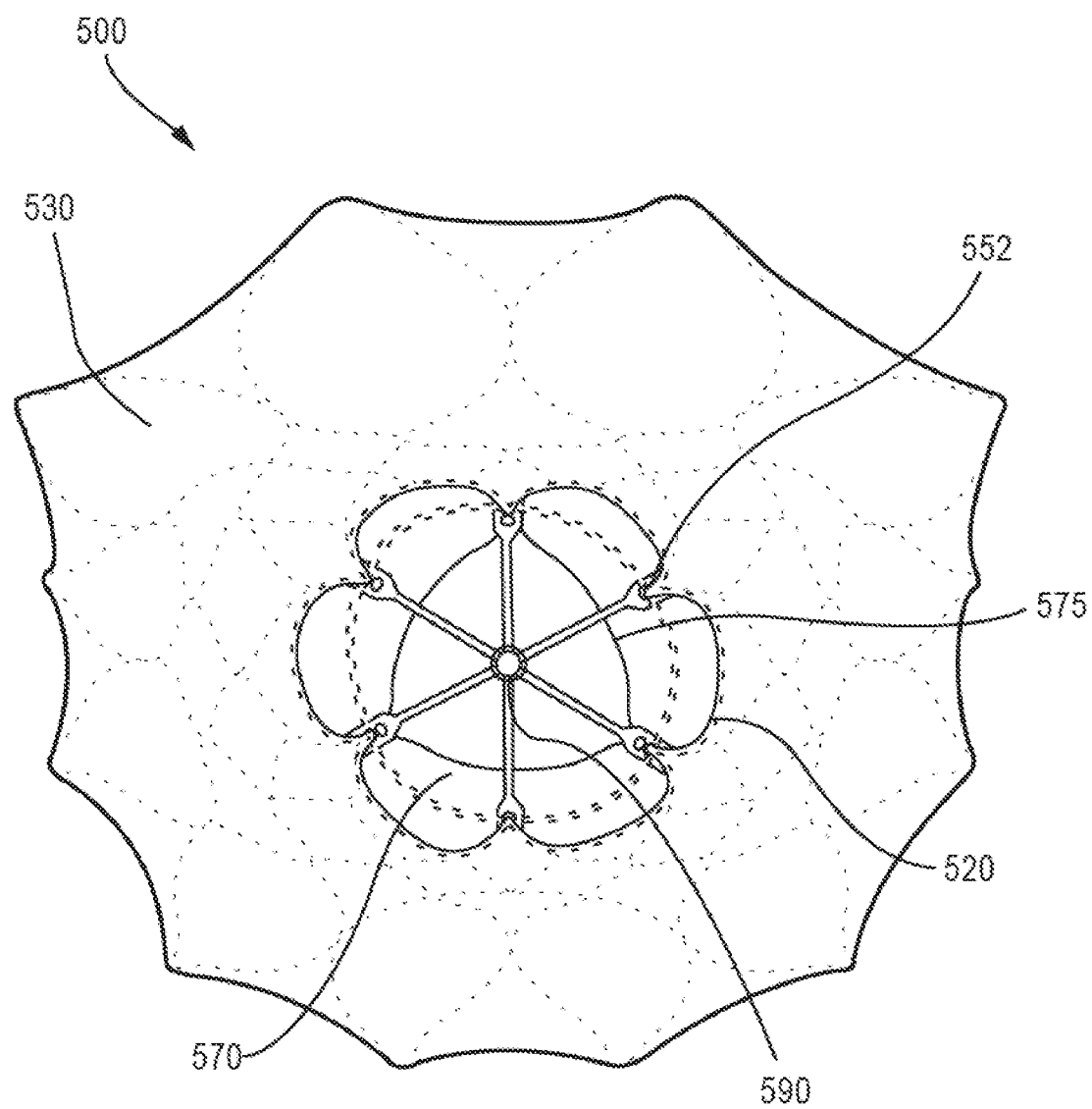
Figure 9:
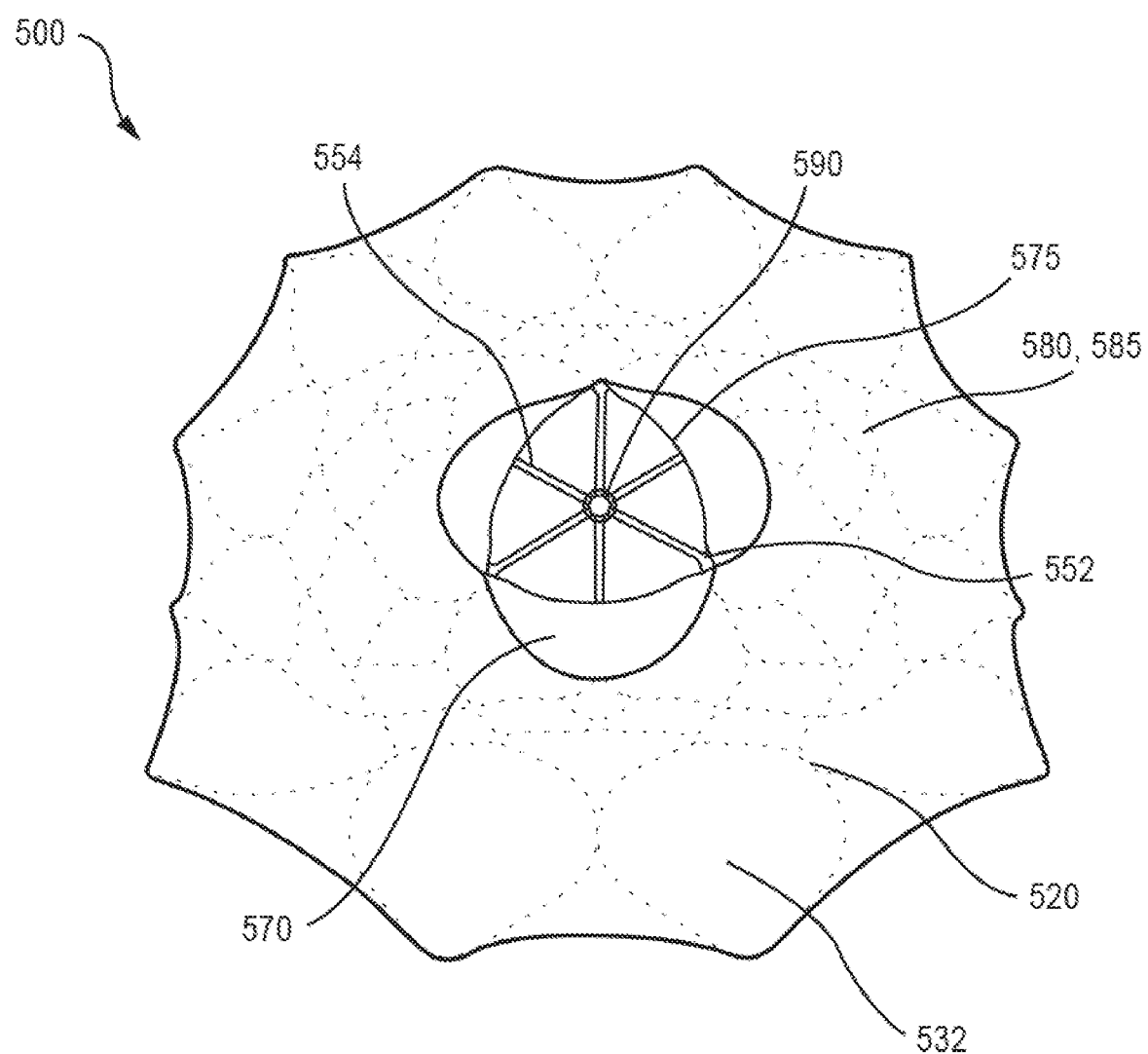

FIGS. 7-9 illustrate an embodiment of a prosthetic heart valve that can be delivered and deployed within a left atrium of a heart using a transfemoral delivery approach as described above. FIGS. 7-9 are front, bottom, and top views, respectively, of a prosthetic heart valve 500 according to an embodiment. Prosthetic heart valve 500 (also referred to herein as "valve") is designed to replace a damaged or diseased native heart valve such as a mitral valve. Valve 500 includes an outer frame assembly 510 and an inner valve assembly 540 coupled to the outer frame assembly 510.

As shown, outer frame assembly 510 includes an outer frame 520, covered on all or a portion of its outer face with an outer covering 530, and covered on all or a portion of its inner face by an inner covering 532. Outer frame 520 can provide several functions for prosthetic heart valve 500, including serving as the primary structure, as an anchoring mechanism and/or an attachment point for a separate anchoring mechanism to anchor the valve to the native heart valve apparatus, a support to carry inner valve assembly 540, and/or a seal to inhibit paravalvular leakage between prosthetic heart valve 500 and the native heart valve apparatus.

Outer frame 520 is configured to be manipulated and/or deformed (e.g., compressed and/or expanded) and, when released, return to its original (undeformed) shape. To achieve this, outer frame 520 can be formed of materials, such as metals or plastics that have shape memory properties. With regards to metals, Nitinol® has been found to be especially useful since it can be processed to be austenitic, martensitic or super elastic. Other shape memory alloys, such as Cu—Zn—Al—Ni alloys, and Cu—Al—Ni alloys, may also be used.

As best shown in FIG. 7, outer frame assembly 510 has an upper end (e.g., at the atrium portion 516), a lower end (e.g., at the ventricle portion 512), and a medial portion (e.g., at the annulus portion 514) therebetween. The medial portion of the outer frame assembly 510 has a perimeter that is configured (e.g., sized, shaped) to fit into an annulus of a native atrioventricular valve. The upper end of the outer frame assembly 510 has a perimeter that is larger than the perimeter of the medial portion. In some embodiments, the perimeter of the upper end of the outer frame assembly 510 has a perimeter that is substantially larger than the perimeter of the medial portion. As shown best in FIG. 9, the upper end and the medial portion of the outer frame assembly 510 has a D-shaped cross-section. In this manner, the outer frame assembly 510 promotes a suitable fit into the annulus of the native atrioventricular valve.

Inner valve assembly 540 includes an inner frame 550, an outer covering 560, and leaflets 570. As shown, the inner valve assembly 540 includes an upper portion having a periphery formed with multiple arches. The inner frame 550 includes six axial posts or frame members that support outer covering 560 and leaflets 570. Leaflets 570 are attached along three of the posts, shown as commissure posts 552 (best illustrated in FIG. 8), and outer covering 560 is attached to the other three posts, 554 (best illustrated in FIG. 8), and optionally to commissure posts 552. Each of outer covering 560 and leaflets 570 are formed of approximately rectangular sheets of material, which are joined together at their upper, or atrium end. The lower, ventricle end of outer covering 560 may be joined to inner covering 532 of outer frame assembly 510, and the lower, ventricle end of leaflets 570 may form free edges 575, though coupled to the lower ends of commissure posts 552.

Although inner valve assembly 540 is shown as having three leaflets, in other embodiments, an inner valve assembly can include any suitable number of leaflets. The leaflets 570 are movable between an open configuration and a closed configuration in which the leaflets 570 coapt, or meet in a sealing abutment.

Outer covering 530 of the outer frame assembly 510 and inner covering 532 of outer frame assembly 510, outer covering 560 of the inner valve assembly 540 and leaflets 570 of the inner valve assembly 540 may be formed of any suitable material, or combination of materials, such as those discussed above. In this embodiment, the inner covering 532 of the outer frame assembly 510, the outer covering 560 of the inner valve assembly 540, and the leaflets 570 of the inner valve assembly 540 are formed, at least in part, of porcine pericardium. Moreover, in this embodiment, the outer covering 530 of the outer frame assembly 510 is formed, at least in part, of polyester.

Figure 10:
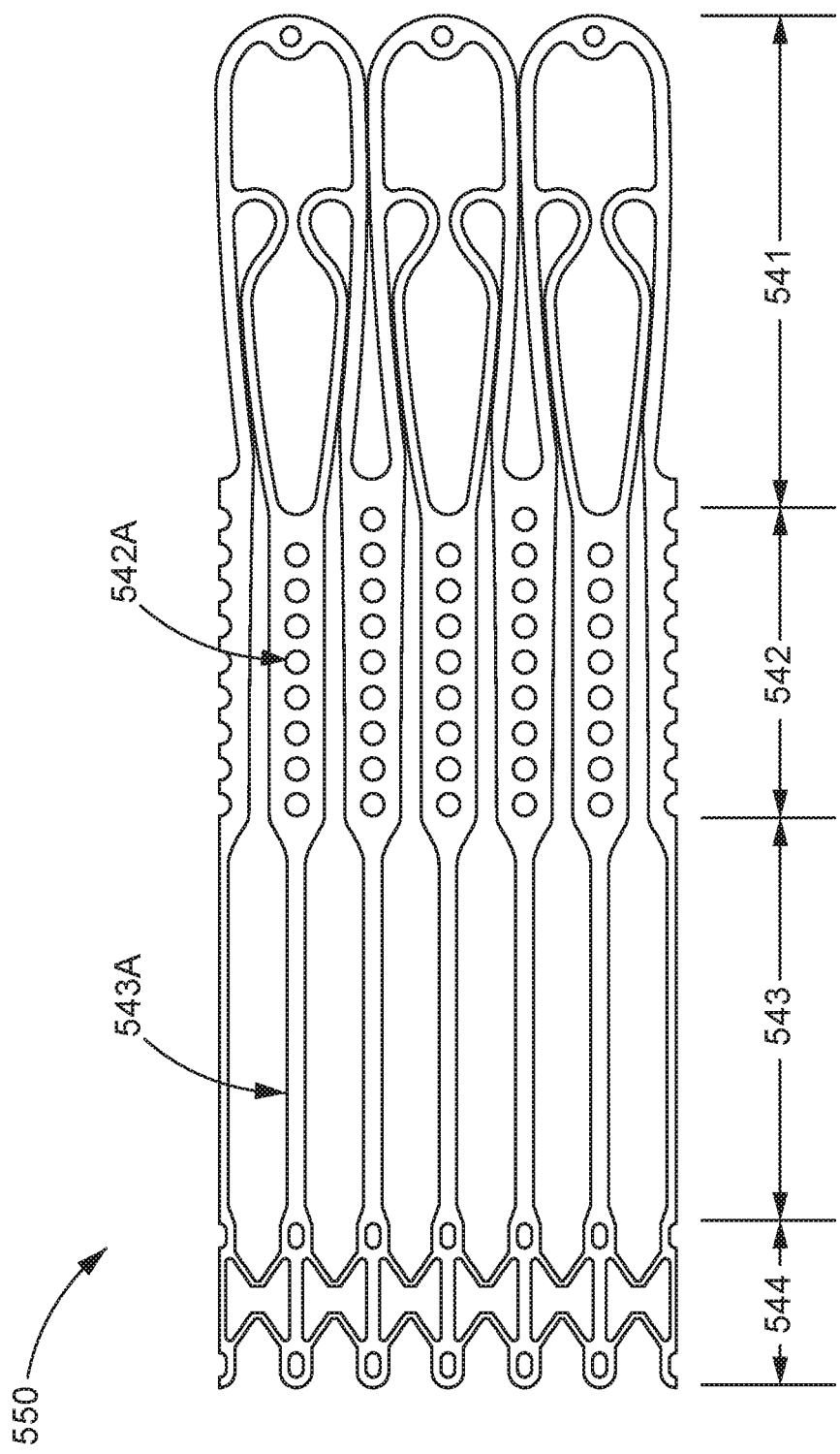
FIG. 10 is an opened and flattened view of the inner frame of the prosthetic heart valve of FIGS. 7-9, in an unexpanded configuration.
Figure 11:
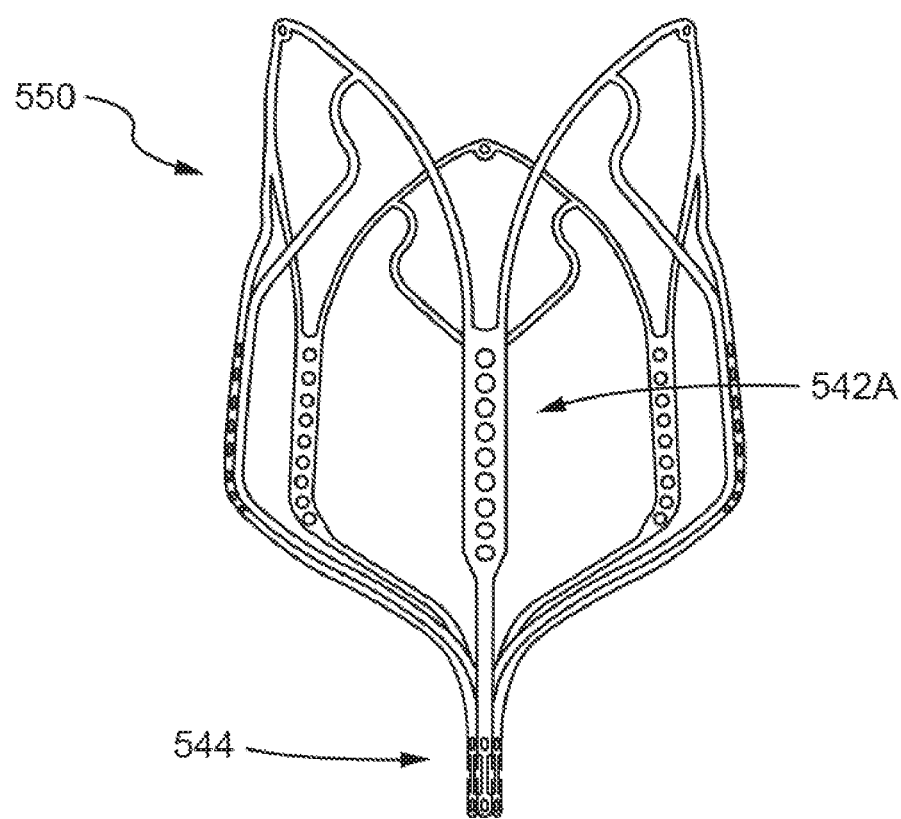
FIGS. 11 and 12 are side and bottom views, respectively, of the inner frame of FIG. 10 in an expanded configuration.
Figure 12:
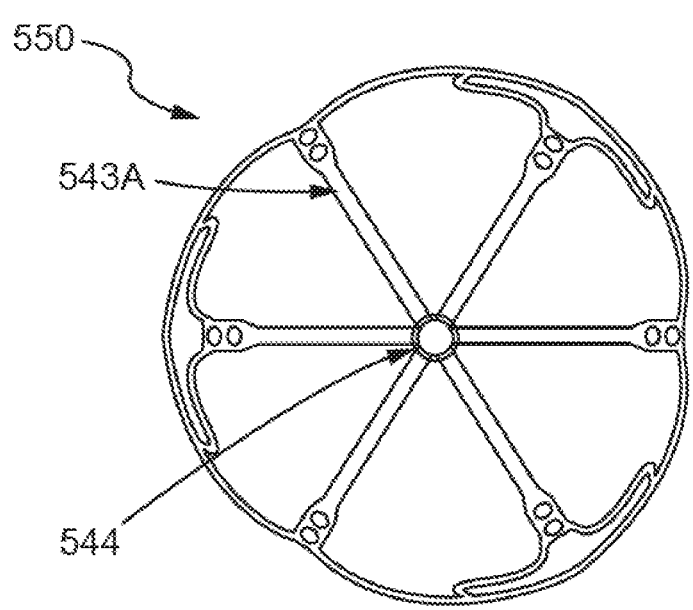

Inner frame 550 is shown in more detail in FIGS. 10-12. Specifically, FIGS. 10-12 show inner frame 550 in an undeformed, initial state (FIG. 10), a side view of the inner frame 550 in a deployed configuration (FIG. 11), and a bottom view of the inner frame 550 in a deployed configuration (FIG. 12), respectively, according to an embodiment.

In this embodiment, inner frame 550 is formed from a laser-cut tube of Nitinol®. Inner frame 550 is illustrated in FIG. 10 in an undeformed, initial state, i.e. as laser-cut, but cut and unrolled into a flat sheet for ease of illustration. Inner frame 550 can be divided into four portions, corresponding to functionally different portions of the inner frame 550 in final form: atrial portion 541, body portion 542, strut portion 543, and tether clamp or connecting portion 544. Strut portion 543 includes six struts, such as strut 543A, which connect body portion 542 to tether clamp portion 544.

Connecting portion 544 includes longitudinal extensions of the struts, connected circumferentially by pairs of opposed, slightly V-shaped connecting members (or "micro-Vs"). Connecting portion 544 is configured to be radially collapsed by application of a compressive force, which causes the micro-Vs to become more deeply V-shaped, with the vertices moving closer together longitudinally and the open ends of the V shapes moving closer together circumferentially. Thus, connecting portion 544 can be configured to compressively clamp or grip one end of a tether, either connecting directly onto a tether line (e.g. braided filament line) or onto an intermediate structure, such as a polymer or metal piece that is in term firmly fixed to the tether line.

In contrast to connecting portion 544, atrial portion 541 and body portion 542 are configured to be expanded radially. Strut portion 543 forms a longitudinal connection, and radial transition, between the expanded body portion and the compressed connecting portion 544.

Body portion 542 includes six longitudinal posts, such as post 542A. The posts can be used to attach leaflets 570 to inner frame 540, and/or can be used to attach inner assembly 540 to outer assembly 510, such as by connecting inner frame 550 to outer frame 520. In the illustrated embodiment, the posts include openings through which connecting members (such as suture filaments and/or wires) can be passed to couple the posts to other structures.

Inner frame 550 is shown in a fully deformed, i.e. the final, deployed configuration, in side view and bottom view in FIGS. 11 and 12, respectively.

Figure 13:
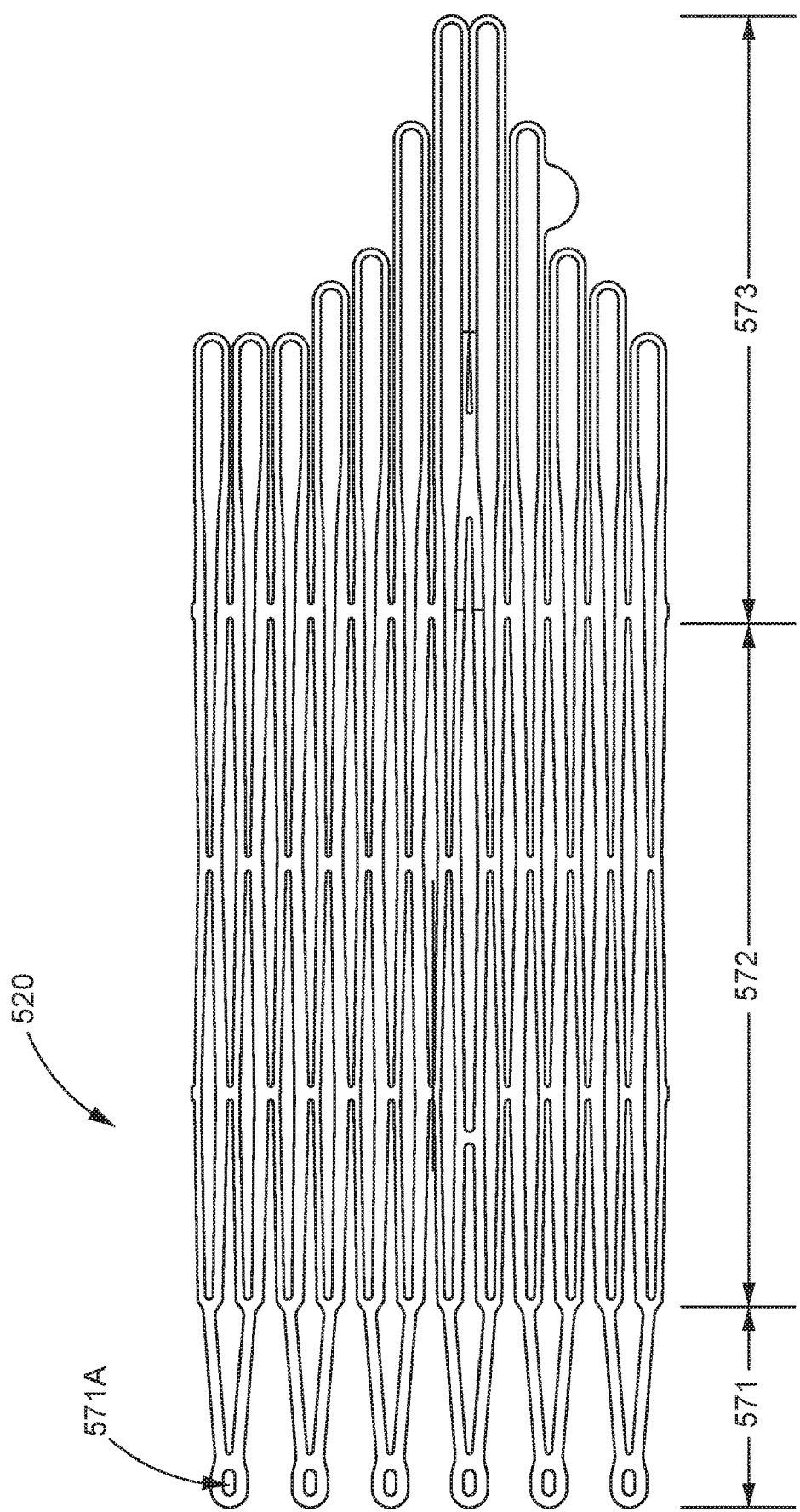
FIG. 13 is an opened and flattened view of the outer frame of the valve of FIGS. 7-9, in an unexpanded configuration.
Figure 14:
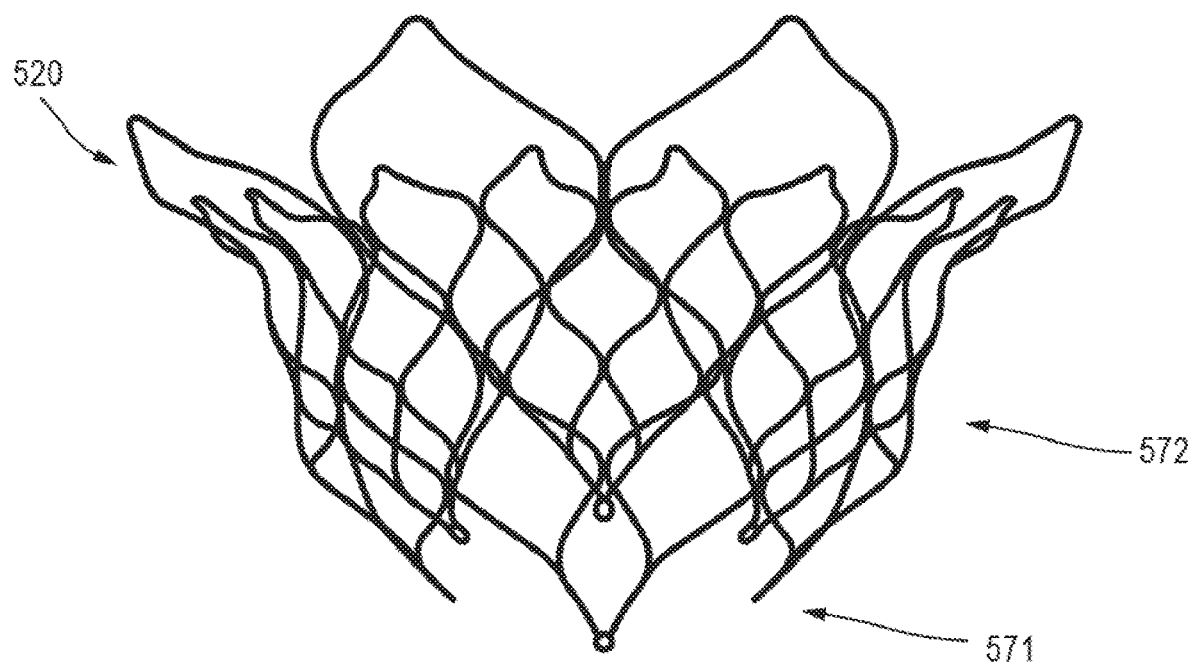
FIGS. 14 and 15 are side and top views, respectively, of the outer frame of FIG. 13 in an expanded configuration.
Figure 15:
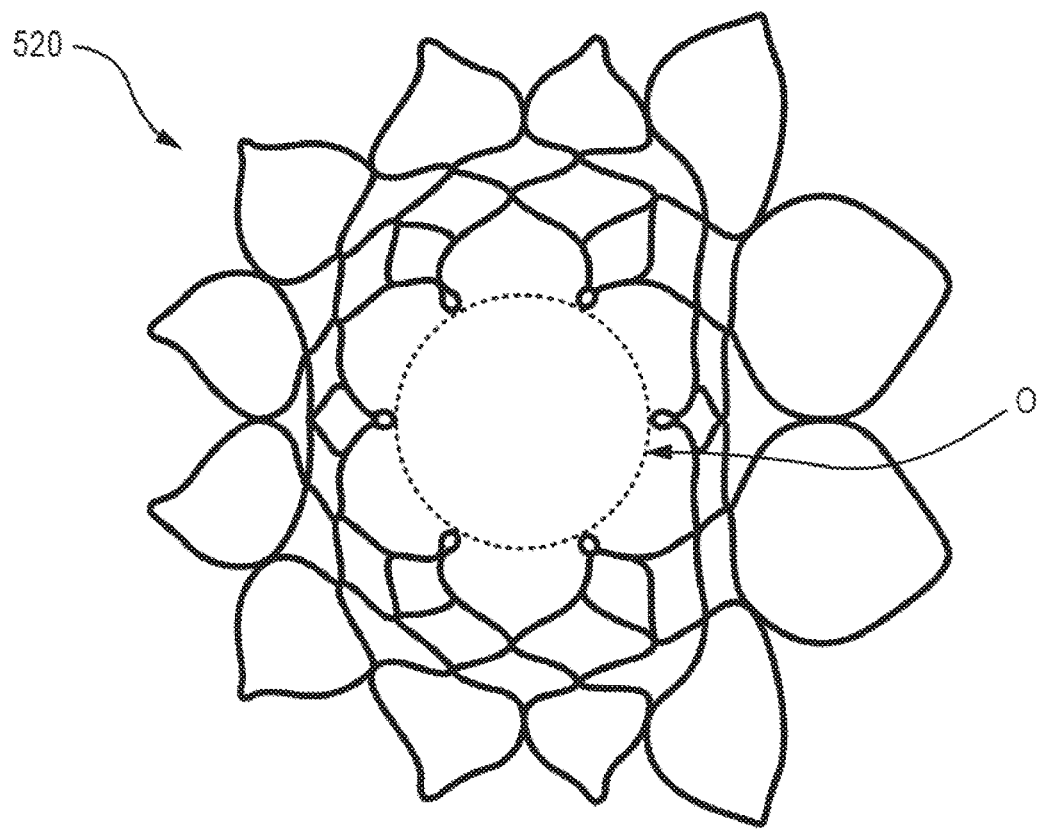

Outer frame 520 of valve 500 is shown in more detail in FIGS. 13-15. In this embodiment, outer frame 520 is also formed from a laser-cut tube of Nitinol®. Outer frame 520 is illustrated in FIG. 13 in an undeformed, initial state, i.e. as laser-cut, but cut and unrolled into a flat sheet for ease of illustration. Outer frame 520 can be divided into a coupling portion 571, a body portion 572, and a cuff portion 573, as shown in FIG. 13. Coupling portion 571 includes multiple openings or apertures, such as 571A, by which outer frame 520 can be coupled to inner frame 550, as discussed in more detail below.

Outer frame 520 is shown in a fully deformed, i.e. the final, deployed configuration, in side view and top view in FIGS. 14 and 15, respectively. As best seen in FIG. 15, the lower end of coupling portion 571 forms a roughly circular opening (identified by "O" in FIG. 15). The diameter of this opening preferably corresponds approximately to the diameter of body portion 542 of inner frame 550, to facilitate coupling of the two components of valve 500.

Figure 16:
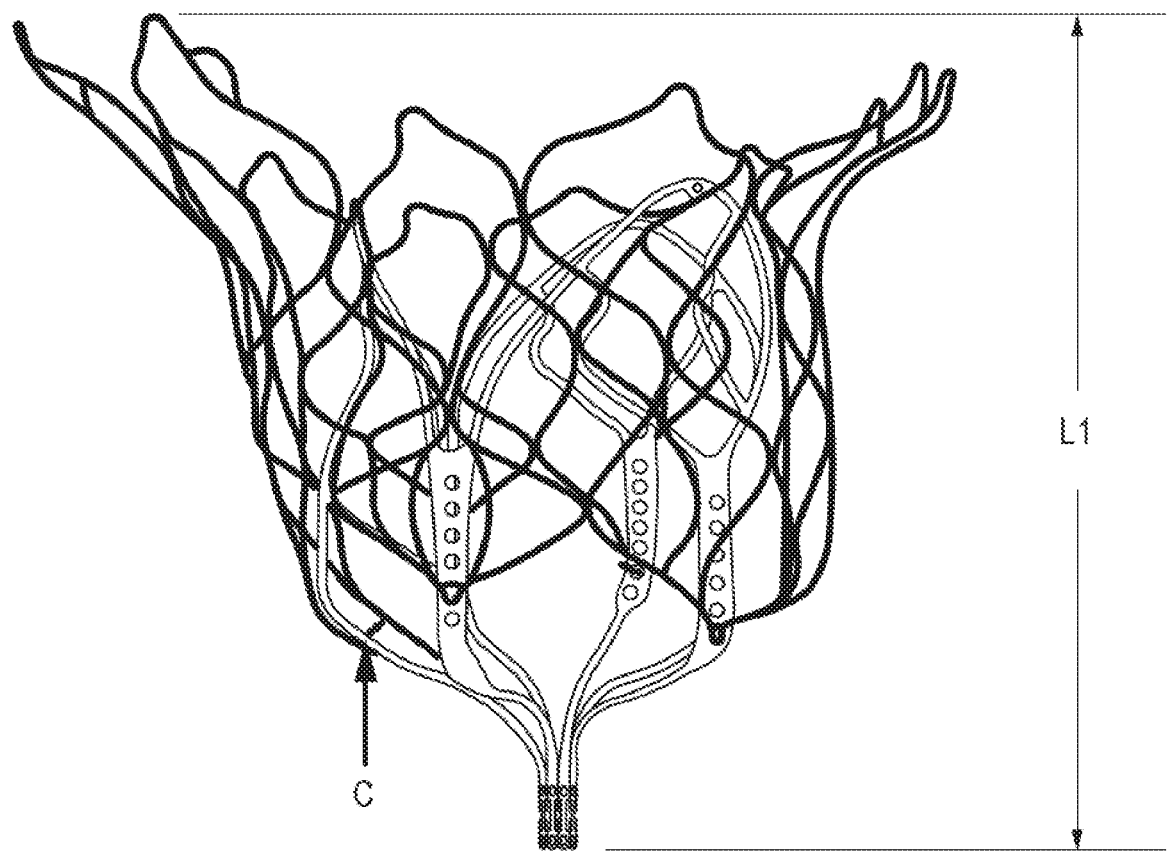
FIGS. 16-18 are side, front, and top views of an assembly of the inner frame of FIGS. 10-12 and the outer frame of FIGS. 13-15.
Figure 17:
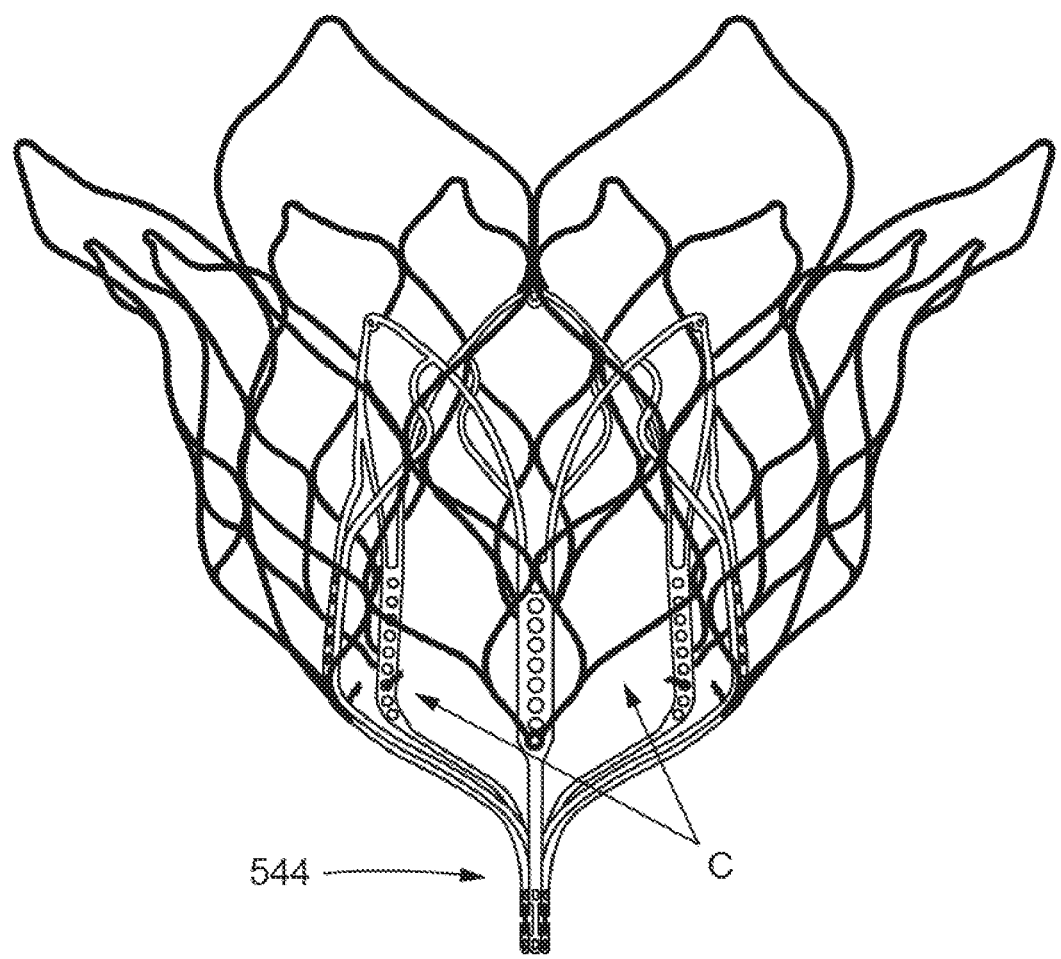
Figure 18:
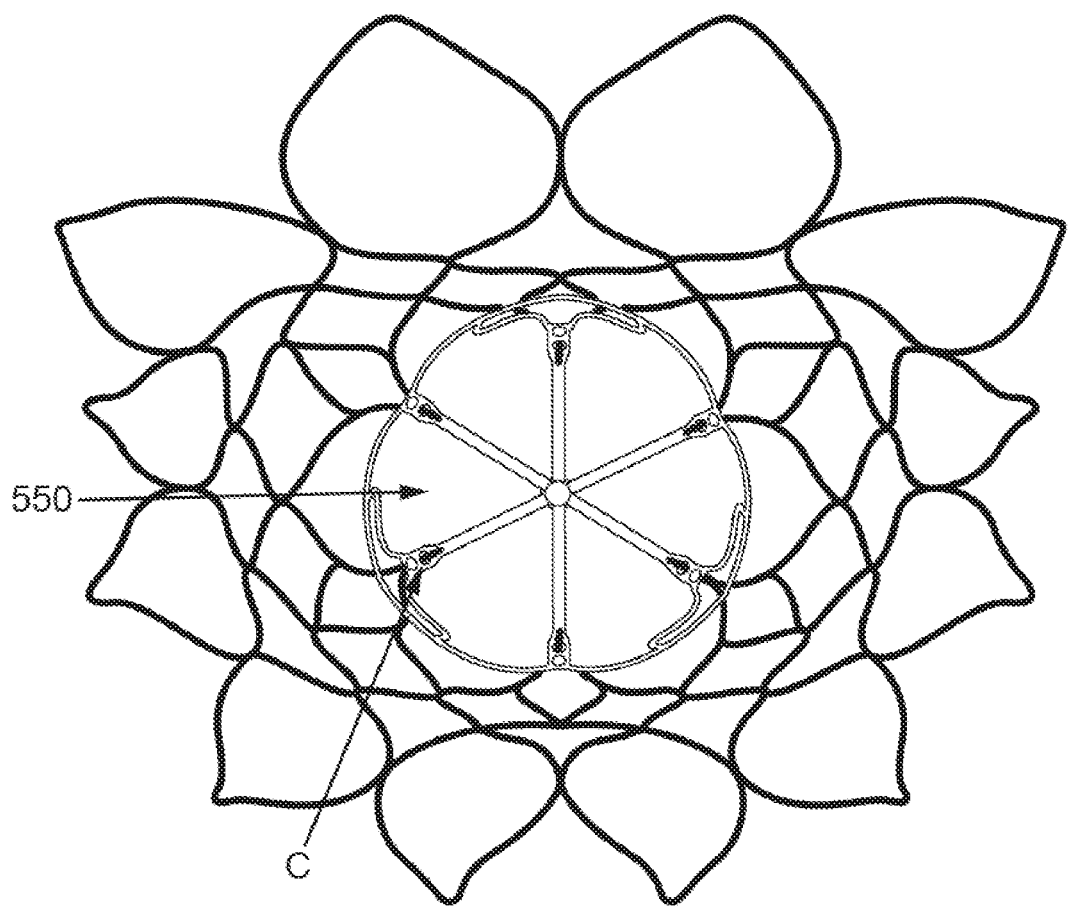

Outer frame 520 and inner frame 550 are shown coupled together in FIGS. 16-18, in front, side, and top views, respectively. The two frames collectively form a structural support for a prosthetic valve such as valve 500. The frames support the valve leaflet structure (e.g., leaflets 570) in the desired relationship to the native valve annulus, support the coverings (e.g., outer covering 530, inner covering 532, outer covering 560) for the two frames to provide a barrier to blood leakage between the atrium and ventricle, and couple to the tether (e.g., tether assembly 590) (by the inner frame 550) to aid in holding the prosthetic valve in place in the native valve annulus by the tether connection to the ventricle wall. The outer frame 520 and the inner frame 550 are connected at six coupling points (representative points are identified as "C"). In this embodiment, the coupling points are implemented with a mechanical fastener, such as a short length of wire, passed through an aperture (such as aperture 571A) in coupling portion 571 of outer frame 520 and corresponding openings in longitudinal posts (such as post 542A) in body portion 542 of inner frame 550. Inner frame 550 is thus disposed within the outer frame 520 and securely coupled to it.

FIGS. 19-25 illustrate a method of reconfiguring a prosthetic heart valve 300 (e.g., prosthetic mitral valve) prior to inserting the prosthetic heart valve 300 into a delivery sheath 326 (see, e.g., FIGS. 21-25) for delivery into the heart via the femoral vein. The prosthetic heart valve 300 (also referred to herein as "valve") can be constructed the same as or similar to, and function the same as or similar to the valve 500 described above. Thus, some details regarding the valve 300 are not described below. It should be understood that for features and functions not specifically discussed, those features and functions can be the same as or similar to the valve 500.

Figure 19:
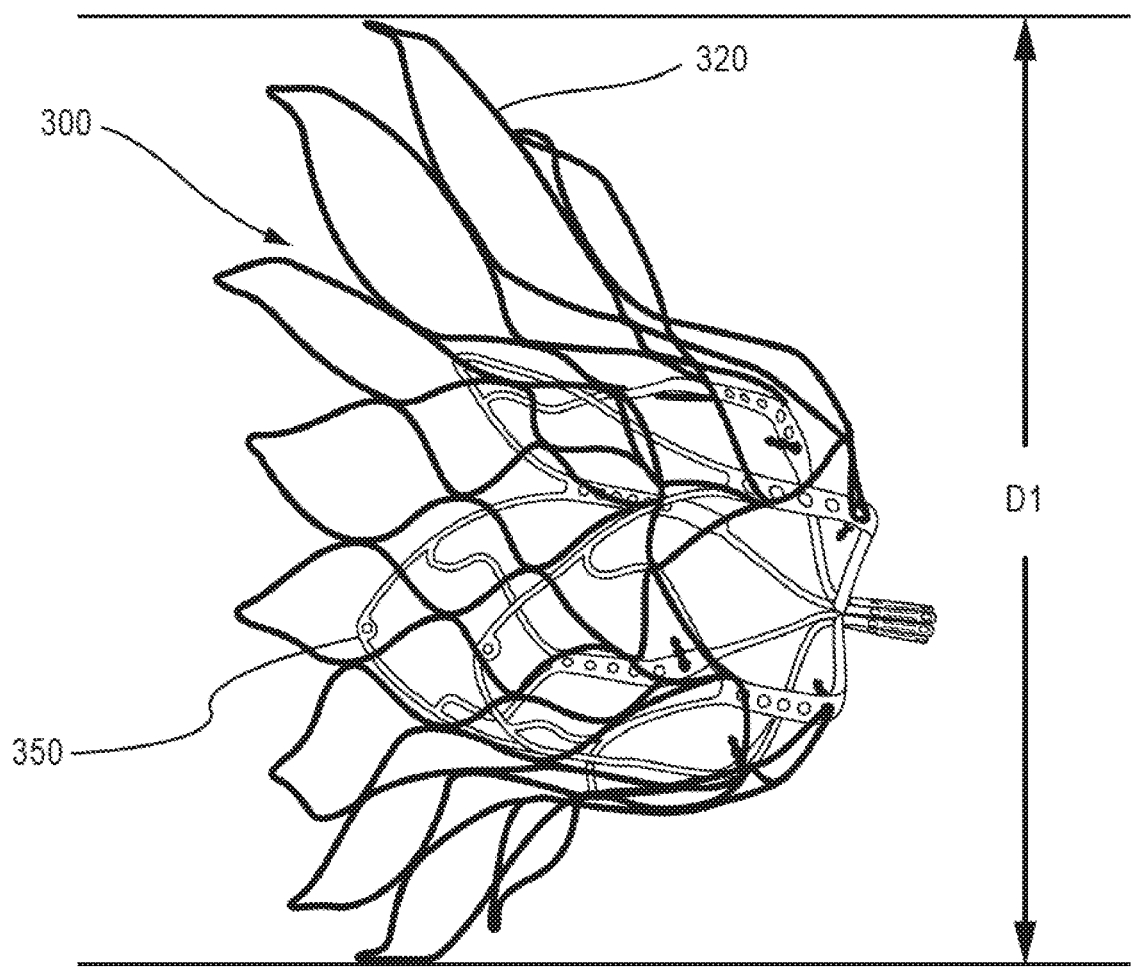
FIG. 19 is a side perspective view of the assembly of the inner frame of FIGS. 10-12 and the outer frame of FIGS. 13-15 shown in a biased expanded configuration.
Figure 20:
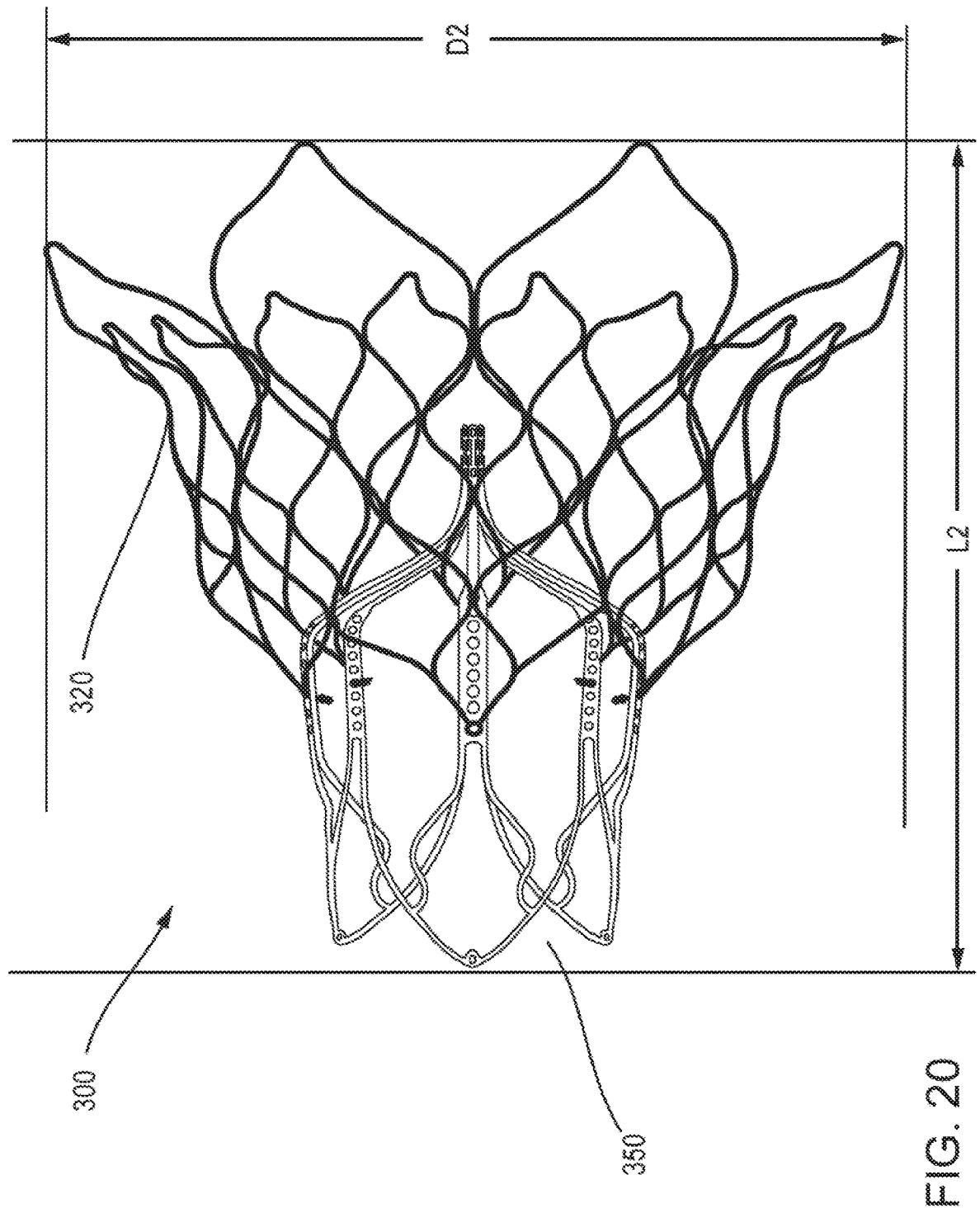
FIG. 20 is a side perspective view of the assembly of FIG. 19 with the outer frame shown inverted.
Figure 21:
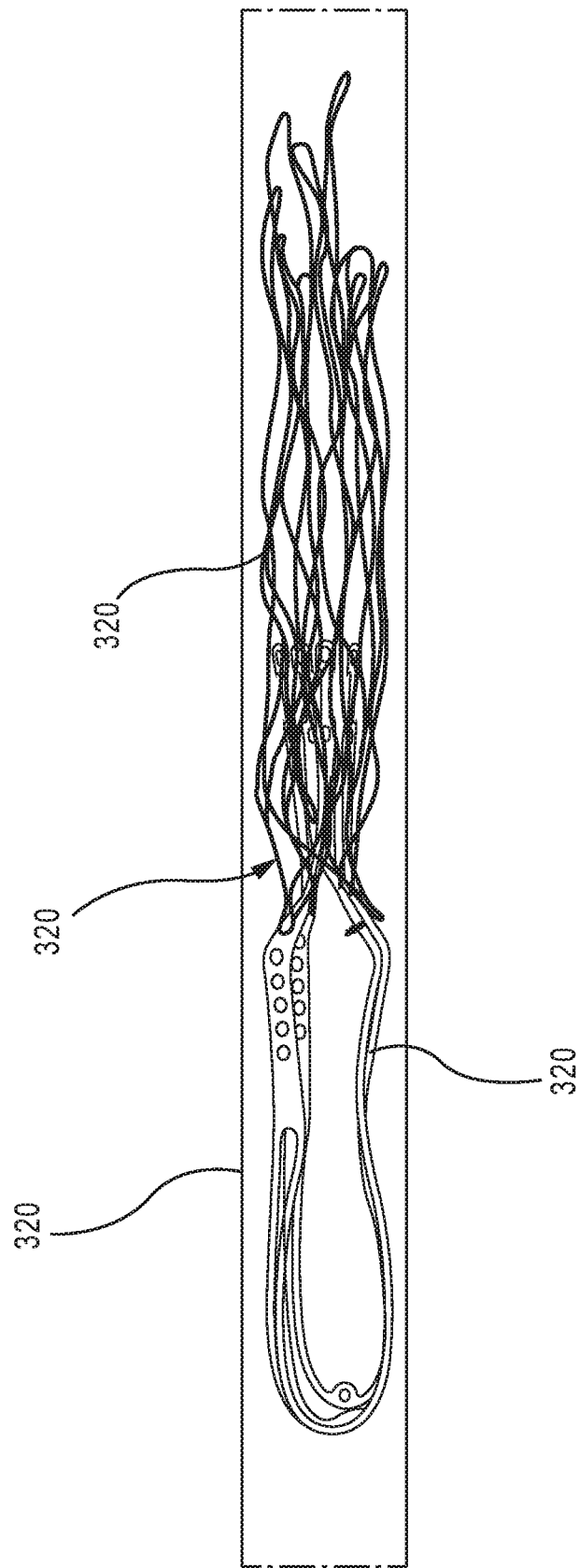
FIG. 21 is side view of the assembly of FIG. 20 shown in a collapsed configuration within a lumen of a delivery sheath.

As shown in FIG. 19, the valve 300 has an outer frame 320 and an inner frame 350. As discussed above for valves 200 and 500, the outer frame 320 and the inner frame 350 of valve 300 can each be formed with a shape-memory material and have a biased expanded or deployed configuration. The outer frame 320 and the inner frame 350 can be moved to a collapsed or undeployed configuration for delivery of the valve 300 to the heart. In this example method of preparing the valve 300 for delivery to the heart, the outer frame 320 of the valve 300 is first disposed in a prolapsed or inverted configuration as shown in FIG. 20. Specifically, the elastic or superelastic structure of outer frame 320 of valve 300 allows the outer frame 320 to be disposed in the prolapsed or inverted configuration prior to the valve 300 being inserted into the lumen of the delivery sheath 326. As shown in FIG. 20, to dispose the outer frame 320 in the inverted configuration, the outer frame 320 is folded or inverted distally such that the outer frame 320 is pointed away from the inner frame 350. In this inverted configuration, the overall outer perimeter or outer diameter of the valve 300 is reduced and the overall length is increased. For example, the diameter D1 shown in FIG. 19 is greater than the diameter D2 shown in FIG. 20, and the length L1 in FIG. 16 is less than the length L2 in FIG. 20. With the outer frame 320 in the inverted configuration, the valve 300 can be placed within a lumen of a delivery sheath 326 as shown in FIG. 21 for delivery of the valve 300 to the left atrium of the heart. By disposing the outer frame 320 in the inverted configuration, the valve 300 can be collapsed into a smaller overall diameter, i.e. placed in a smaller diameter delivery sheath, than would be possible if the valve 300 in the configuration shown in FIG. 19 were collapsed radially. This is because in the configuration shown in FIG. 19, the two frames are concentric, and thus the outer frame 320 must be collapsed around the inner frame 350, whereas in the configuration shown in FIG. 20, the two frames are coaxial but not concentric, such that the outer frame 320 can be collapsed without needing to accommodate the inner frame 350 inside it.

The procedure to deliver the valve 300 to the heart can be the same as or similar to the procedure described with reference to FIGS. 1-6. In this embodiment, the valve 300 is not partially deployed outside of the lumen of the delivery sheath 326 prior to being inserted into a femoral puncture, through the femoral vein, through the inferior vena cava, into the right atrium, through the septum Sp and into the left atrium LA of the heart. With the distal end portion of the delivery sheath 326 disposed within the left atrium of the heart, the valve 300 can be deployed outside of the delivery sheath 326. For example, although not shown, a tether such as tether 236 described above for valve 200 can be attached to the valve 300 and used to pull the valve 300 out of the lumen of the delivery sheath 326. Alternatively, or in addition to, a pusher device (not shown) can be used to deploy the valve 300. Thus, as described above for valve 200, the valve 300 can be deployed by pushing with the pusher device, pulling with the tether, or both.

Figure 22:
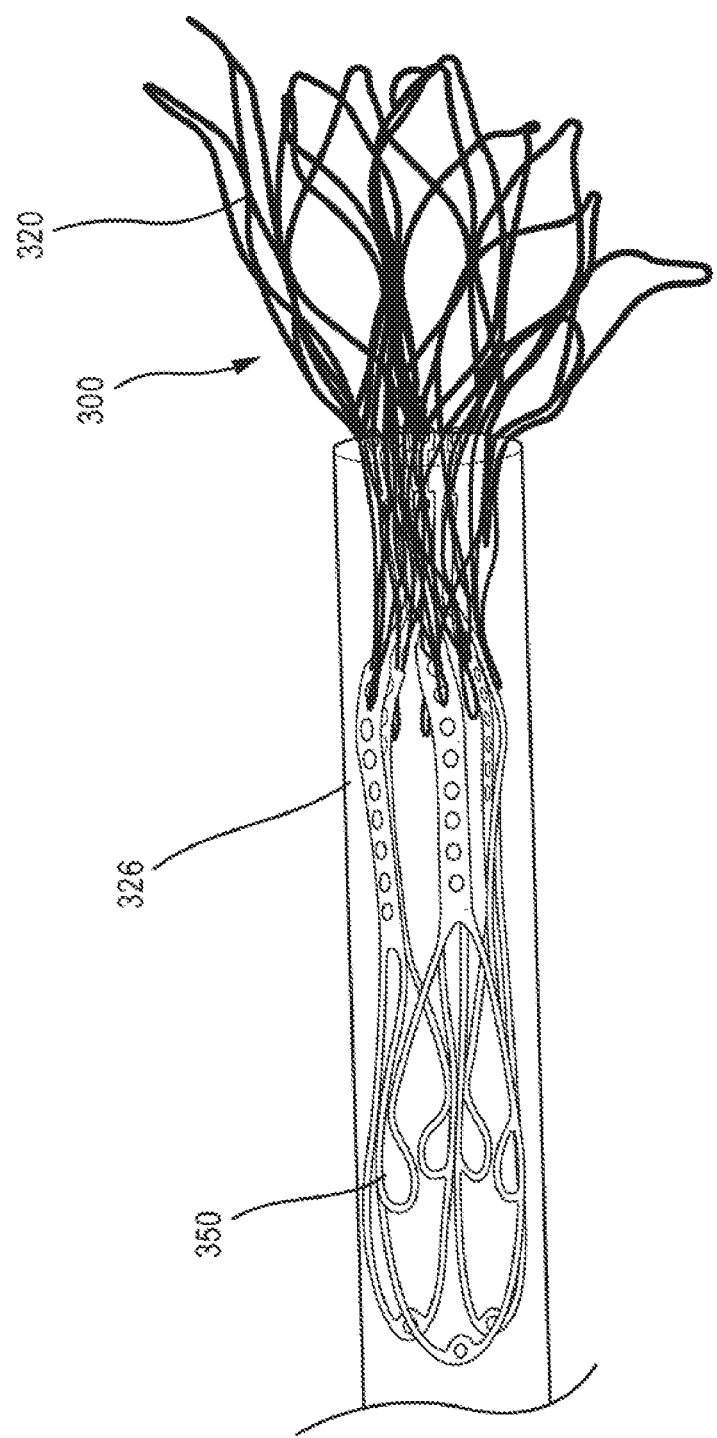
FIG. 22 is a side view of the assembly of FIG. 21 shown in a first partially deployed configuration.
Figure 23:
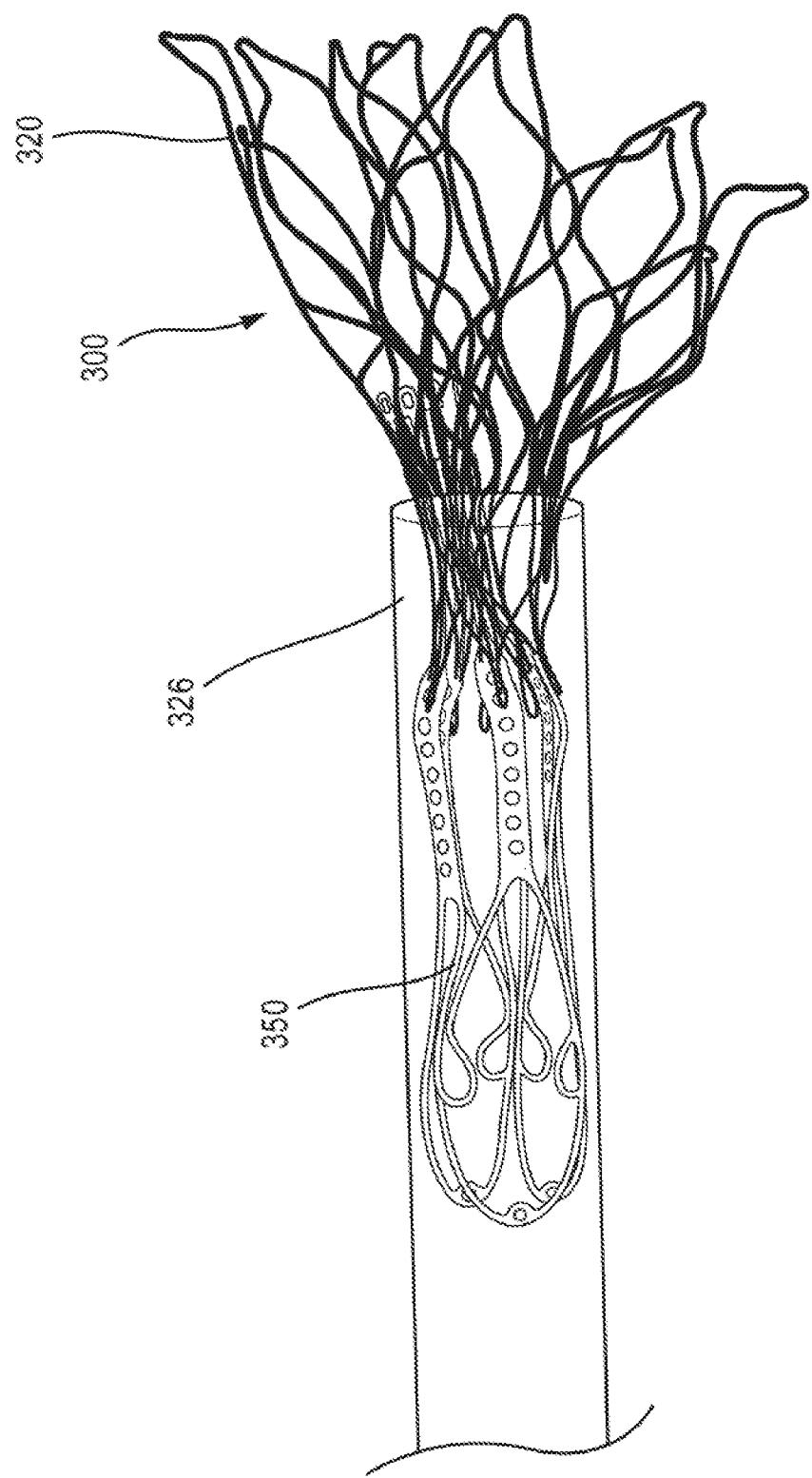
FIG. 23 is a side view of the assembly of FIG. 21 shown in a second partially deployed configuration.
Figure 24:
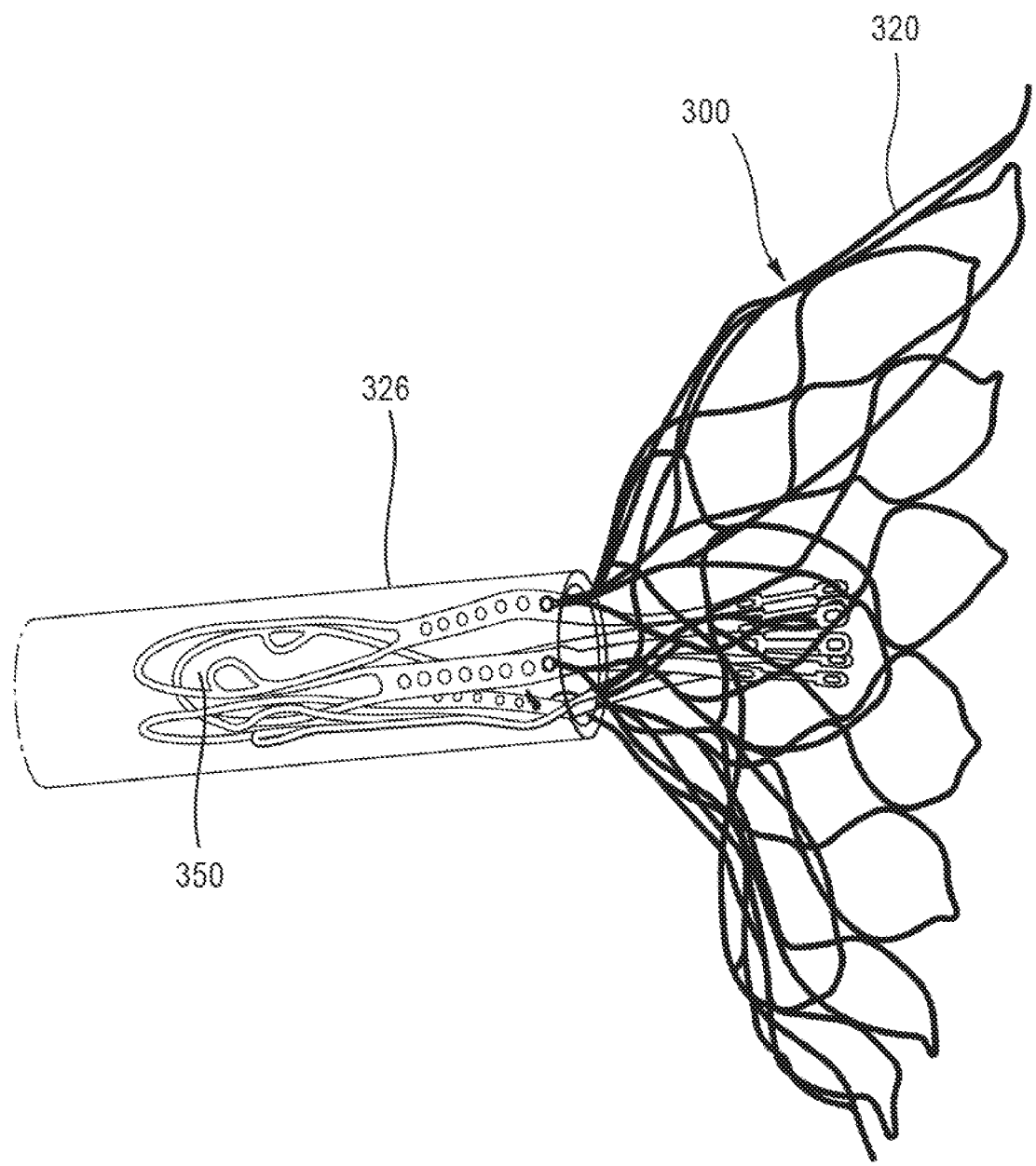
FIG. 24 is a side view of the assembly of FIG. 21 shown in a third partially deployed configuration in which the inverted outer frame is substantially deployed outside of the delivery sheath.
Figure 25:
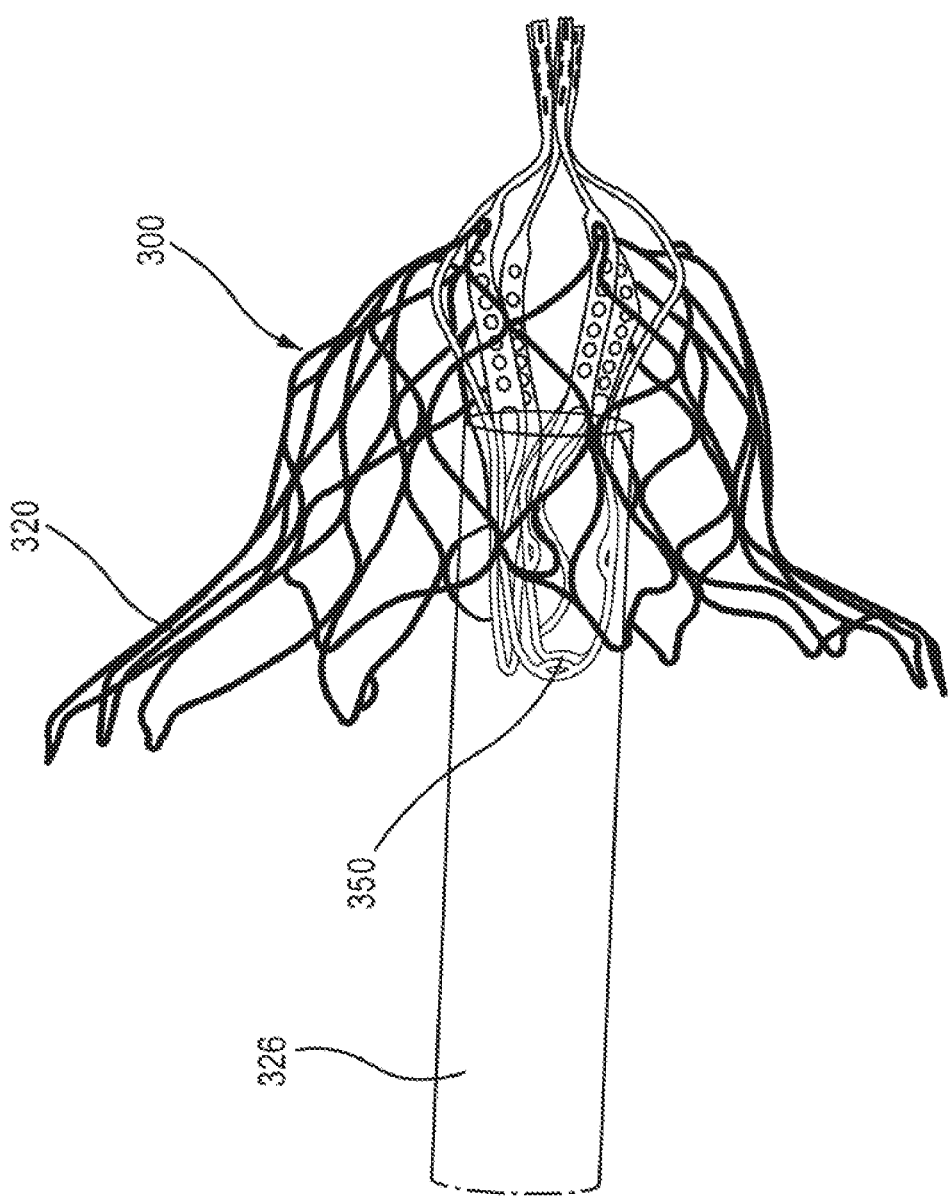
FIG. 25 is a side view of the assembly of FIG. 21 shown in a fourth partially deployed configuration in which the outer frame has reverted and assumed a biased expanded configuration.

As the valve 300 exits the lumen of the delivery sheath 326, the outer frame assembly 310 exits first in its inverted configuration as shown in the progression of FIGS. 22-24. After the outer frame assembly 310 is fully outside of the lumen of the delivery sheath 326, the outer frame 320 can revert to its expanded or deployed configuration as shown in FIG. 25. In some embodiments, the pusher device and/or the tether can be used to aid in the reversion of the outer frame assembly 310. The valve 300 can continue to be deployed until the inner frame 350 is fully deployed with the left atrium and the valve 300 is in the expanded or deployed configuration (as shown in FIG. 19).

Figure 27:
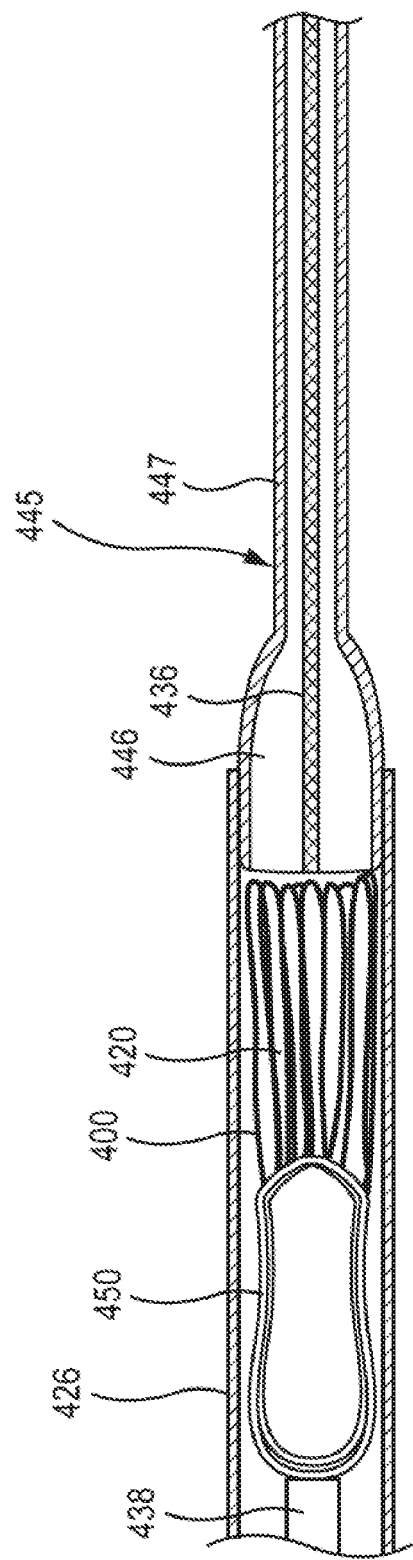
FIG. 27 is a side view of a prosthetic mitral valve in a collapsed configuration within a lumen of a portion of a delivery sheath and a balloon dilator device coupled to the delivery sheath.
Figure 28:
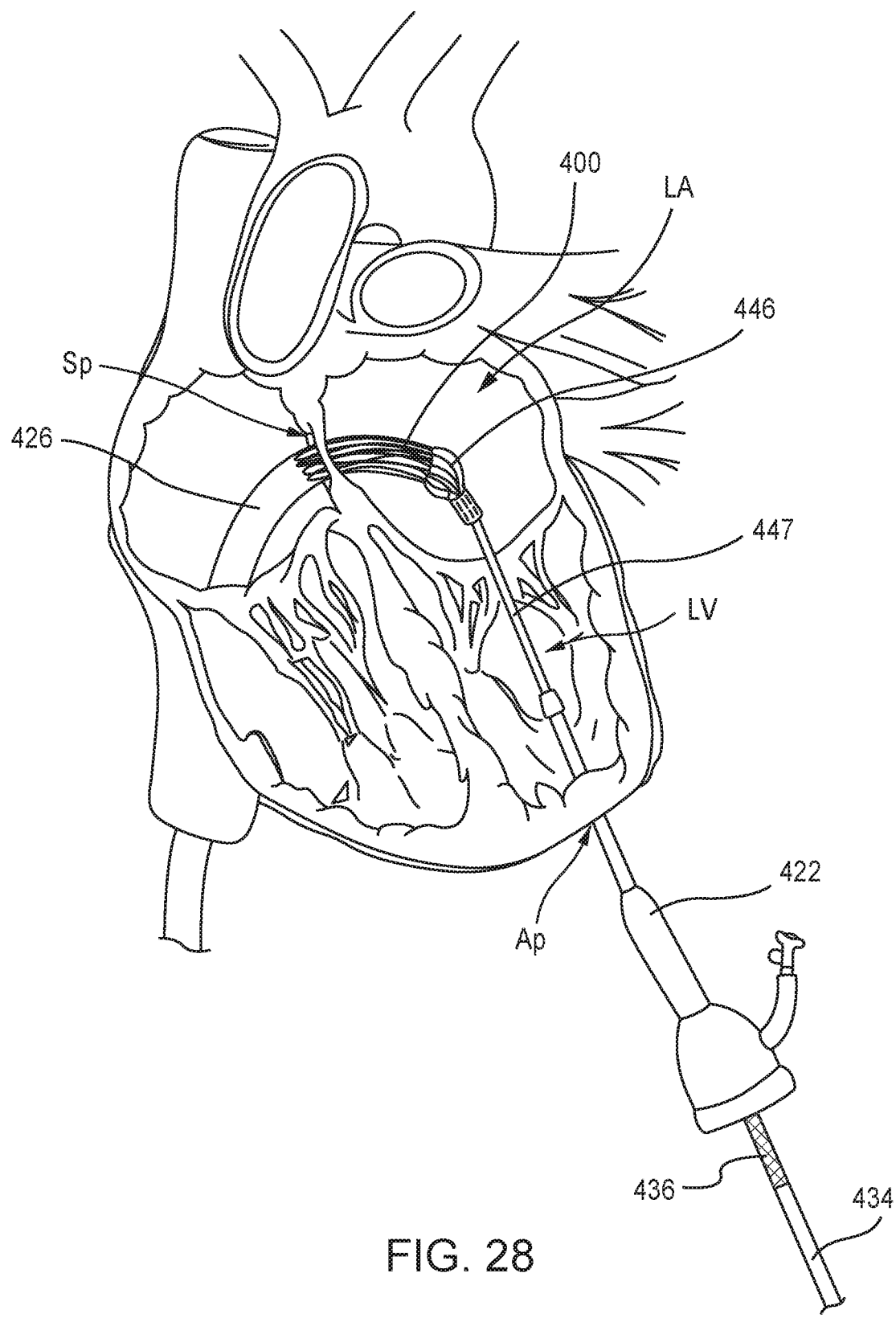
FIG. 28 is a cross-sectional illustration of a heart with the delivery sheath and balloon dilator device of FIG. 27 at a stage of a procedure to deliver and deploy the prosthetic mitral valve disposed within the delivery sheath.

FIGS. 27 and 28 illustrate an optional balloon dilator device that can be used during a procedure for transfemoral delivery of a prosthetic heart valve to the heart. FIG. 27 illustrates a valve 400 disposed within a lumen of a delivery sheath 426. The valve 400 can be constructed the same as or similar to, and function the same as or similar to, the valves 200, 500 and 300 described above. For example, the valve 400 can include an outer frame 420 and an inner frame 450 as described above for previous embodiments. A tether 436 can be coupled to the valve 400 and a valve leader member 434 (see FIG. 28) can be coupled to the tether 436.

In this embodiment, to deliver the valve 400, a leader tube (not shown) can be inserted through an apical puncture and extended through the heart and out through a femoral vein access site. A valve leader member 434 coupled to a tether 436 can be inserted through the femoral end of the leader tube and extended out the apical end of the leader tube, as described above with respect to FIGS. 1-6. The valve 400 can be loaded into the distal end of a lumen of a delivery sheath 426 either before or after the tether 436 and valve leader member 434 are looped through the patient. A balloon dilator device 445 can then be advanced along the valve leader member 434 from the apical end, through the heart, through the femoral vein and out the femoral access site.

The balloon dilator device 445 includes a balloon member 446 that can be disposed at least partially within the distal end portion of the lumen of the delivery device 426, and distal of the valve 400, as shown in FIG. 27. The balloon dilator device 445 also includes an elongate member 447 coupled to the balloon member 446 and that defines an inflation lumen in fluid communication with an interior of the balloon member 446. The elongate member 447 can be coupled to a source of an inflation medium (not shown) configured to supply the inflation medium to the balloon member 446. With the balloon dilator device 445 coupled to the delivery sheath 426 as shown in FIG. 27, the balloon member 446 can be inflated. The delivery sheath 426 can then be inserted through the femoral access site and advanced through the femoral vein, through the inferior vena cava, into the right atrium, through the septum Sp and into the left atrium LA as shown in FIG. 28. The balloon member 446 provides a smooth surface to aid in maneuvering the delivery sheath 426 through the femoral vein and the septum and into the heart. With the distal end portion of the delivery sheath 426 disposed within the left atrium LA, the balloon member 446 can be deflated and removed through the apical access site. The valve 400 can then be deployed and positioned within the mitral annulus as described above for FIGS. 1-6. For example, a pusher device 438 (see FIG. 27) can be used to push the valve 400 out of the lumen of the delivery sheath 426 and/or the tether 436 coupled to the valve 400 can be pulled.

Figure 29:
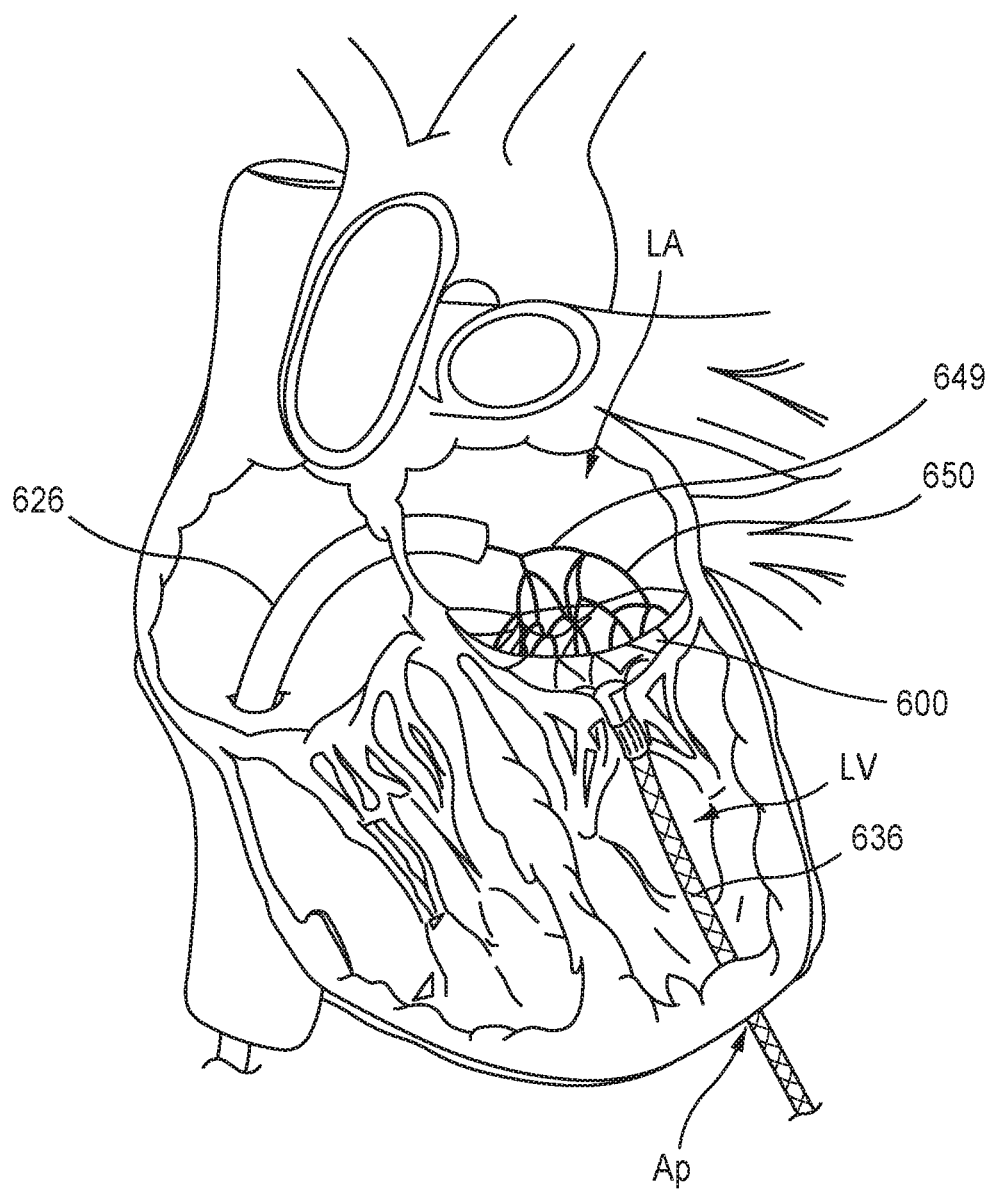
FIG. 29 is a cross-sectional illustration of a heart with a portion of a delivery sheath shown after deploying a prosthetic mitral valve with the assistance of a wire assist structure, according to an embodiment.
Figure 30:
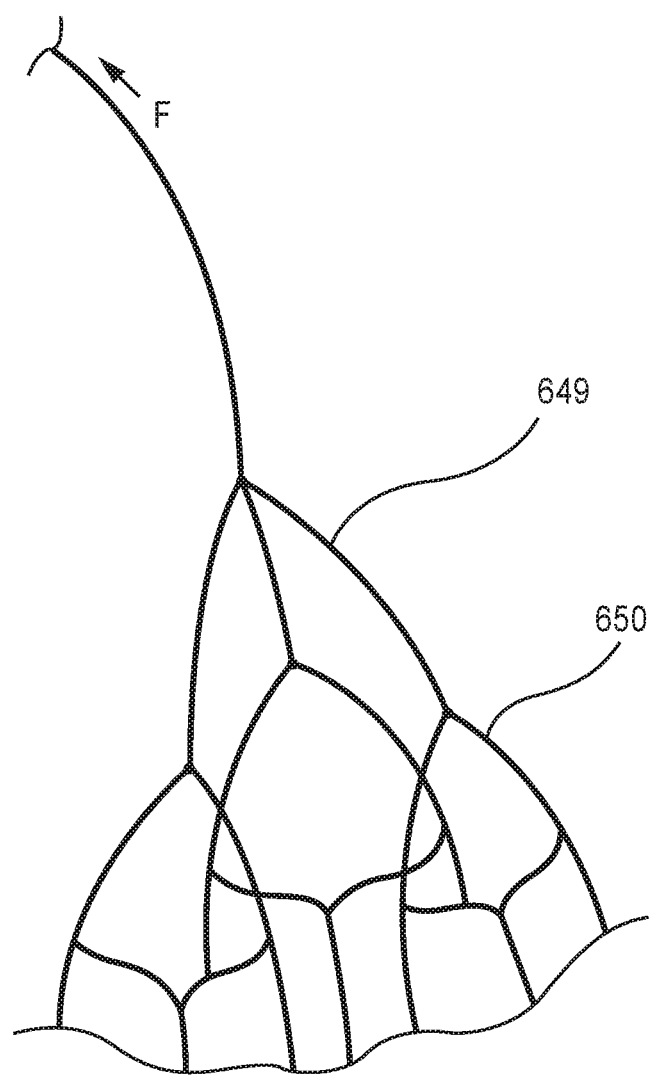
FIG. 30 is a perspective view of the wire assist structure of FIG. 29 coupled to a portion of a prosthetic mitral valve, according to an embodiment.

FIGS. 29 and 30 illustrate an optional wire assist structure that can be used during a procedure to deliver a prosthetic heart valve transfemorally as described above for previous embodiments. A wire assist structure 649 can be releasably coupled to a valve 600 as shown in FIG. 29. The valve 600 can be constructed the same as or similar to, and function the same as or similar to, the valves described above for previous embodiments. For example, the valve 600 can include an outer frame 620 and an inner frame 650. The wire assist structure 649 can be releasably coupled to the inner frame 650 as best shown in FIG. 30. For example, releasable connectors (not shown) can be used to couple the wire assist structure 649 to the inner frame 650.

In use, the wire assist structure 649 can be movably disposed within a delivery sheath 626 used to deliver the valve 600 to the heart. The wire assist structure 649 can hold the inner frame 650 and allow for positioning control of the valve 600 (i.e., clocking and advancement) while the outer frame 650 of the valve 600 is fully expanded, which allows the valve 600 to be functioning during the positioning phase. When the valve 600 is in the desired final position, the wire assist structure 649 can be released from the inner frame 650 and removed with the delivery sheath 626.

Figure 31:
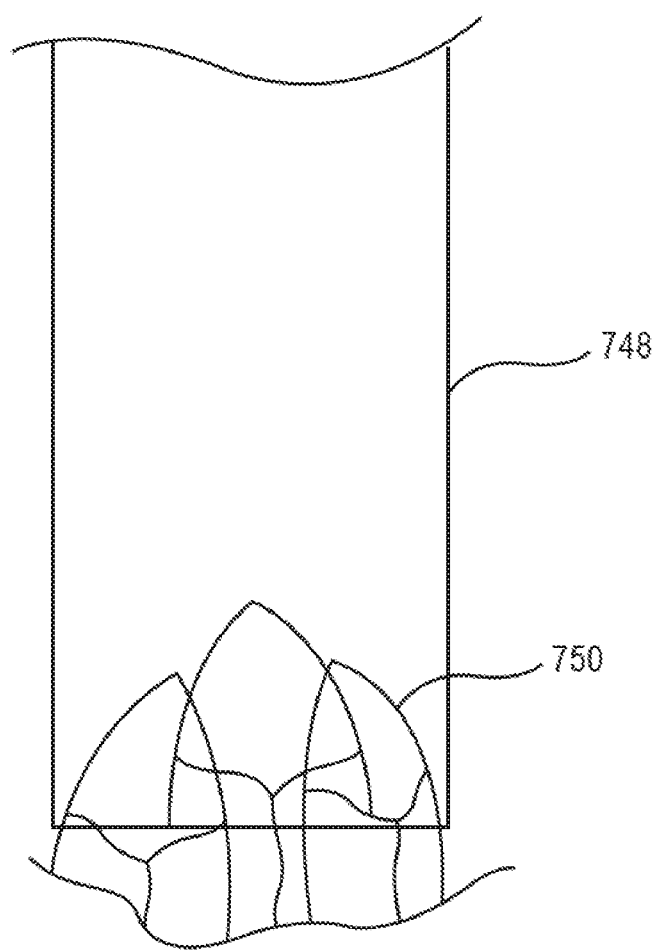
FIG. 31 is a perspective view of an assist member coupled to a portion of a prosthetic mitral valve, according to an embodiment.

FIG. 31 illustrates another optional assist member that can be used during a procedure to deliver a prosthetic heart valve transfemorally. An assist member 748 can be in the form of a tubular member defining a lumen with a diameter sized to receive at least a portion of the inner frame 750 of a valve 700. The valve 700 can be constructed the same as or similar to, and function the same as or similar to, the valves described above for previous embodiments. For example, the valve 700 can include an outer frame (not shown) and the inner frame 750 as described above for previous embodiments.

In use, the assist member 748 can be movably disposed within a delivery sheath (not shown) used to deliver the valve 700 and be disposed over at least a portion of the inner valve assembly 740. As with the wire assist structure 649, the assist member 748 can hold the inner frame 750 in a small compact configuration and allow for positioning control of the valve 700 (i.e., clocking and advancement) while the outer frame of the valve 700 is being expanded. This can in some cases allow the valve 700 to be functioning (or at least partially functioning) during the positioning phase of the valve 700. With the inner frame 750 held in a compact or small diameter form factor, the valve 700 can be more easily positioned to help seal the annulus with the outer frame (not shown) of the valve 700. When the valve 700 is in the desired final position, the assist member 748 can be removed.

Figure 32:
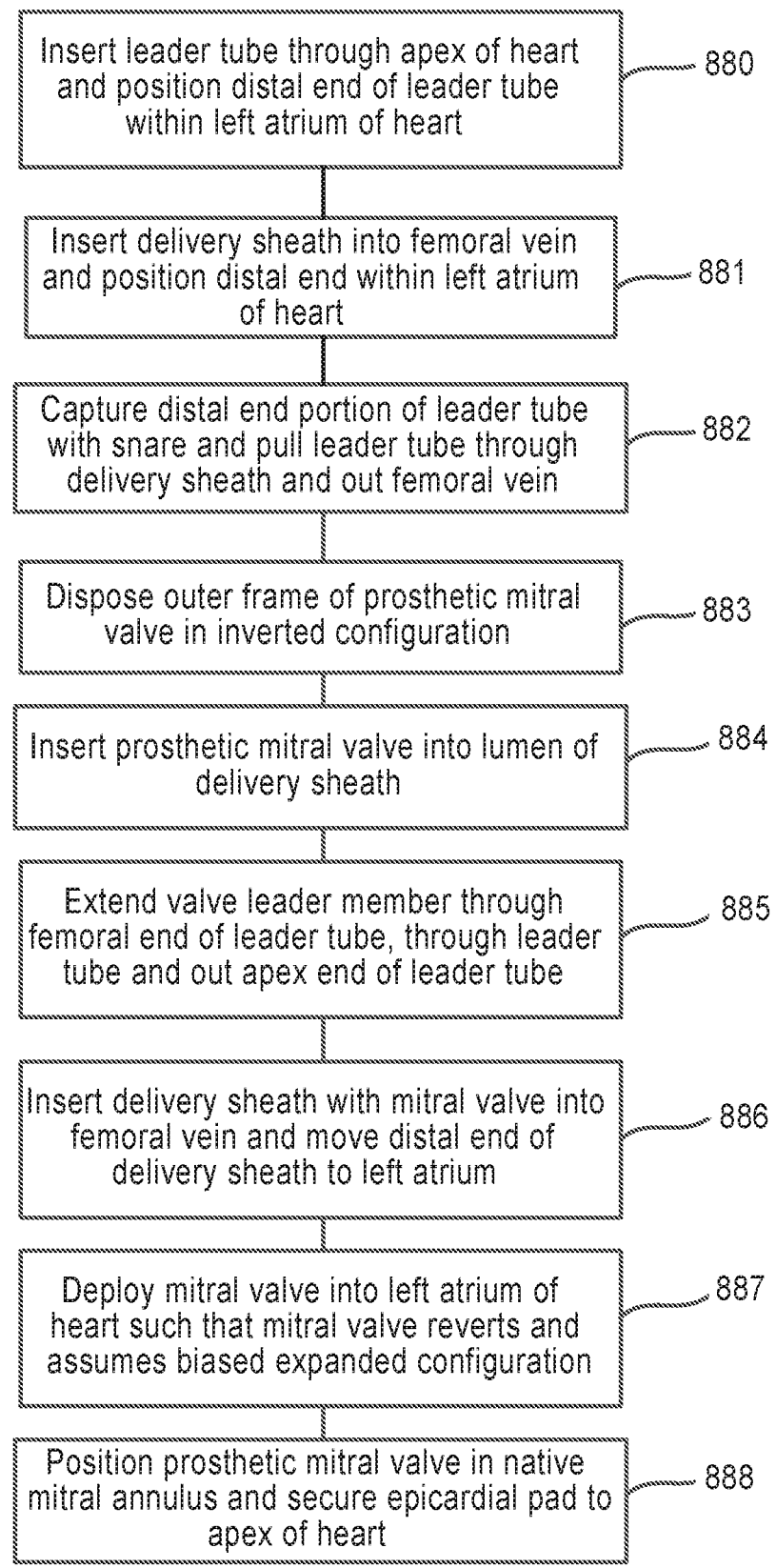
FIG. 32 is a flowchart illustrating a method of delivering a prosthetic mitral valve via a femoral vein, according to an embodiment.

FIG. 32 is a flowchart illustrating a method of deploying a prosthetic mitral valve to a heart using a transfemoral delivery approach. The method includes at 880, inserting a leader tube through an access site on the skin of the patient, through an access puncture site on the apex of the heart, and positioning a distal end portion of the leader tube in the left atrium of the heart. At 881, inserting a delivery sheath with a snare device coupled thereto through an access site into the femoral vein and into the left atrium of the heart. At 882, the leader tube is captured with the snare device, and pulled through the femoral vein such that the leader tube extends between the apex of the heart and the entry to the femoral vein. At 883, an outer frame of a prosthetic mitral valve is disposed in an inverted configuration when the mitral valve is in a biased expanded configuration. For example, the prosthetic mitral valve can be formed with a shape-memory material and have a biased expanded configuration.

At 884, after inverting the outer frame, the prosthetic mitral valve is inserted into a lumen of a delivery sheath such that the prosthetic mitral valve is moved to a collapsed configuration. The delivery sheath can be the same delivery sheath as used with the snare device or a different delivery sheath. At 885, a valve leader member is inserted to the leader tube at the femoral end of the leader tube, and moved through the leader tube until the valve leader member exits the leader tube outside of the apex of the heart. A proximal end of the valve leader member is coupled to a tether line that in turn is coupled to the prosthetic mitral valve and disposed within the delivery sheath. At 886, the delivery sheath is inserted into the femoral vein and moved through the femoral vein and through a septum of a heart until a distal end portion of the delivery sheath is disposed in the left atrium of the heart. At 887, the prosthetic mitral valve is moved distally out of the delivery sheath such that the inverted outer frame of the prosthetic mitral valve reverts, and the prosthetic mitral valve assumes its biased expanded configuration. At 888, the prosthetic mitral valve is positioned within a mitral annulus of the heart and optionally an epicardial pad device can be secured to the apex of the heart to maintain the prosthetic mitral valve in the desired position (e.g., orientation) within the mitral annulus. In some embodiments, rather than securing the prosthetic mitral valve with a tether and epicardial pad, the prosthetic mitral valve can be secured with clips or other coupling methods to a portion(s) of the ventricular wall of the heart.

FIGS. 33-37 illustrate an embodiment of an expandable epicardial pad device that can be used to secure a tether attached to a prosthetic mitral valve to the heart, for example, at the apex of the heart. An epicardial pad device 939 (also referred to herein as "epicardial pad" or "pad") can be used, for example, during a procedure to deliver a prosthetic heart valve transfemorally as described herein. The epicardial pad 939 can be formed with a small profile such that the epicardial pad 939 can be delivered to the exterior of the heart via a small incision and a small diameter delivery catheter or sheath 963 (see FIGS. 33 and 34). In some embodiments, the delivery sheath 963 can have a diameter, for example, in the range of 3-5 mm An inner delivery sheath 964 can be movably disposed within a lumen of the delivery sheath 963 and used to hold the tether 936 while the epicardial pad 939 is being deployed as described in more detail below.

Figure 34:
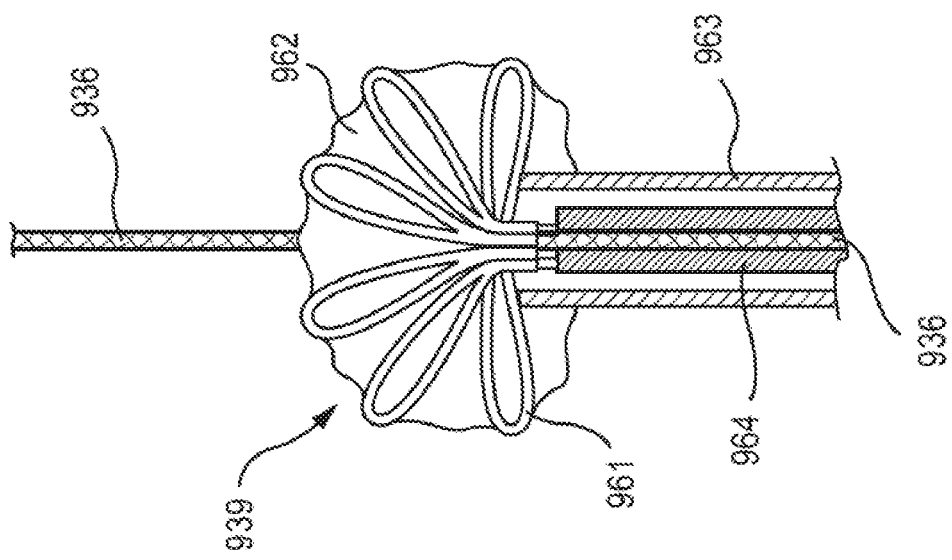
FIG. 34 is a side perspective view of the epicardial pad device of FIG. 33 shown in an expanded configuration.
Figure 33:
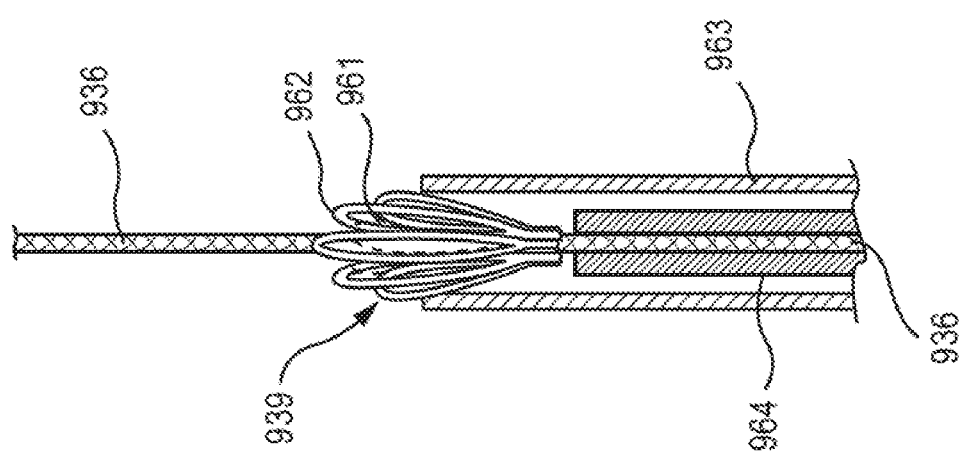
FIG. 33 is a side view of a portion of an epicardial pad device, according to an embodiment, and shown in a collapsed configuration within a delivery sheath.
Figure 35:
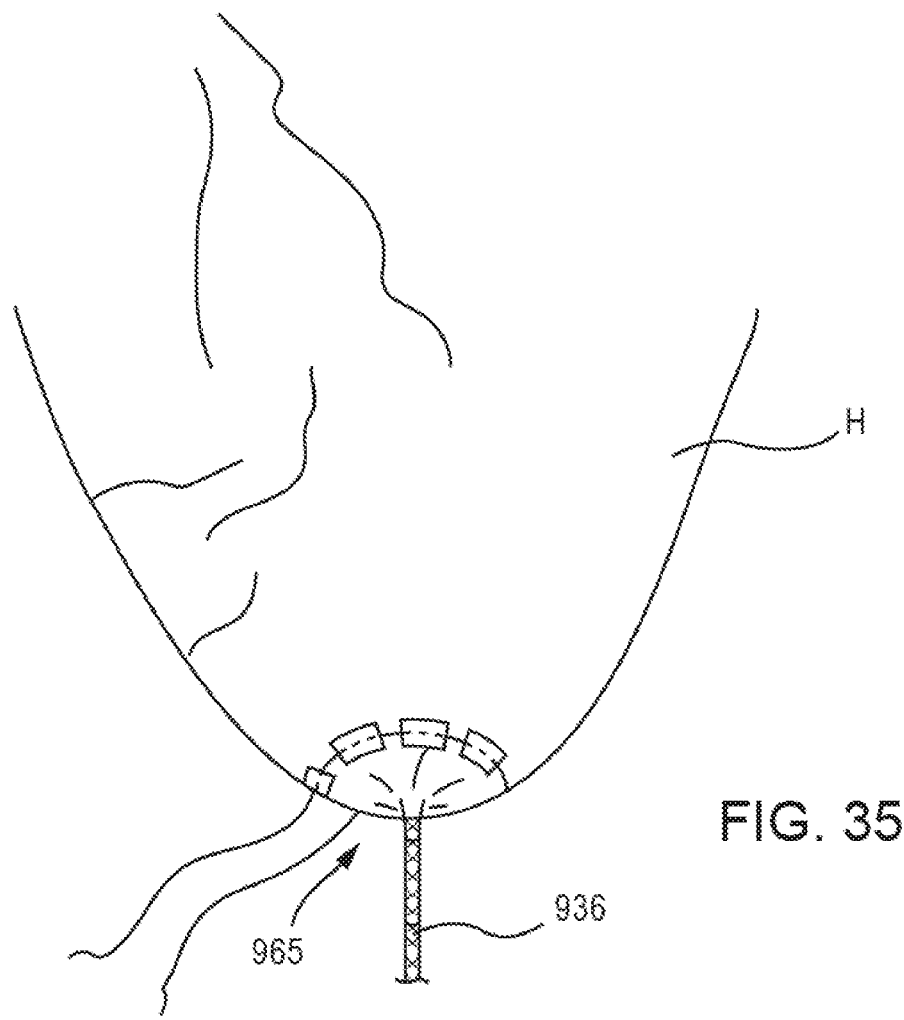
FIG. 35 is a side perspective view of a portion of a heart illustrating purse-string sutures at an apex of the heart prior to securing an epicardial pad device thereto.
Figure 36:
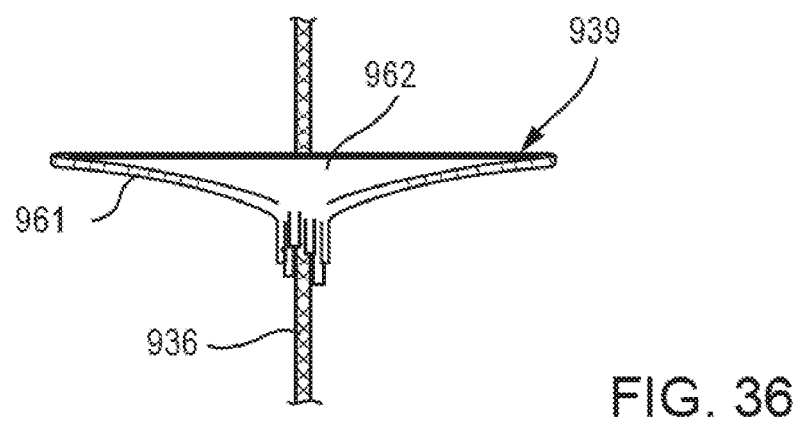
FIG. 36 is a side perspective view of the epicardial pad device of FIG. 33 shown in the expanded configuration.

As shown in FIGS. 33 and 34 the epicardial pad 939 includes a frame member 961 and a fabric cover 962. The frame member 961 can be formed with, for example a shape-memory material such as Nitinol® such that the epicardial pad 939 can have a biased expanded configuration as shown in FIGS. 34 and 36, and can be moved to a collapsed configuration as shown in FIG. 33. For example, as shown in FIG. 33 the epicardial pad 939 can be placed within a lumen of the delivery sheath 963 to move the epicardial pad 939 to the collapsed configuration. The fabric cover 962 can be formed with various suitable material(s) such as, for example, polyester, polyethylene or ePTFE.

In use, after a prosthetic mitral valve has been deployed within the heart H via a transfemoral delivery approach as described herein, the tether 936 attached the prosthetic valve (not shown) can extend outside the apex of the heart. The epicardial pad 939 can be used to secure the tether 936 and prosthetic valve in a desired position. With the tether 936 extending outside of the heart, the tether 936 can be threaded through a center opening of the epicardial pad 939 and through a lumen of the inner delivery sheath 964, as shown in FIGS. 33 and 34. The outer delivery sheath 963 can be laced over the inner delivery sheath 964 and the epicardial pad 939 to collapse the epicardial pad 939 as shown in FIG. 33. As described above, the outer delivery sheath 964 can have a relatively small outer diameter such that it can be inserted through a small incision in the skin of the patient. When the distal end of the delivery sheath 963 is at a desired location near the apex of the heart, the epicardial pad 939 can be moved outside of the delivery sheath 963 such that the epicardial pad 939 can assume its biased expanded configuration as shown in FIGS. 34 and 36. For example, to move the epicardial pad 939 outside of the lumen of the delivery sheath 963, the delivery sheath 963 can be moved proximally, such that the deliver sheath 963 is removed from epicardial pad 939. Alternatively, the epicardial pad 939 can be moved distally outside of the lumen of the delivery sheath 963. For example, a push rod (not shown) can be used, or the inner delivery sheath 964 in which the tether 936 is disposed can be used to move or push the epicardial pad 939 out of the delivery sheath 963.

Figure 38:
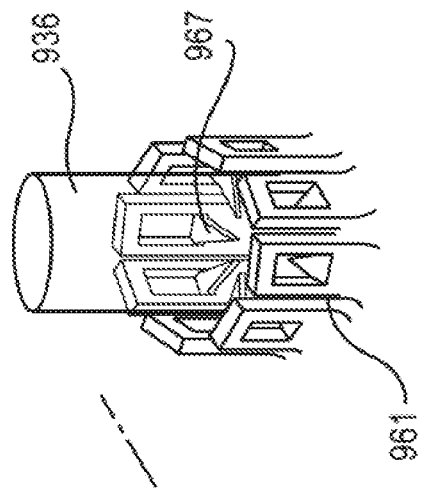
FIG. 38 is an enlarged side perspective view and FIG. 39 is an enlarged bottom view of a portion A in FIG. 37 illustrating an integrated locking mechanism.
Figure 39:
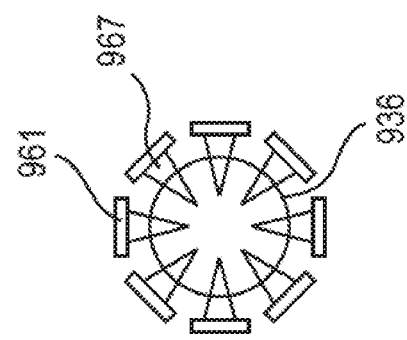
Figure 37:
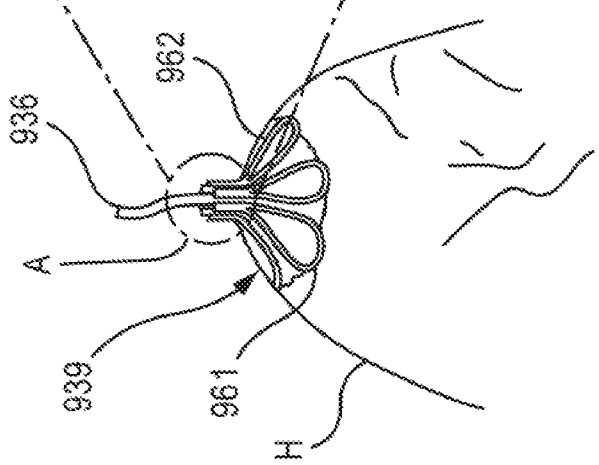
FIG. 37 is a bottom perspective view of a portion of a heart illustrating with the epicardial pad device of FIG. 33 secured thereto.

Prior to moving the expanded epicardial pad 939 into position on the apex of the heart, conventional purse string sutures 965 at the incision through which the tether 936 extends out of the heart at the apex of the heart can be closed. The epicardial pad 939, in the expanded configuration, can then be positioned on the apex of the heart. In this embodiment, the epicardial pad 939 includes an integral locking mechanism 966 as shown in FIGS. 37-39. The locking mechanism can be formed integrally with the frame member 961 and can include barbs 967. As shown in FIGS. 33 and 34, the tether 936 can be inserted through a lumen of the inner delivery sheath 964 such that the delivery sheath 964 can prevent the barbs 967 form contacting the tether 936. For example, the tether 936 can be threaded into the inner delivery sheath 964 prior to the inner delivery sheath 964 and tether 936 being inserted through the center opening of the epicardial pad 939. Thus, the inner delivery sheath 964 can protect the tether 936 from the barbs 967 of the locking mechanism 966 during deployment of the epicardial pad 939. When the epicardial pad 939 is deployed at the desired position on the heart, the inner delivery sheath 964 can be removed uncovering the tether 936 and allowing the barbs 967 to engage or pierce the tether 936 as shown in FIGS. 38 and 39. The barbs 968 can hold or lock the tether 936 and epicardial pad 939 in the desired positon. The barbs 968 can be oriented at various different angles relative to a longitudinal axis of the epicardial pad 939, such as, for example, between 45-120 degrees.

In alternative embodiments, other methods of securing the epicardial pad 939 to the heart can be used. For example, in an embodiment in which the epicardial pad 939 does not include an integrated locking mechanism as described above, the distal end portion of the tether 936 can be tied or another securing device such as a clip or locking pin can be used.

Figure 41:
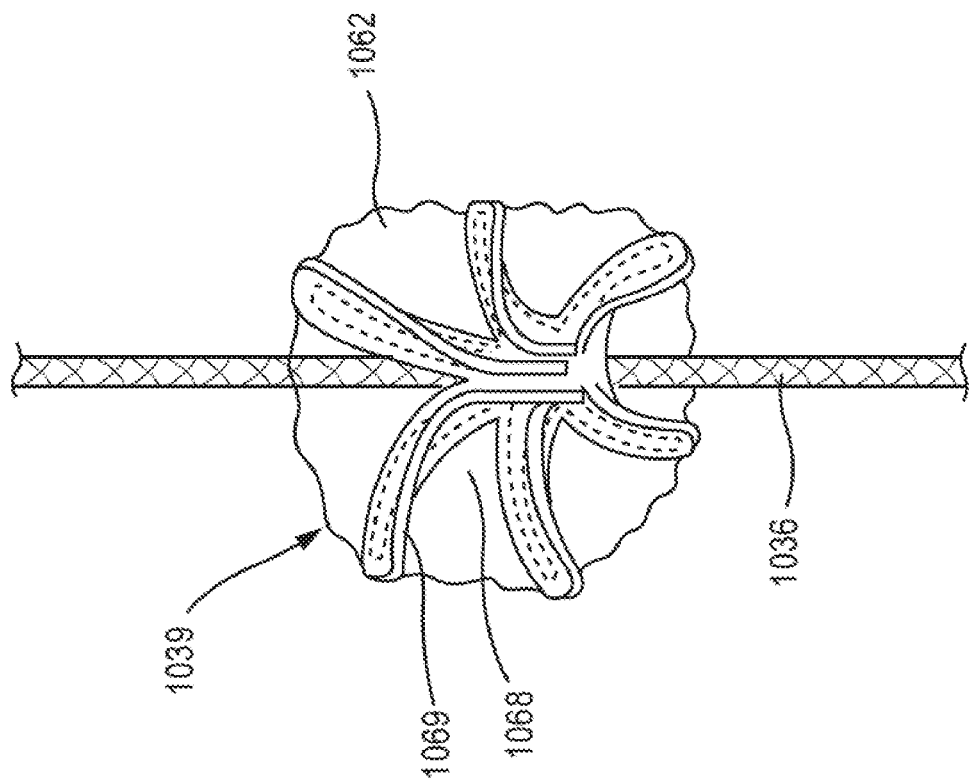
FIG. 41 is a side perspective view of the epicardial pad device of FIG. 40 shown in an expanded configuration.
Figure 40:
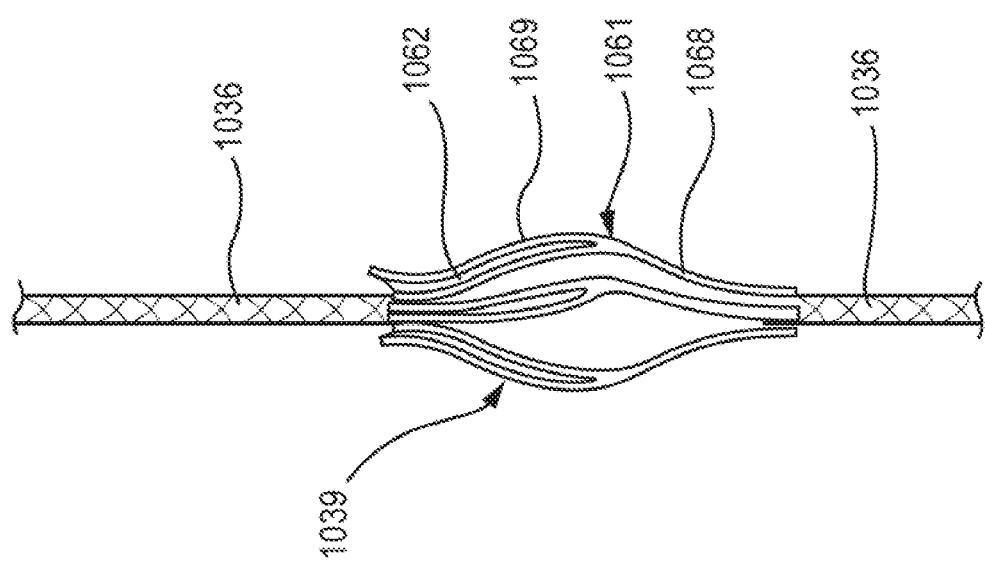
FIG. 40 is a side view of an epicardial pad device, according to another embodiment, and shown in a collapsed configuration.
Figure 42:
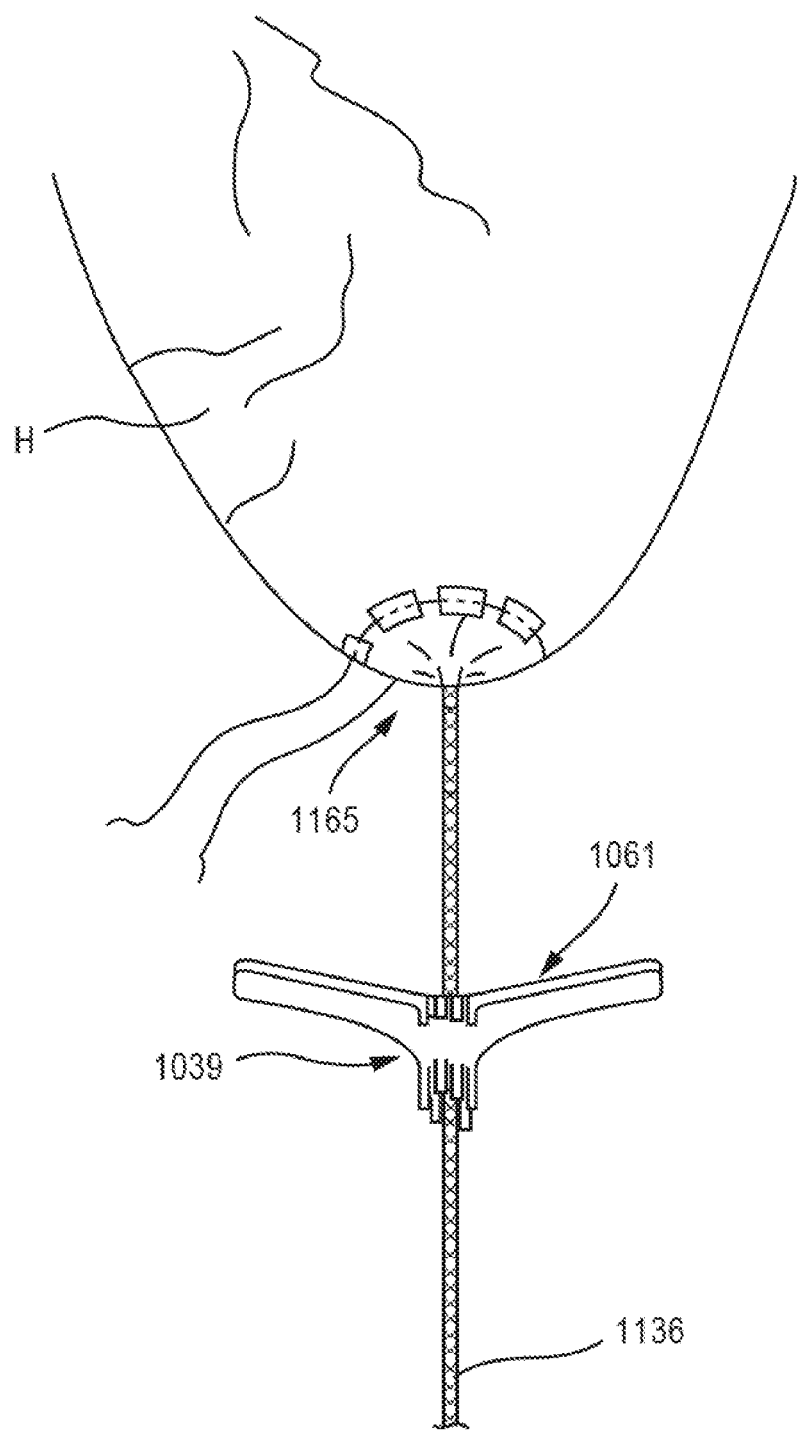
FIG. 42 is a side view of the epicardial device of FIG. 40 shown in the expanded configuration and being deployed near an apex of a heart.

FIGS. 40-42 illustrate another embodiment of an expandable epicardial pad device that can be used to secure a tether attached to a prosthetic mitral valve to the heart, for example, at the apex of the heart. An epicardial pad device 1039 (also referred to herein as "epicardial pad" or "pad") can be used, for example, during a procedure to deliver a prosthetic heart valve transfemorally as described herein. The epicardial pad 1039 can be formed with a small profile such that the epicardial pad 1039 can be delivered to the exterior of the heart via a small incision and a small diameter delivery catheter or sheath (not shown) as described above for epicardial pad 939.

As shown in FIGS. 40-42, the epicardial pad 1039 includes a frame member 1061 and a fabric cover 1062. In this embodiment, the frame member 1061 includes a first frame portion 1068 and a second frame portion 1069. As with the previous embodiment, the frame member 1061 can be formed with, for example a shape-memory material such as Nitinol®, such that the epicardial pad 1039 can have a biased expanded configuration as shown in FIGS. 41 and 42, and can be moved to a collapsed configuration as shown in FIG. 40. For example, although not shown for this embodiment, the epicardial pad 1039 can be placed within a lumen of a delivery sheath to collapse or move the epicardial pad 1039 to the collapsed configuration. In the expanded configuration, the second frame portion 1069 expands within an interior region defined by the first frame portion 1068 as best shown in FIG. 41. In other words, the second frame portion 1069 and the first frame portion 1068 form a double-layer flower-like shape. The fabric cover 1062 can be formed with, for example, various suitable material(s) such as, for example, polyester, polyethylene or ePTFE, as described above for fabric cover 962.

In use, after a prosthetic mitral valve has been deployed within the heart H (FIG. 42), for example, via a transfemoral delivery approach as described herein, the tether 1036 attached the prosthetic valve (not shown) can extend outside the apex of the heart. The epicardial pad 1039 can be used to secure the tether 1036 and prosthetic valve in a desired position. With the tether 1036 extending outside of the heart, the tether 1036 can be threaded through a lumen of an inner delivery sheath, such as inner delivery sheath 964 described above, and through a center opening of the epicardial pad 1039. An outer delivery sheath (not shown) can be placed over the inner delivery sheath such that the epicardial pad 1039 to collapse the epicardial pad 1039. As described above, the outer delivery sheath can have a relatively small outer diameter such that it can be inserted through a small incision in the skin of the patient. When the distal end of the delivery sheath is at a desired location near the apex of the heart, the epicardial pad 1039 can be moved outside of the delivery sheath 963 such that the epicardial pad 1039 can assume its biased expanded configuration as shown in FIGS. 41 and 42 as described above for epicardial pad 939.

Prior to moving the expanded epicardial pad 1039 into position on the apex of the heart, conventional purse string sutures 1065 at the incision through which the tether 1036 extends out of the heart at the apex of the heart can be closed. The epicardial pad 1039, in the expanded configuration, can then be positioned on the apex of the heart. The epicardial pad 1039 can include an integral locking mechanism, similar to or the same as locking mechanism 966 described above to secure or lock the tether 1036 and epicardial pad 1039 in position on the heart. In alternative embodiments, other methods of securing the epicardial pad 1039 to the heart can be used. For example, as described above, the distal end portion of the tether 1036 can be tied or another securing device such as a clip or locking pin can be used.

Figure 43:
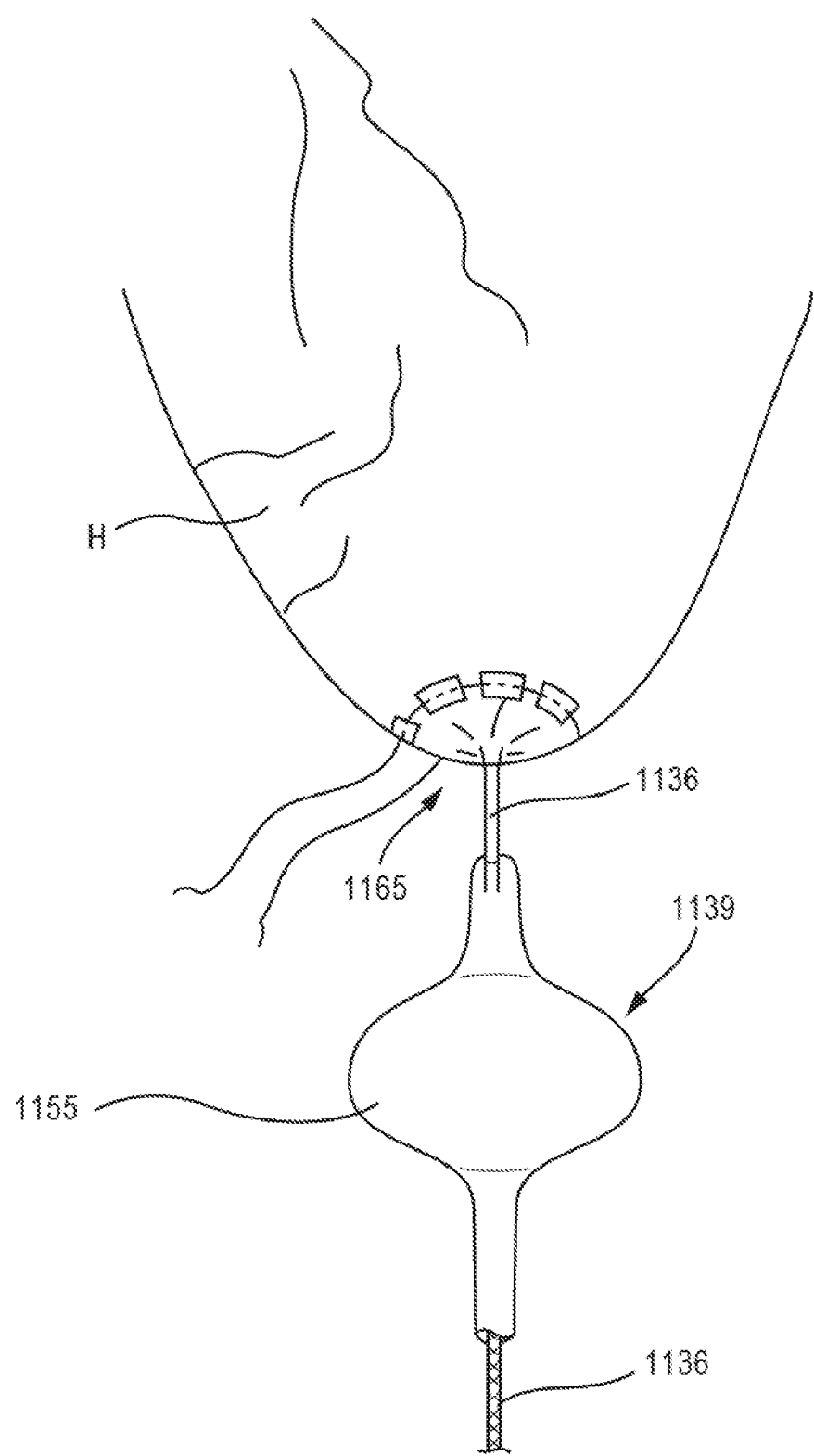
FIG. 43 is a side view of an epicardial pad device, according to another embodiment, and shown in an expanded configuration being deployed near a heart.
Figure 44:
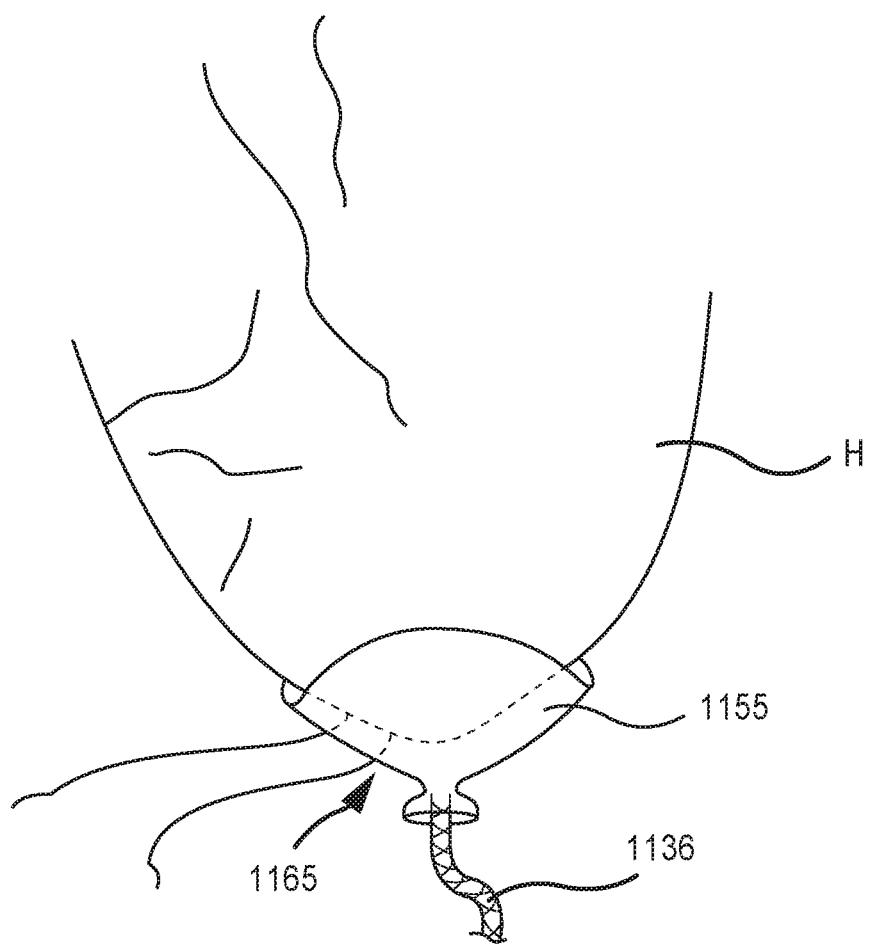
FIG. 44 is a side view of the epicardial pad device of FIG. 43 shown in a collapsed configuration and deployed on the apex of the heart.

FIGS. 43 and 44 illustrate an expandable epicardial pad device 1139 according to another embodiment. The epicardial pad device 1139 can be used in the same or similar manner as described for previous embodiments to secure a tether attached to a prosthetic mitral valve to the heart, for example, at the apex of the heart. The epicardial pad device 1139 (also referred to herein as "epicardial pad" or "pad") can be used, for example, during a procedure to deliver a prosthetic heart valve transfemorally as described herein. In this embodiment, the epicardial pad device 1139 includes a balloon member 1155. The balloon member 1155 can be small in size such that the balloon member 1155 can be delivered to the exterior of the heart via a small incision and a small diameter delivery catheter or sheath (not shown) as described above for previous embodiments.

The balloon member 1155 can define an inner lumen through which the tether 1136 can be inserted. The epicardial pad 1139 can also include an inflation lumen through which an inflation medium can be communicated to and from the balloon member 1155. For example, the inflation lumen (not shown) can be defined by the balloon member 1155 or by a separate inflation line (not shown) in fluid communication with an interior of the balloon member 1155.

In use, after a prosthetic mitral valve has been deployed within the heart H (FIG. 42), for example, via a transfemoral delivery approach as described herein, the tether 1136 attached the prosthetic valve (not shown) can extend outside the apex of the heart. With the tether 1136 extending outside of the heart, the tether 1136 can be threaded or inserted through the lumen of the balloon member 1155 as described above. The balloon member 1155 can be inflated or deflated when the tether 1136 is inserted into the balloon lumen. The balloon member 1155 can be collapsed or deflated (not shown) and then placed within a lumen of a delivery sheath (not shown). The delivery sheath can be inserted through a small incision in the skin of the patient and a distal end of the delivery sheath disposed at a desired location near the apex of the heart, The epicardial pad 1139 (i.e., balloon member 1155) can be moved outside of the delivery sheath and then can be inflated as shown in FIG. 43.

Purse string sutures 1165 at the incision through which the tether 1136 extends out of the heart at the apex of the heart can be closed prior to positioning the epicardial pad 1139 on the apex. Prior to positioning the balloon member 1155 on the apex of the heart, the balloon member 1155 can be partially deflated or fully deflated. The balloon member 1155 is then moved distally into contact with the heart where it can collapse inwardly upon itself to form a cup shape as the balloon member 1155 is pushed against the heart, as shown in FIG. 44. The epicardial pad 1139 and tether 1136 can be secured in the desired position with, for example, clip(s) or a locking pin(s) or by tying the tether 1136. In some embodiments, the balloon member 1155 is secured by adhesively coupling the balloon member 1155 to the tether 1136 such that the balloon member 1155 is prevented from moving relative to the tether 1136. In some embodiments, the balloon member 1155 can be adhesively coupled to the tether 1136 and also adhesively coupled to the heart. In some embodiments, the balloon member 1155 is fully deflated and can be filled with an adhesive or a cement material to add strength and rigidity to the balloon member 1155.

Figure 45:
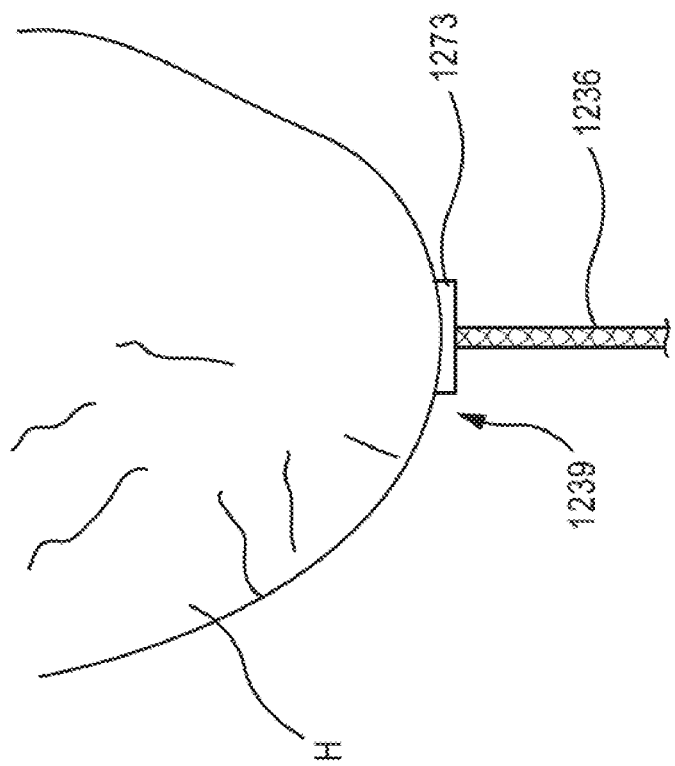
FIGS. 45 and 46 are each a side view of an epicardial pad device, according to another embodiment, and shown being deployed on an apex of a heart.
Figure 46:
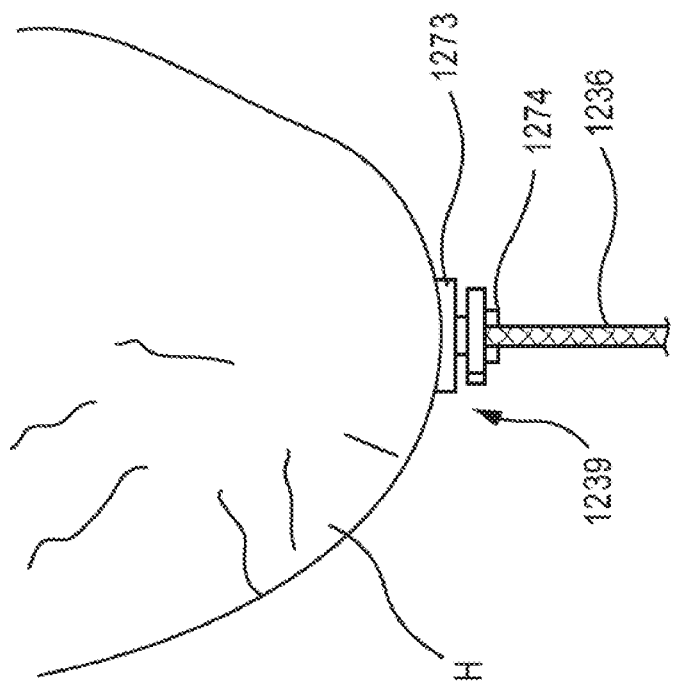
Figure 47:
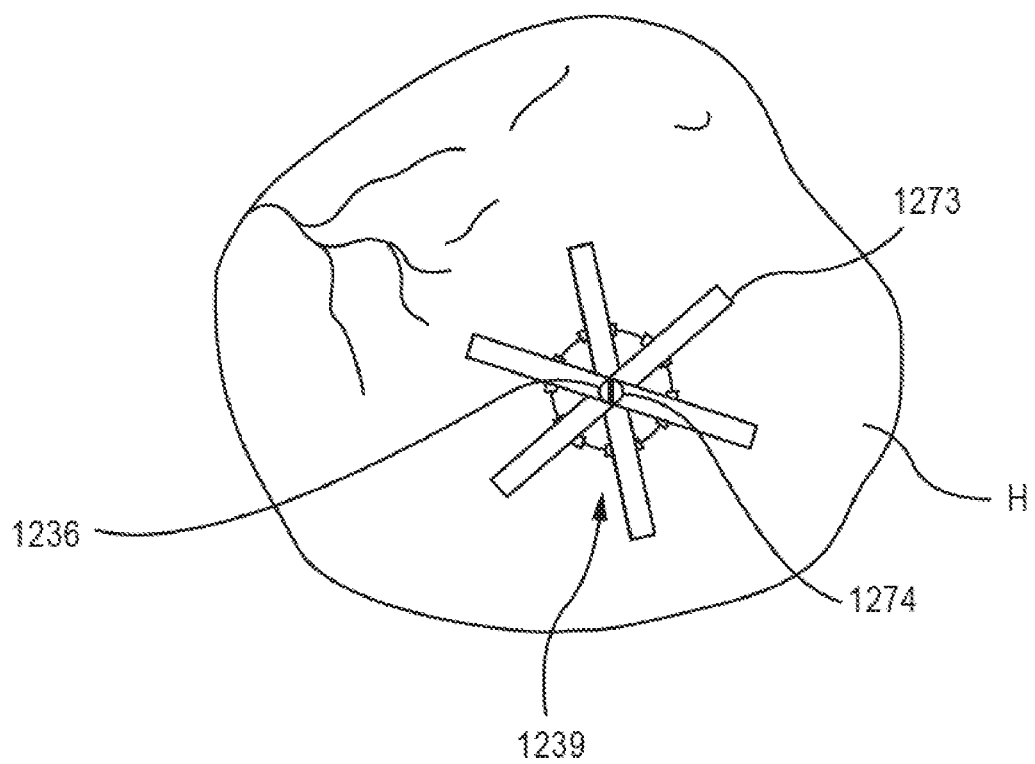
FIG. 47 is a bottom view of a heart with the epicardial pad of FIGS. 45 and 46 secured to the apex of the heart.

FIGS. 45-47 illustrate yet another embodiment of an epicardial pad device that can be used to secure a tether attached to a prosthetic mitral valve to the heart, for example, at the apex of the heart. The epicardial pad device 1239 (also referred to herein as "epicardial pad" or "pad") can be used, for example, during a procedure to deliver a prosthetic heart valve transfemorally as described herein. In this embodiment, the epicardial pad device 1239 includes multiple stackable pad members 1273 that can be sized such that each stackable pad member 1273 can be delivered separately to the exterior of the heart via a small incision and a small diameter delivery catheter or sheath (not shown). When all of the stackable pad members 1273 are implanted and attached to the heart, the stackable pad members 1273 can define a total surface area of, for example, 2 cm. The stackable pad members 1273 can be formed with, for example, suitable polymer or metal materials such as, for example, PEEK plastic, or stainless steel such as, for example, MP35N stainless steel.

In use, after a prosthetic mitral valve has been deployed within the heart H, for example, via a transfemoral delivery approach as described herein, the tether 1236 attached the prosthetic valve (not shown) can extend outside the apex of the heart. With the tether 1236 extending outside of the heart, a first stackable pad member 1273 can be slid onto the tether 1236. For example, the stacking members 1273 can define a through-hole in which the tether 1236 can be received. The first stackable pad member 1273 can be slid or moved distally along the tether 1236 until it contacts the surface of the heart H as shown in FIG. 45. A second stackable pad member 1273 can then be slid distally along the tether 1236 until it contacts the first stackable pad member 1273 and then a third stackable pad member 1273 can be slid distally along the tether 1236 until it contacts the second stackable pad member 1273 as shown in FIG. 45. Each stackable pad member 1273 can be oriented at a different angle relative to the tether 1236 as shown in FIG. 47. Using three separate stackable pad members 1273 in this manner can distribute the forces against the surface of the heart more evenly than a single stackable pad member 1273. After the three stackable pad members 1273 have been positioned against the heart, a locking pin 1274 can be inserted laterally through the tether 1236 to secure the stackable pad members 1273 against the surface of the heart. In some embodiments, it may be desirable to insert a locking pin after each stackable pad member 1273 has been positioned.

While various embodiments have been described above, it should be understood that they have been presented by way of example only, and not limitation. Where methods described above indicate certain events occurring in certain order, the ordering of certain events may be modified. Additionally, certain of the events may be performed concurrently in a parallel process when possible, as well as performed sequentially as described above Where schematics and/or embodiments described above indicate certain components arranged in certain orientations or positions, the arrangement of components may be modified. While the embodiments have been particularly shown and described, it will be understood that various changes in form and details may be made. Any portion of the apparatus and/or methods described herein may be combined in any combination, except mutually exclusive combinations. The embodiments described herein can include various combinations and/or sub-combinations of the functions, components, and/or features of the different embodiments described.

The invention claimed is:

1. A method, comprising:
   inserting a prosthetic mitral valve into a lumen of a delivery sheath such that the prosthetic mitral valve is in a collapsed condition, the prosthetic mitral valve having a tether coupled thereto such that the tether is positioned distal of the prosthetic mitral valve while the prosthetic mitral valve is within the lumen of the delivery sheath;
   while the prosthetic mitral valve is within the lumen of the delivery sheath, inserting the delivery sheath through an entry site of a femoral vein of a patient and moving the delivery sheath through the femoral vein and through a septum of a heart of the patient until a distal end portion of the delivery sheath is disposed in a left atrium of a heart of the patient;
   moving the prosthetic mitral valve distally out of the delivery sheath such that the prosthetic mitral valve is moved to an expanded condition;
   positioning the prosthetic mitral valve within a mitral annulus of the heart;
   coupling an epicardial pad device to the tether;
   forming an access site at an apex of the heart, wherein the tether extends through the access site at the apex of the heart,
   securing the epicardial pad device to the apex of the heart, wherein during the positioning of the prosthetic mitral valve within the mitral annulus of the heart, a wire assist structure directly contacts a frame of the prosthetic mitral valve to hold the frame and allow for axial positioning control of the prosthetic mitral valve, and after the positioning of the prosthetic mitral valve, disconnecting the wire assist structure from the frame and removing the wire assist structure through the femoral vein, wherein the prosthetic mitral valve does not pass through the access site at the apex of the heart after being inserted through the entry site of the femoral vein;

wherein the tether is a continuous braided cord, and the tether extends through the access site at the apex of the heart prior to moving the prosthetic mitral valve to the expanded condition.

2. The method of claim 1, wherein the wire assist structure is releasably coupled to an inner frame of the prosthetic mitral valve during the positioning of the prosthetic mitral valve within the mitral valve annulus of the heart.

3. The method of claim 2, wherein during the positioning of the prosthetic heart valve within the mitral annulus of the heart, an outer frame of the prosthetic mitral valve is in an expanded state while the inner frame of the prosthetic mitral valve is in a collapsed state.

4. The method of claim 3, wherein the prosthetic mitral valve is capable of functioning during positioning of the prosthetic mitral valve within the mitral annulus of the heart, prior to fully releasing the prosthetic mitral valve from the delivery sheath.

5. The method of claim 4, further comprising advancing the inner frame of the prosthetic mitral valve through the delivery sheath using the wire assist structure while the outer frame is in the expanded state.

6. The method of claim 4, further comprising rotating the inner frame of the prosthetic mitral valve using the wire assist structure while the inner frame is within the delivery sheath and the outer frame is in the expanded state.

7. The method of claim 4, further comprising releasing the wire assist structure from the inner frame of the prosthetic mitral valve after positioning the prosthetic mitral valve within the mitral annulus of the heart.

8. The method of claim 4, further comprising:

prior to inserting the delivery sheath, inserting a leader tube through the access site at the apex of the heart and positioning a distal end portion of the leader tube in the left atrium of the heart;

inserting a snare device into the femoral vein and into the left atrium of the heart;

capturing the leader tube with the snare device; and pulling the snare device and leader tube out of the femoral vein such that the leader tube extends between the apex of the heart and the entry to the femoral vein.

9. The method of claim 8, further comprising:

inserting a valve leader member into the leader tube and moving the valve leader member through the leader tube until the valve leader member exits the leader tube outside of the apex of the heart, a proximal end of the valve leader member being coupled to a tether line coupled to the prosthetic mitral valve and disposed within the delivery sheath.

10. The method of claim 4, further comprising:

prior to inserting the delivery sheath, inserting a leader tube through an apex of the heart and positioning a distal end portion of the leader tube in the left ventricle of the heart;

inserting a snare device into the femoral vein and into the left ventricle of the heart;

capturing the leader tube with the snare device; and pulling the snare device and leader tube out of the entry site of the femoral vein such that the leader tube extends between the access site at the apex of the heart and the entry site to the femoral vein.

11. A method, comprising:

inserting a prosthetic mitral valve into a lumen of a delivery sheath such that the prosthetic mitral valve is in a collapsed condition, the prosthetic mitral valve having a tether coupled thereto such that the tether is positioned distal of the prosthetic mitral valve while the prosthetic mitral valve is within the lumen of the delivery sheath;

while the prosthetic mitral valve is within the lumen of the delivery sheath, inserting the delivery sheath through an entry site of a femoral vein of a patient and moving the delivery sheath through the femoral vein and through a septum of a heart of the patient until a distal end portion of the delivery sheath is disposed in a left atrium of a heart of the patient;

moving the prosthetic mitral valve distally out of the delivery sheath such that the prosthetic mitral valve is moved to an expanded condition;

positioning the prosthetic mitral valve within a mitral annulus of the heart;

coupling an epicardial pad device to the tether;

forming an access site at an apex of the heart, wherein the tether extends through the access site at the apex of the heart, securing the epicardial pad device to the apex of the heart, wherein during the positioning of the prosthetic mitral valve within the mitral annulus of the heart, an assist member is movably disposed within the delivery sheath and is disposed over a portion of an inner frame of the prosthetic mitral valve, and after the positioning of the prosthetic mitral valve, removing the assist structure from the frame through the femoral vein wherein while the valve is in the collapsed condition, an outer frame of the prosthetic mitral valve is inverted so that a terminal end of the outer frame faces away from a terminal end of the inner frame, and during deployment, the outer frame reverts so that the terminal ends of the outer frame and inner frame face a same direction, wherein the prosthetic mitral valve does not pass through the access site at the apex of the heart after being inserted through the entry site of the femoral vein, wherein the tether is a continuous braided cord, and the tether extends through the access site at the apex of the heart prior to moving the prosthetic mitral valve to the expanded condition.

12. The method of claim 11, wherein the assist member is a tubular member defining a lumen having a diameter sized to receive at least a portion of the inner frame of the prosthetic mitral valve.

13. The method of claim 12, wherein during the positioning of the prosthetic heart valve within the mitral annulus of the heart, the outer frame of the prosthetic mitral valve is in at least a partially expanded state while the inner frame of the prosthetic mitral valve is in a collapsed state.

14. The method of claim 13, wherein the prosthetic mitral valve is capable of at least partially functioning during positioning the prosthetic mitral valve within the mitral annulus of the heart, prior to fully releasing the prosthetic mitral valve from the delivery sheath.

15. The method of claim 13, further comprising advancing the inner frame of the prosthetic mitral valve through the delivery sheath using the assist member while the outer frame is in at least the partially expanded state.

16. The method of claim 13, further comprising rotating the inner frame of the prosthetic mitral valve using the assist member while the inner frame is within the delivery sheath and the outer frame is in at least the partially expanded state.

17. The method of claim 13, further comprising fully releasing the inner frame from the assist member.

18. The method of claim 13, further comprising:
prior to inserting the delivery sheath, inserting a leader tube through the access site at the apex of the heart and positioning a distal end portion of the leader tube in the left atrium of the heart;
inserting a snare device into the femoral vein and into the left atrium of the heart;
capturing the leader tube with the snare device; and
pulling the snare device and leader tube out of the femoral vein such that the leader tube extends between the apex of the heart and the entry to the femoral vein.

19. The method of claim 18, further comprising:
inserting a valve leader member into the leader tube and moving the valve leader member through the leader tube until the valve leader member exits the leader tube outside of the apex of the heart, a proximal end of the valve leader member being coupled to a tether line coupled to the prosthetic mitral valve and disposed within the delivery sheath.

20. The method of claim 13, further comprising:
prior to inserting the delivery sheath, inserting a leader tube through an apex of the heart and positioning a distal end portion of the leader tube in the left ventricle of the heart;
inserting a snare device into the femoral vein and into the left ventricle of the heart;
capturing the leader tube with the snare device; and
pulling the snare device and leader tube out of the entry site of the femoral vein such that the leader tube extends between the access site at the apex of the heart and the entry site to the femoral vein.

* * * * *